United States Patent
Patterson et al.

(10) Patent No.: US 12,298,309 B2
(45) Date of Patent: *May 13, 2025

(54) METHODS OF ASSAYING NEOPLASTIC AND NEOPLASIA-RELATED CELLS AND USES THEREOF

(71) Applicant: IncellDx, Inc., Hayward, CA (US)

(72) Inventors: Bruce K. Patterson, Hayward, CA (US); Amanda Noel Chargin, Hayward, CA (US); Keith Shults, Hayward, CA (US)

(73) Assignee: IncellDx, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/211,038

(22) Filed: Jun. 16, 2023

(65) Prior Publication Data

US 2024/0077485 A1 Mar. 7, 2024

Related U.S. Application Data

(63) Continuation of application No. 16/959,355, filed as application No. PCT/US2019/012074 on Jan. 2, 2019, now Pat. No. 11,726,089, which is a continuation-in-part of application No. 15/861,352, filed on Jan. 3, 2018, now Pat. No. 10,782,298, which is a continuation-in-part of application No. PCT/US2017/050322, filed on Sep. 6, 2017.

(60) Provisional application No. 62/384,037, filed on Sep. 6, 2016.

(51) Int. Cl.
*C12Q 1/6886* (2018.01)
*G01N 15/1434* (2024.01)
*G01N 33/574* (2006.01)

(52) U.S. Cl.
CPC ..... *G01N 33/57423* (2013.01); *C12Q 1/6886* (2013.01); *G01N 15/1434* (2013.01); *C12Q 2600/118* (2013.01); *C12Q 2600/158* (2013.01); *G01N 2333/70532* (2013.01)

(58) Field of Classification Search
CPC .............................................. G01N 33/57423
USPC ....................................................... 514/789
See application file for complete search history.

(56) References Cited

U.S. PATENT DOCUMENTS

| | | |
|---|---|---|
| 7,892,540 B2 | 2/2011 | Chen et al. |
| 2013/0309250 A1 | 11/2013 | Cogswell et al. |
| 2015/0071910 A1 | 3/2015 | Kowanetz et al. |
| 2015/0079109 A1 | 3/2015 | Li et al. |
| 2015/0118247 A1 | 4/2015 | Hotson et al. |
| 2016/0108123 A1 | 4/2016 | Freeman et al. |
| 2017/0242016 A1 | 8/2017 | Dittamore |

FOREIGN PATENT DOCUMENTS

| | | |
|---|---|---|
| CN | 104470949 A | 3/2015 |
| JP | 2006-512579 A | 4/2006 |
| JP | 2015-197426 A | 11/2015 |
| WO | WO2007136025 A1 | 11/2007 |
| WO | WO2015034820 A1 | 3/2015 |
| WO | WO2016061064 A1 | 4/2016 |
| WO | WO2017040620 A1 | 3/2017 |
| WO | WO2017072539 A1 | 5/2017 |
| WO | WO2018048936 A1 | 3/2018 |

OTHER PUBLICATIONS

Azuma et al., Association of PD-L1 overexpression with activating EGFR mutations in surgically resected nonsmall-cell lung cancer, Ann Oncol. Oct. 2014;25(10):1935-40.
Chargin et al., Quantification of PD-L1 and PD-1 expression on tumor and immune cells in non-small cell lung cancer (NSCLC) using non-enzymatic tissue dissociation and flow cytometry, Cancer Immunol Immunother. Aug. 2016;65(11):1317-1323.
Chen et al., Anti-PD-1/PD-L1 therapy of human cancer: past, present, and future, J Clin Invest. Sep. 2015;125(9):3384-91.
Chen et al., Upregulation of PD-L1 by EGFR Activation Mediates the Immune Escape in EGFR-Driven NSCLC: Implication for Optional Immune Targeted Therapy for NSCLC Patients with EGFR Mutation, J Thorac Oncol. Jun. 2015;10(6):910-23.
Daud et al., Tumor immune profiling predicts response to anti-PD-1 therapy in human melanoma, J Clin Invest. Sep. 1, 2016;126(9):3447-52.
Gettinger et al., Overall Survival and Long-Term Safety of Nivolumab (Anti-Programmed Death 1 Antibody, BMS-936558, ONO-4538) in Patients With Previously Treated Advanced Non-Small-Cell Lung Cancer, J Clin Oncol. Jun. 20, 2015; 33(18): 2004-2012.
Herbst et al., Predictive correlates of response to the anti-PD-L1 antibody MPDL3280A in cancer patients, ure. Nov. 27, 2014;515(7528):563-7.
Nazareth et al., Characterization of human lung tumor-associated fibroblasts and their ability to modulate the activation of tumor-associated T cells, J Immunol. May 1, 2007;178(9):5552-62.

(Continued)

*Primary Examiner* — Sean E Aeder
(74) *Attorney, Agent, or Firm* — Melissa L. Nakamoto; Bret E. Field; Bozicevic, Field & Francis LLP

(57) ABSTRACT

Methods are provided for assaying neoplastic cells and/or neoplasia-related cells. Aspects of the methods involve detecting heterogeneity, per cell programmed-death ligand 1 (PD-L1) expression, and/or proliferation of neoplasia and/or neoplasia-related cells. Aspects of the methods include cytometrically assaying a labeled cell suspension to quantify per cell heterogeneity, per cell PD-L1 expression, proliferation, and/or other parameters to detect whether a neoplastic cell is present in the neoplasia sample. Aspects of the provided methods also include treating a subject based on the outcome of such an assay. In addition, kits that find use in practicing the subject methods are also provided.

12 Claims, 12 Drawing Sheets

Specification includes a Sequence Listing.

(56) References Cited

OTHER PUBLICATIONS

Pan et al., Clinicopathological and prognostic significance of programmed cell death ligand1 (PD-L1) expression in patients with non-small cell lung cancer: a meta-analysis, J Thorac Dis. Mar. 2015; 7(3): 462-470.
Patel et al., PD-L1 Expression as a Predictive Biomarker in Cancer Immunotherapy, Mol Cancer Ther. Apr. 2015;14(4):847-56.
Velcheti et al., Programmed death ligand-1 expression in non-small cell lung cancer, Lab Invest. Jan. 2014;94(1):107-16.
Yamane et al., Programmed cell death protein 1 and programmed death-ligand 1 are expressed on the surface of some small-cell lung cancer lines, Am J Cancer Res. Apr. 1, 2015; 5(4): 1553-1557.
Zak et al., Structural basis for small molecule targeting of the programmed death ligand 1 (PD-L1), Oncotarget. May 24, 2016; 7(21): 30323-30335.
Chargin et al., Abstract 1372: Quantification of PD-L1 and PD-1 expression on tumor cells in non-small cell lung cancer (NSCLC) using non-enzymatic tissue dissociation and flow cytometry, Proceedings: AACR 107th Annual Meeting 2016; Apr. 16-20, 2016; New Orleans, LA, 2 pages.
Picot et al., Flow cytometry: retrospective, fundamentals and recent instrumentation, Cytotechnology, Jan. 21, 2012, vol. 64, p. 109-130.
Tumeh et al., PD-1 blockade induces responses by inhibiting adaptive immune resistance, Nature, Nov. 27, 2014, vol. 515, p. 568-571.
Hapten (Lexico https://www.lexico.com/en/definition/hapten, May 26, 2020) (Year: 2020).
Yin et al., Significance of the Diagnosis of DNA Ploid and SPF Mensuration of the Pleural Fluid and the Ascitic Cells by Flow Cytometry, Shaanxi Journal of Medical Laboratory Sciences, Nov. 2000, No. 4, p. 22-23, with English abstract, 2 pages.
Zhu et al., Application of DNA Ploidy Analysis in the Diagnosis of Malignant Pericardial Effusion, Practical Clinical Journal of Integrative Medicine, vol. 7, No. 3, Jun. 2007, p. 73-74, with English abstract, 3 pages.
Du et al., Increased expression of the immune modulatory molecule PD-L1 (CD274) in anaplastic meningioma, Oncotarget. Mar. 10, 2015; 6(7):4704-16.
Mazel et al., Frequent expression of PD-L1 on circulating breast cancer cells, Mol Oncol. Nov. 2015; 9(9):1773-82.
Nicolazzo et al., Monitoring PD-L1 positive circulating tumor cells in non-small cell lung cancer patients treated with the PD-1 inhibitor Nivolumab, Sci Rep. Aug. 24, 2016; 6:31726.
Sarioglu et al., A microfluidic device for label-free, physical capture of circulating tumor-cell clusters, Nat Methods. Jul. 2015; 12(7):685-91.
Nanda et al., Pembrolizumab in Patients With Advanced Triple-Negative Breast Cancer: Phase Ib KEYNOTE-012 Study, J Clin Oncol. Jul. 20, 2016; 34(21):2460-7.

FIG. 5

| | IHC | | | | | OncoTect iO Lung | | | | | | | | |
|---|---|---|---|---|---|---|---|---|---|---|---|---|---|---|
| Sample | % PD-L1+ Tumor | %PD-L1+ CD45 negative | %PD-L1+ CTL (CD3+/CD8+) | %PD-L1+ Aneuploid (if DNA index >1.05) | CD45 (-) % Parent | Lymphocyte % Parent | All CD3+ % Parent | CTL % Parent | %CD4 (non-CD8+) | CD4/CD8 ratio | CD45 (-) Median PB450-A | Lymphocyte Median PB450-A | DNA Index (CD45(-)/ lymphocyte) |
| 1 | 0 | 0.19% | 0.00% | 0.30% | 60.65% | 10.05% | 42.83% | 10.31% | 32.52% | 3.15 | 1208575.6 | 697300.5 | 1.73 |
| 2 | 0 | 0.01% | 0.00% | | 74.05% | 7.29% | 46.24% | 24.97% | 21.27% | 0.85 | 1820724.9 | 1824173 | 1.00 |
| 3 | 0 | 0.01% | 0.00% | 0.02% | 65.53% | 13.02% | 70.80% | 32.16% | 38.64% | 1.20 | 3135535 | 1669713.4 | 1.88 |
| 4 | 50-60% | 11.67% | 0.10% | 19.76% | 33.16% | 17.29% | 72.35% | 36.88% | 35.47% | 0.96 | 3003191 | 1571449.8 | 1.91 |
| 5 | 0 | 0.15% | 0.00% | 0.18% | 49.55% | 10.79% | 82.23% | 31.19% | 51.04% | 1.64 | 5032315.5 | 1838021.3 | 2.74 |
| 6 | 0 | 4.42% | 0.08% | 8.54% | 8.51% | 60.65% | 81.65% | 30.09% | 51.56% | 1.71 | 2356396.5 | 1693756.1 | 1.39 |
| 7 | 0 | 0.23% | 0.03% | 0.44% | 38.68% | 25.23% | 77.46% | 51.02% | 26.44% | 0.52 | 2316600.8 | 1887926 | 1.23 |
| 8 | <1.0% | 0.11% | 0.55% | 0.18% | 76.40% | 2.47% | 75.54% | 46.03% | 29.51% | 0.64 | 1715225 | 1208179.9 | 1.42 |
| 9 | <1.0% | 1.26% | 0.05% | | 32.47% | 42.51% | 51.39% | 17.60% | 33.59% | 1.89 | 1587451 | 1587886.8 | 1.00 |
| 10 | <1.0% | 3.62% | 0.00% | 7.59% | 25.16% | 52.83% | 57.02% | 22.90% | 34.12% | 1.49 | 1377575.6 | 1293578.4 | 1.06 |
| 11 | 10% | 9.14% | 0.04% | 12.54% | 25.83% | 54.04% | 73.71% | 44.27% | 29.44% | 0.67 | 2401391.0 | 1399849.8 | 1.72 |
| 12 | <1% (remaining is histiocyte staining) | 2.08% | 0.29% | 2.12% | 23.25% | 54.33% | 85.97% | 49.83% | 36.14% | 0.73 | 3886923.3 | 1563920.0 | 2.49 |
| 13 | <1% | 24.05% | 0.07% | 40.83% | 15.72% | 62.70% | 57.31% | 20.33% | 36.98% | 1.82 | 3093016.0 | 1764764.5 | 1.75 |
| 14 | 0% | 0.03% | 0.28% | 0.03% | 31.81% | 51.65% | 58.37% | 11.20% | 47.17% | 4.21 | 1909978.1 | 1686136.5 | 1.13 |
| 15 | <1% (remaining is histiocyte staining) | 0.66% | 0.00% | 1.10% | 23.48% | 54.18% | 81.74% | 39.17% | 42.57% | 1.09 | 1550818.4 | 1478734.5 | 1.05 |
| 16 | 0% | 0.40% | 0.05% | 0.70% | 48.83% | 31.54% | 75.71% | 21.44% | 54.27% | 2.53 | 2040087.0 | 1556169.4 | 1.31 |
| 17 | 80% | 6.27% | 0.12% | 6.83% | 29.42% | 42.74% | 72.65% | 33.10% | 39.55% | 1.19 | 2197982.5 | 1613720.5 | 1.36 |
| 18 | 0% | 0.07% | 0.17% | 0.05% | 57.63% | 12.93% | 84.89% | 51.77% | 33.12% | 0.64 | 1765705.0 | 1613895.8 | 1.09 |
| 19 | 80% | 6.51% | 0.00% | 7.65% | 65.37% | 6.34% | 61.42% | 35.95% | 25.46% | 0.71 | 2422451.8 | 1480439.5 | 1.63 |

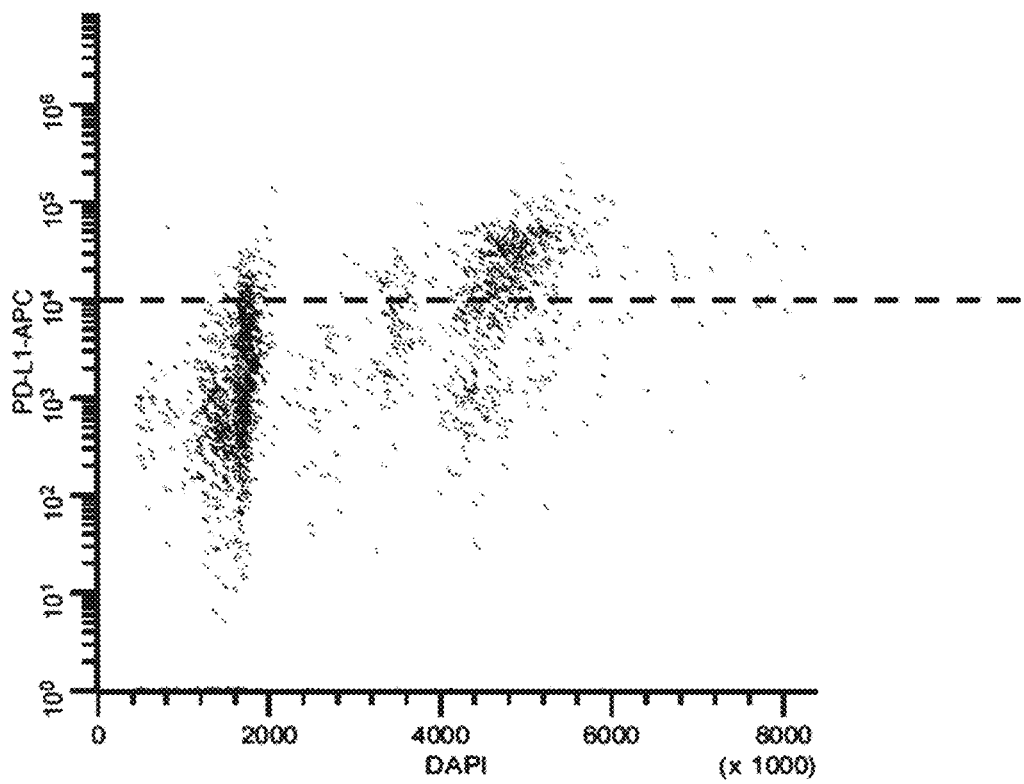
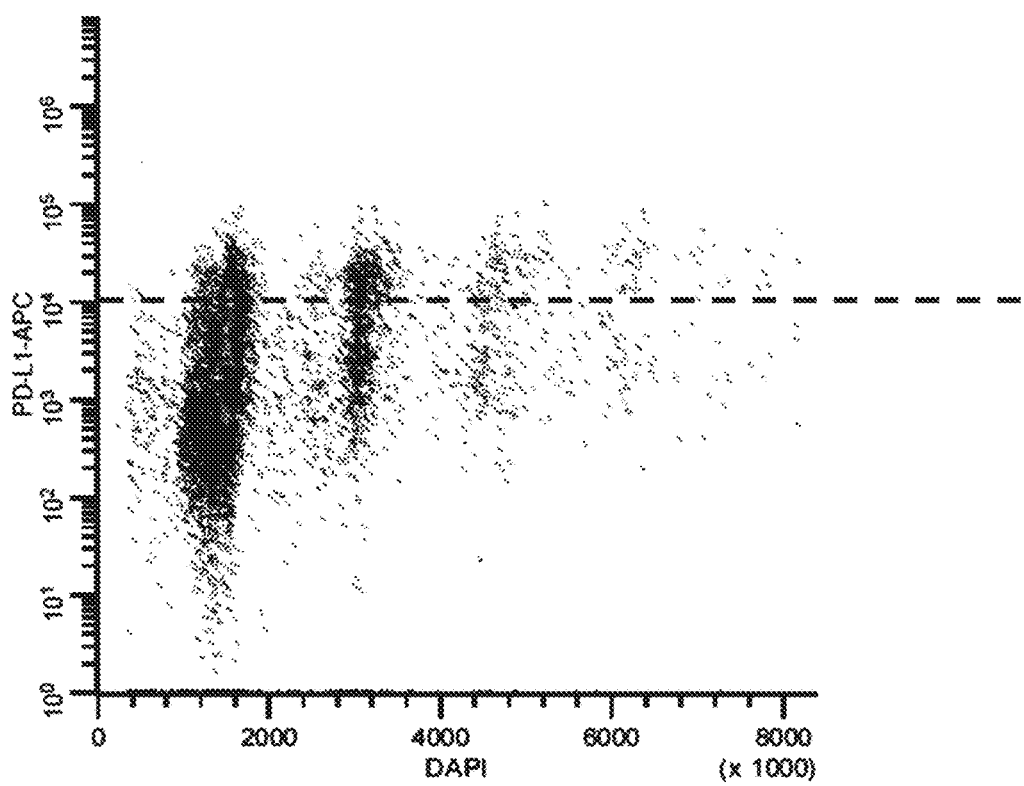
FIG. 9

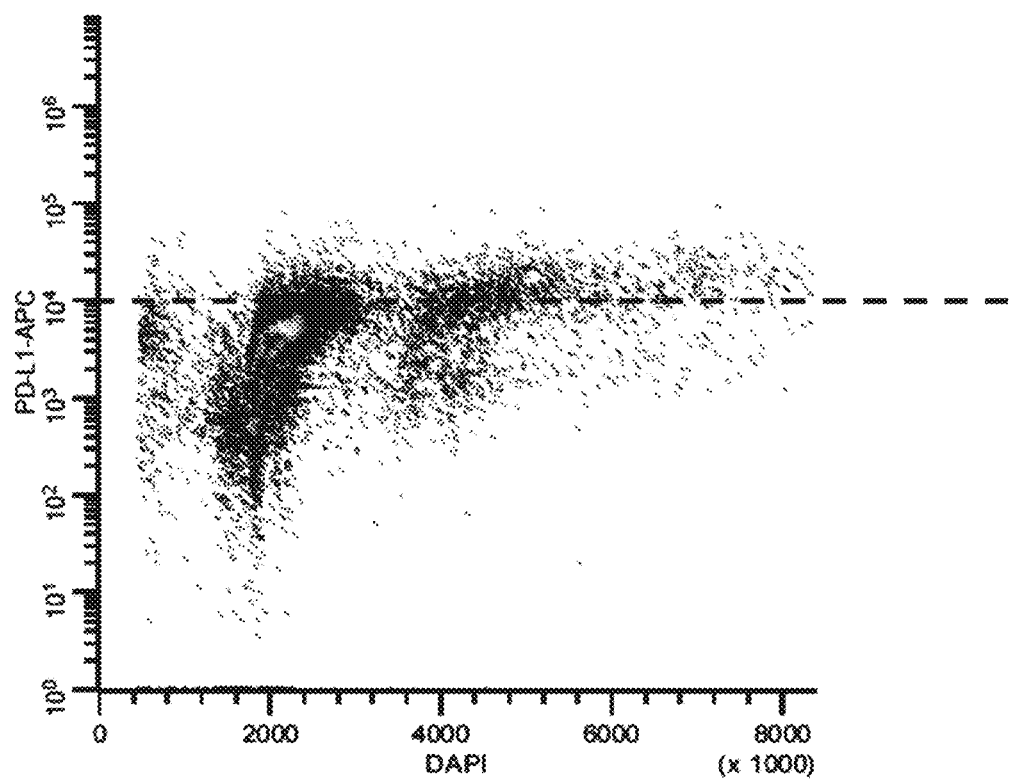
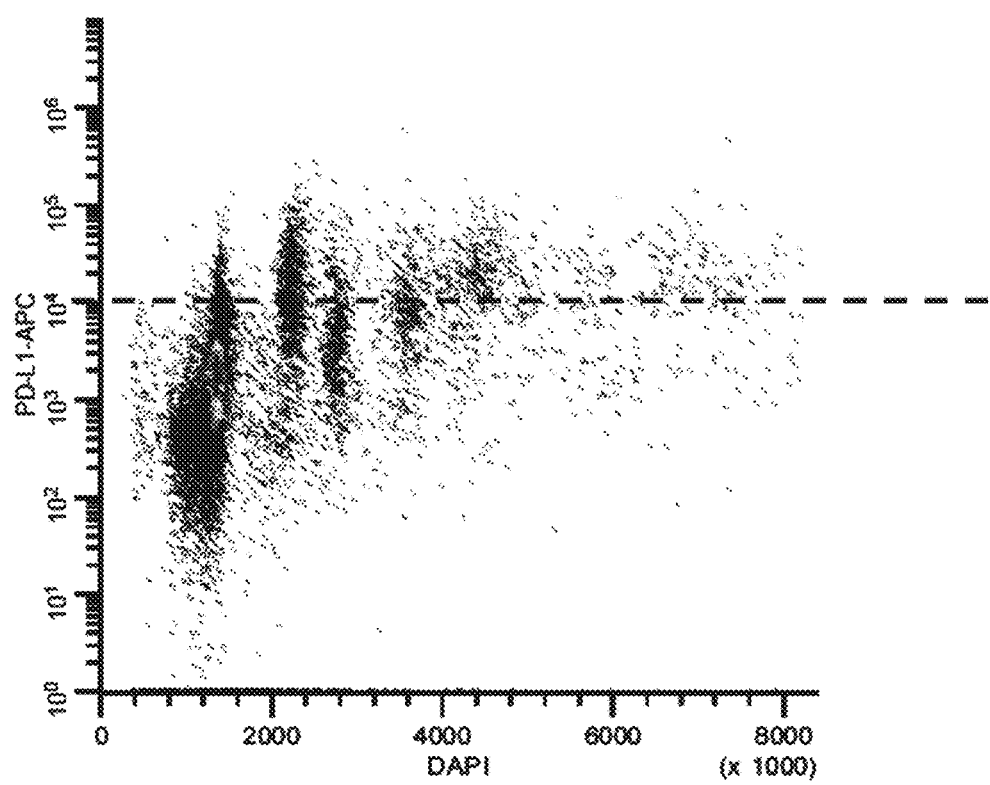
FIG. 9 (cont.)

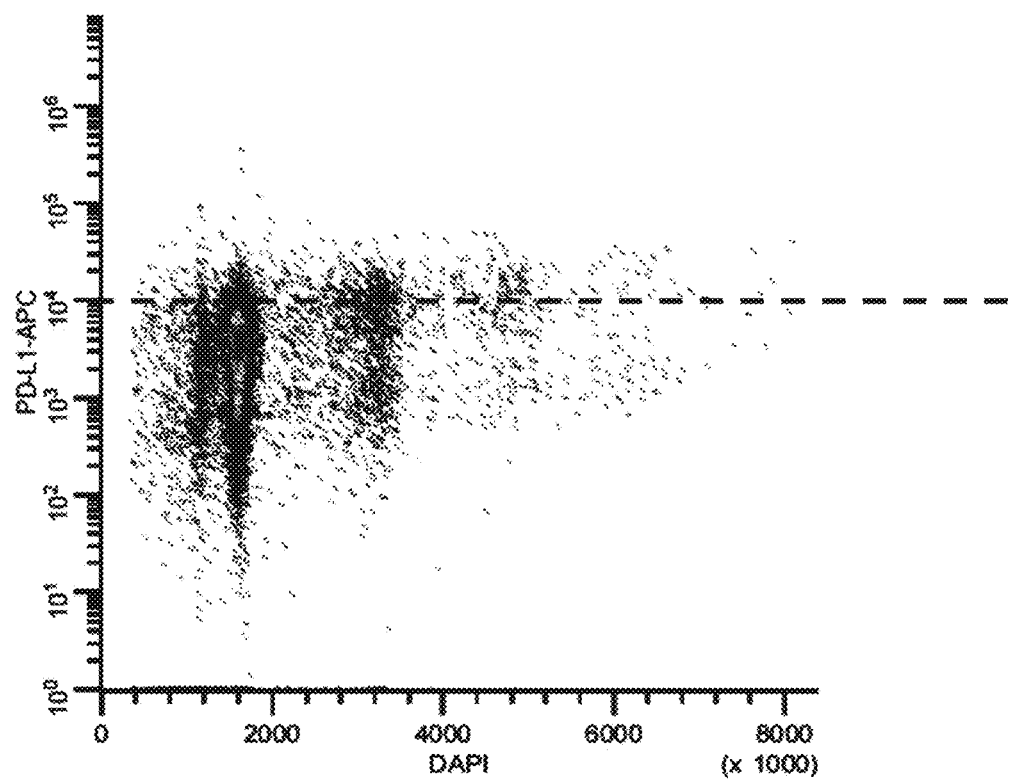
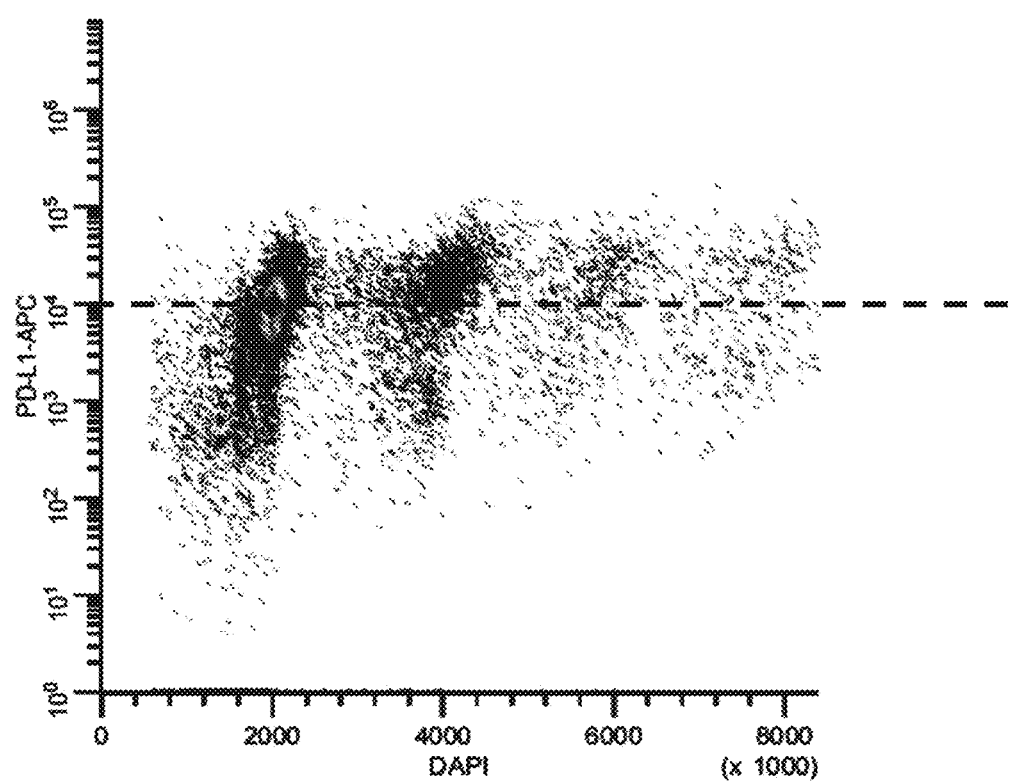
FIG. 9 (cont.)

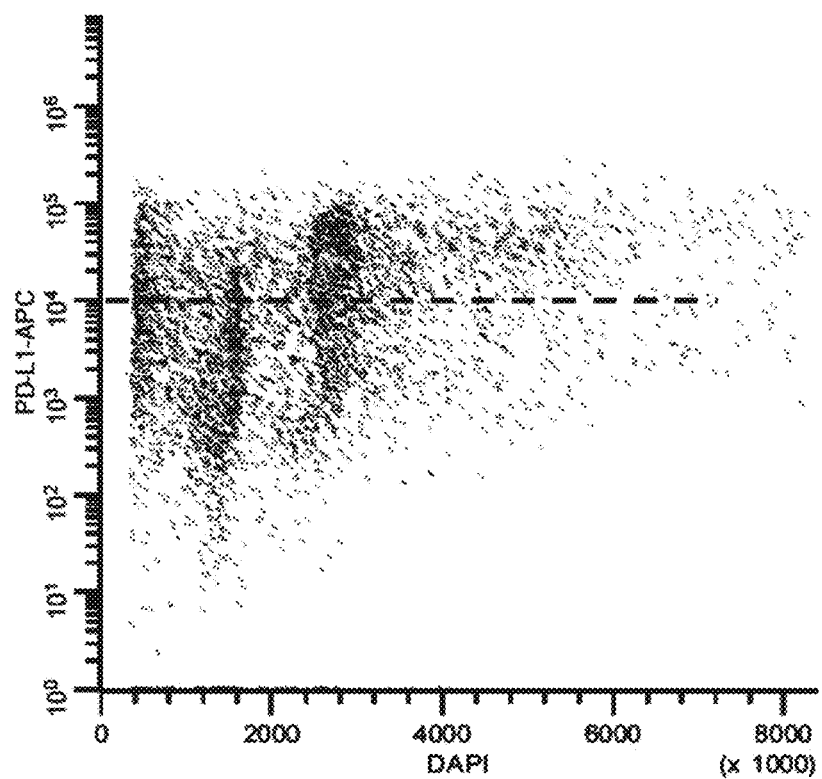
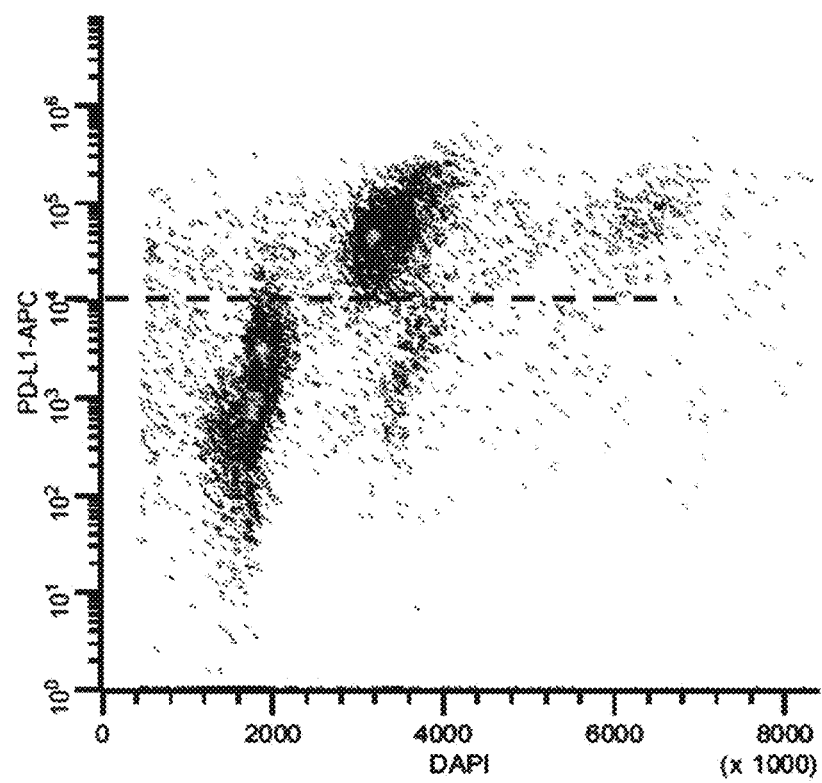
FIG. 9 (cont.)

```
                              SEQUENCE LISTING

Sequence total quantity: 4
SEQ ID NO: 1            moltype = AA  length = 290
FEATURE                 Location/Qualifiers
source                  1..290
                        mol_type = protein
                        organism = Homo sapiens
SEQUENCE: 1
MRIFAVFIFM TYWHLLNAFT VTVPKDLYVV EYGSNMTIEC KFPVEKQLDL AALIVYWEME   60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET            290

SEQ ID NO: 2            moltype = AA  length = 176
FEATURE                 Location/Qualifiers
source                  1..176
                        mol_type = protein
                        organism = Homo sapiens
SEQUENCE: 2
MRIFAVFIFM TYWHLLNAPY NKINQRILVV DPVTSEHELT CQAEGYPKAE VIWTSSDHQV   60
LSGKTTTTNS KREEKLFNVT STLRINTTTN EIFYCTFRRL DPEENHTAEL VIPELPLAHP  120
```

PNERTHLVIL GAILLCLGVA LTFIFRLRKG RMMDVKKCGI QDTNSKKQSD THLEET    176

SEQ ID NO: 3               moltype = DNA   length = 3691
FEATURE                    Location/Qualifiers
source                     1..3691
                           mol_type = unassigned DNA
                           organism = Homo sapiens
SEQUENCE: 3
ggcgcaacgc tgagcagctg gcgcgtcccg cgcggcccca gttctgcgca gcttcccgag    60
gctccgcacc agccgcgctt ctgtccgcct gcagggcatt ccagaaagat gaggatattt   120
gctgtcttta tattcatgac ctactggcat ttgctgaacg catttactgt cacggttccc   180
aaggacctat atgtggtaga gtatggtagc aatatgacaa ttgaatgcaa attcccagta   240
gaaaaacaat tagacctggc tgcactaatt gtctattggg aaatggagga taagaacatt   300
attcaatttg tgcatggaga ggaagacctg aaggttcagc atagtagcta cagacagagg   360
gcccggctgt tgaaggacca gctctccctg gaaatgctg cacttcagat cacagatgtg   420
aaattgcagg atgcaggggt gtaccgctgc atgatcagct atggtggtgc cgactacaag   480
cgaattactg tgaaagtcaa tgccccatac aacaaaatca accaaagaat tttggttgtg   540
gatccagtca cctctgaaca tgaactgaca tgtcaggctg agggctaccc caaggccgaa   600
gtcatctgga caagcagtga ccatcaagtc ctgagtggta agaccaccac caccaattcc   660
aagagagagg agaagctttt caatgtgacc agcacactga gaatcaacac aacaactaat   720
gagattttct actgcacttt taggagatta gatcctgagg aaaaccatac agctgaattg   780
gtcatcccag aactacctct ggcacatcct ccaaatgaaa ggactcactt ggtaattctg   840
ggagccatct tattatgcct tggtgtagca ctgacattca tcttccgttt aagaaaaggg   900
agaatgatga atgtgaaaaa atgtggcatc aagatacaa actcaaagaa gcaaagtgat   960
acacatttgg aggagacgta atccagcatt ggaacttctg atcttcaagc agggattctc  1020
aacctgtggt ttaggggttc atcggggctg agcgtgacaa gaggaaggaa tgggcccgtg  1080
ggatgcaggc aatgtgggac ttaaaaggcc caagcactga aaatgaaacc tggcgaaagc  1140
agaggaggag aatgaagaaa gatggagtca acaggagc ctggagggag accttgatac  1200
tttcaaatgc tgaggggct catcgacgcc tgtgacaggg agaaggata cttctgaaca  1260
aggagcctcc aagcaaatca tccattgctc atcctaggaa gacgggttga gaatccctaa  1320
tttgagggtc agttcctgca gaagtgccct ttgcctccac tcaatgcctc aatttgtttt  1380
ctgcatgact gagagtctca gtgttggaac gggacagtat ttatgtatga gttttcca    1440
tttatttga gtctgtgagg tcttcttgtc atgtgagtgt ggttgtgaat gatttctttt   1500
gaagatatat tgtagtagat gttacaattt tgtcgcaaa ctaaacttgc tcttaatga   1560
tttgctcaca tctagtaaaa catggagtat ttgtaaggtg cttggtctcc tctataacta   1620
caagtataca ttggaagcat aaagatcaaa ccgttggttg cataggatgt caccttttatt  1680
taacccatta atactctggt tgacctaatc ttattctcag acctcaagtg tctgtgcagt  1740
atctgttcca tttaaatatc agctttacaa ttatgtggta gcctacacac ataatctcat  1800
ttcatcgctg taaccaccct gttgtgataa ccactattat tttacccatc gtacagctca  1860
ggaagcaaac agattaagta acttgcccaa accagtaaat agcagacctc agactgccac  1920
ccactgtcct tttataatac aatttacagc tatattttac tttaagcaat tctttttattc  1980
aaaaaccatt tattaagtgc ccttgcaata tcaatcgctg tgccaggcat tgaatctaca   2040
gatgtgagca agacaaagta cctgtcctca aggagctcat agtataatga ggagattaac   2100
aagaaaatgt attattacaa tttagtccaa tgtcatagca taaggatgat gcgagggaa    2160
aacccgagca gtgttgccaa gaggaggaaa taggccaatg tggtctggga cggttggata   2220
tacttaaaca tcttaataat cagagtaatt ttcatttaca aagagaggtc ggtacttaaa   2280
ataaccctga aaaataacac tggaattcct tttctagcat tatattttatt cctgatttgc  2340
ctttgccata taatctaatg cttgtttata tagtgtctgg tattgtttaa cagttctgtc   2400
ttttctattt aaatgccact aaatttttaaa ttcatacctt tccatgattc aaaattcaaa   2460
agatcccatg ggagatggtt ggaaaatctc cacttcatcc tccaagccat tcaagtttcc   2520
tttccagaag caactgctac tgcctttcat tcatatgttc ttctaaagat agtctacatt   2580
tggaaatgta tgttaaaagc acgtattttt aaaattttttt tcctaaatag taacacattg   2640
tatgtctgct gtgtacttttg ctatttttat ttattttagt gtttcttata tagcagatgg   2700
aatgaatttg aagttcccag ggctgaggat ccatgccttc tttgttttcta agttatcttt   2760
cccatagctt ttcattatct ttcatatgat tcagtatatg ttaaatatgt cctacatata   2820
catttagaca accaccattt gttaagtatt tgctctagga cagagtttgg atttgtttat   2880
gtttgctcaa aaggagaccc atgggctctc cagggtgcac tgagtcaatc tagtcctaaa   2940
aagcaatctt attattaact ctgtatgaca gaatcatgtc tggaactttt gttttctgct   3000
ttctgtcaag tataaacttc actttgatgc tgtacttgca aaatcacatt ttctttctgg   3060
aaattccggc agtgtacctt gactgctagc taccctgtgc cagaaaagcc tcattcgttg   3120
tgcttgaacc cttgaatgcc accagctgtc atcactacac agccctccta agaggcttcc   3180
tggaggtttc gagattcaga tgccctggga gatcccagag tttcctttcc ctcttggcca   3240
tattctggtg tcaatgacaa ggagtacctt ggcttgcca catgtcaagg ctgaagaaac    3300
agtgtctcca acagagctcc ttgtgtttatc tgtttgtaca tgtgcatttg tacagtaatt   3360
ggtgtgacag tgttctttgt gtgaattaca gcaagaatt gtggctgagc aaggcacata   3420
gtctactcag tctattccta agtcctaact cctccttgtg gtgttggatt tgtaaggcac   3480
tttatccctt ttgtctcatg tttcatcgta aatggcatag gcagagatga tacctaattc   3540
tgcatttgat tgtcactttt tgtacctgca ttaatttaat aaaatattct tatttatttt   3600
gttacttggt acaccagcat gtccatttttc ttgtttattt tgtgtttaat aaaatgttca   3660
gtttaacatc ccagtggaga aagttaaaaa a                                  3691

SEQ ID NO: 4               moltype = DNA   length = 3349
FEATURE                    Location/Qualifiers
source                     1..3349
                           mol_type = unassigned DNA
                           organism = Homo sapiens
SEQUENCE: 4
ggcgcaacgc tgagcagctg gcgcgtcccg cgcggcccca gttctgcgca gcttcccgag    60
gctccgcacc agccgcgctt ctgtccgcct gcagggcatt ccagaaagat gaggatattt   120

-continued

```
gctgtcttta tattcatgac ctactggcat ttgctgaacg ccccatacaa caaaatcaac    180
caaagaattt tggttgtgga tccagtcacc tctgaacatg aactgacatg tcaggctgag    240
ggctacccca aggccgaagt catctggaca agcagtgacc atcaagtcct gagtggtaag    300
accaccacca ccaattccaa gagagaggag aagcttttca atgtgaccag cacactgaga    360
atcaacacaa caactaatga gattttctac tgcacttttta ggagattaga tcctgaggaa    420
aaccatacag ctgaattggt catcccagaa ctacctctgg cacatcctcc aaatgaaagg    480
actcacttgg taattctggg agccatctta ttatgccttg gtgtagcact gacattcatc    540
ttccgtttaa gaaaagggag aatgatggat gtgaaaaat gtggcatcca agatacaaac     600
tcaaagaagc aaagtgatac acatttggag gagacgtaat ccagcattgg aacttctgat    660
cttcaagcag ggattctcaa cctgtggttt aggggttcat cggggctgag cgtgacaaga    720
ggaaggaatg ggcccgtggg atgcaggcaa tgtgggactt aaaaggccca agcactgaaa    780
atggaacctg gcgaaagcag aggaggagaa tgaagaaaga tggagtcaaa cagggagcct    840
ggagggagac cttgatactt tcaaatgcct gaggggctca tcgacgcctg tgacagggag    900
aaaggatact tctgaacaag gagcctccaa gcaaatcatc cattgctcat cctaggaaga    960
cgggttgaga atccctaatt tgagggtcag ttcctgcaga agtgcccttt gcctccactc   1020
aatgcctcaa tttgttttct gcatgactga gagtctcagt gttggaacgg gacagtattt   1080
atgtatgagt ttttcctatt tattttgagt ctgtgaggtc ttcttgtcat gtgagtgtgg   1140
ttgtgaatga tttctttttga agatatattg tagtagatgt tacaattttg tcgccaaact   1200
aaacttgctg cttaatgatt tgctcacatc tagtaaaaca tggagtattt gtaaggtgct   1260
tggtctcctc tataactaca agtatacatt ggaagcataa agatcaaacc gttggttgca   1320
taggatgtca cctttattta acccattaat actctggttg acctaatctt attctcagac   1380
ctcaagtgtc tgtgcagtat ctgttccatt taaatatcag ctttacaatt atgtggtagc   1440
ctacacacat aatctcattt catcgctgta accaccctgt tgtgataacc actattattt   1500
tacccatcgt acagctgagg aagcaaacag attaagtaac ttgcccaaac cagtaaatag   1560
cagacctcag actgccaccc actgtcctt tataatacaa tttacagcta tattttactt    1620
taagcaattc ttttattcaa aaaccattta ttaagtgccc ttgcaatatc aatcgctgtg   1680
ccaggcattg aatctacaga tgtgagcaag acaaagtacc tgtcctcaag gagctcatag   1740
tataatgagg agattaacaa gaaaatgtat tattacaatt tagtccagtg tcatagcata   1800
aggatgatgc gaggggaaaa cccgagcagt gttgccaaga ggaggaaata ggccaatgtg   1860
gtctgggacg gttggatata cttaaacatc ttaataatca agtaattttt cattttacaaa  1920
gagaggtcgg tacttaaaat aaccctgaaa aataacactg gaattccttt tctagcatta   1980
tatttattcc tgatttgcct ttgccatata atctaatgct tgtttatata gtgtctggta   2040
ttgtttaaca gttctgtctt ttctatttaa atgccactaa attttaaatt catacctttc   2100
catgattcaa aattcaaaag atcccatggg agatggttgg aaaatctcca cttcatcctc   2160
caagccattc aagtttcctt tccagaagca actgctactg cctttcattc atatgttctt   2220
ctaaagatag tctacatttg gaaatgtatg ttaaaagcac gtattttttaa aatttttttc   2280
ctaaatagta acacattgta tgtctgctgt gtactttgct atttttattt atttttagtgt   2340
ttcttatata gcagatggaa tgaatttgaa gttcccaggg ctgaggatcc atgccttctt   2400
tgtttctaag ttatctttcc catagctttt cattatcttt catatgatcc agtatatgtt   2460
aaatatgtcc tacatataca tttagacaac caccatttgt taagtatttg ctctaggaca   2520
gagtttggat ttgtttatgt ttgctcaaaa ggagacccat gggctctcca gggtgcactg   2580
agtcaatcta gtcctaaaaa gcaatcttat tattaactct gtatgacaga atcatgtctg   2640
gaacttttgt tttctgcttt ctgtcaagta taaacttcac tttgatgctg tacttgcaaa   2700
atcacatttt ctttctggaa attccggcag tgtaccttga ctgctagcta ccctgtgcca   2760
gaaaagcctc attcgttgtg cttgaaccct tgaatgccac cagctgtcat cactacacag   2820
ccctcctaag aggcttcctg gaggtttcga gattcagatg ccctgggaga tcccagagtt   2880
tcctttccct cttggccata ttctggttgtc aatgacaagg agtaccttgg ctttgccaca   2940
tgtcaaggct gaagaaacag tgtctccaac agagctcctt gtgttatctg tttgtacatg   3000
tgcatttgta cagtaattgg tgtgacagtg ttctttgtgt gaattacagg caagaattgt   3060
ggctgagcaa ggcacatagt ctactcagtc tattcctaag tcctaactcc tccttgtggt   3120
gttggatttg taaggcactt tatcccttt gtctcatgtt tcatcgtaaa tggcataggg    3180
agagatgata cctaattctg catttgattg tcacttttttg tacctgcatt aattttaataa  3240
aatattctta tttattttgt tacttggtac accagcatgt ccattttctt gtttattttg   3300
tgtttaataa aatgttcagt ttaacatccc agtggagaaa gttaaaaaa               3349
```

METHODS OF ASSAYING NEOPLASTIC AND NEOPLASIA-RELATED CELLS AND USES THEREOF

CROSS-REFERENCE TO RELATED APPLICATIONS

This application is a continuation of U.S. patent application Ser. No. 16/959,355, filed Jun. 30, 2020, now issued as U.S. Pat. No. 11,726,089; which application is a national stage entry of International Application Serial No. PCT/US2019/012074, filed Jan. 2, 2019; which application is a continuation-in-part of U.S. patent application Ser. No. 15/861,352, filed Jan. 3, 2018, now issued as U.S. Pat. No. 10,782,298: which application is a continuation-in-part of International Application Serial No. PCT/US2017/050322, filed Sep. 6, 2017, which application claims priority to the filing date of the U.S. Provisional Patent Application Ser. No. 62/384,037, filed Sep. 6, 2016, the disclosures of which are herein incorporated by reference.

INCORPORATION BY REFERENCE OF SEQUENCE LISTING PROVIDED AS A SEQUENCE LISTING XML FILE

A Sequence Listing is provided herewith as a Sequence Listing XML, "ICDX-011US2CON_SEQ_LIST", created on Sep. 25, 2023, and having a size of 12,063 bytes. The contents of the Sequence Listing XML are incorporated herein by reference in their entirety.

INTRODUCTION

Cancer remains one of the leading causes of death globally, with an estimated 12.7 million annual cases around the world affecting both sexes equally. This number is expected to increase to 21 million by 2030.

The immune system is intimately involved with tumor development, playing a particularly decisive role during disease progression to metastasis. The impact of the immune system on a cancer is not strictly inhibitory as the complex cross talk between immunity and cancer cells also enhances tumor growth. The involvement of the immune system in cancer progression is now generally regarded as a hallmark of cancer. Thus, how the immune system responds to a cancer determines the eventual outcome. Even in cases where a subject's immune system does mount a significant initial response to a cancer, the cancer may still evade the destructive elements of the immune response through various mechanisms including the expression of immune checkpoint proteins to trigger immune suppression. Further mechanisms resulting in evasion of immune attack include the selection of tumor variants resistant to immune effectors (i.e., "immuno-editing") and progressive formation of an immune suppressive environment within the tumor.

Immunotherapies seek to rationally redirect a subject's immune system to effectively target the cancer and/or prevent immune evasion.

SUMMARY

Methods are provided for assaying neoplastic cells and/or neoplasia-related cells. Aspects of the methods involve detecting heterogeneity, per cell programmed-death ligand 1 (PD-L1) expression, and/or proliferation of neoplasia and/or neoplasia-related cells. Aspects of the methods include cytometrically assaying a labeled cell suspension to quantify per cell heterogeneity, per cell PD-L1 expression, proliferation, and/or other parameters to detect whether a neoplastic cell is present in the neoplasia sample. Aspects of the provided methods also include treating a subject based on the outcome of such an assay. In addition, kits that find use in practicing the subject methods are also provided.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 5 provides Table 2.

FIG. 9 depicts PD-L1 expression as a function of DNA content as assayed according to an embodiment of the methods described herein.

DETAILED DESCRIPTION

Figure 1:
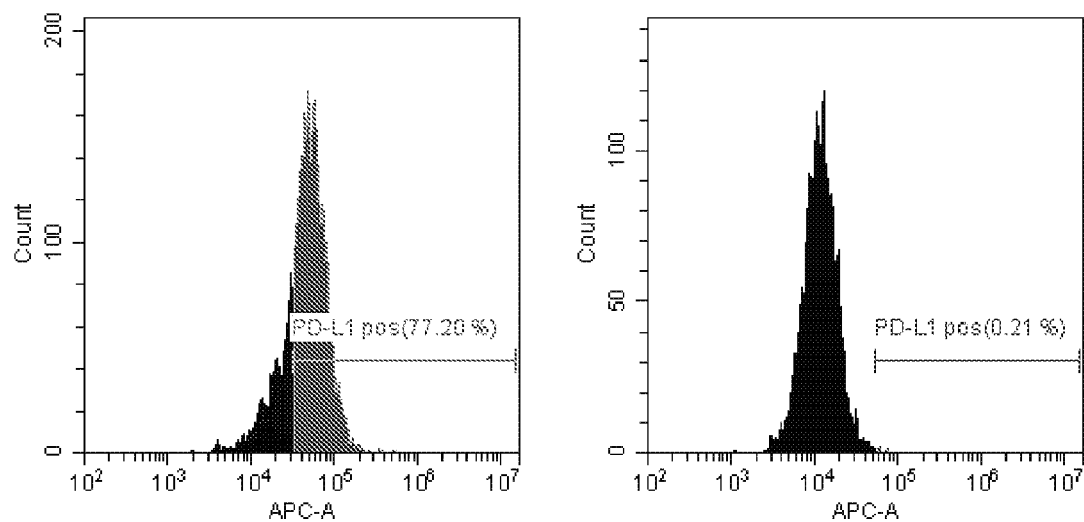
FIG. 1 depicts clear cytometric separation of PD-L1 positive control and negative control cells using PD-L1 labeling and flow cytometric analysis as described herein.

Methods are provided for assaying neoplastic cells and/or neoplasia-related cells. Aspects of the methods involve detecting heterogeneity, per cell programmed-death ligand 1 (PD-L1) expression, and/or proliferation of neoplasia and/or neoplasia-related cells. Aspects of the methods include cytometrically assaying a labeled cell suspension to quantify per cell heterogeneity, per cell PD-L1 expression, proliferation, and/or other parameters to detect whether a neoplastic cell is present in the neoplasia sample. Aspects of the provided methods also include treating a subject based on the outcome of such an assay. In addition, kits that find use in practicing the subject methods are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Methods

As summarized above, methods are provided for detecting neoplastic cells and/or neoplasia-related cells. Neoplastic cells include cells of, or cells derived from, a neoplasia, such as a tumor. Neoplasia-related cells include non-neoplastic cells associated with a neoplasia such as cells that are spatially associated with a neoplasia such as e.g., immune cells, such as tumor infiltrating lymphocytes. Neoplasia cells include cells that may or may not be spatially associated with a neoplasia but are derived from the neoplasia, such as e.g., metastatic cells and/or circulating tumor cells derived from the neoplasia. Methods of the present disclosure may include, in some instances, direct and/or indirect detection of such neoplastic cells and/or neoplasia-related cells.

A cell may by identified as a neoplastic cell using various criteria. For example, in some instances, a cell may be identified as neoplastic, or potentially neoplastic, based on observation of the cellular and/or subcellular morphology of the cell alone or in the context of tissue surrounding the cell. In some instances, a cell behavior may be an indication that a cell is neoplastic, such as but not limited to e.g., proliferation, migration, etc. In some instances, markers, such as but not limited to e.g., proliferation markers, cell surface markers, cancer markers, etc., may be employed to identify a cell as neoplastic. In some instances, assaying gene expression, e.g., expression of a cancer marker, expression of a mutated gene, overexpression, underexpression, etc., may indicate whether a cell is neoplastic.

Correspondingly, a cell may be identified as neoplasia-related according to various criteria. In some instances, a cell may be identified as neoplasia-related based on being spatially associated with a neoplasia but not fulfilling the criteria of a neoplastic cell (i.e., the cell is non-neoplastic). A cell may be identified as non-neoplastic according to various criteria including but not limited to e.g., morphology (e.g., normal morphology), behavior (e.g., proliferatively normal), marker expression (e.g., absence of cancer marker expression), etc. In some instances, a cell may be identified as neoplasia-related based on being spatially associated (i.e., near or within) a neoplasia and being a non-neoplastic cell type such as but not limited to e.g., an immune cell (e.g., a tumor infiltrating lymphocyte), a stromal cell, etc.

Methods of the present disclosure may involve detecting heterogeneity, per cell programmed-death ligand 1 (PD-L1) expression, and/or proliferation of neoplasia cells and/or neoplasia-related cells. In some instances, such methods may include cytometrically assaying a labeled cell suspension to quantify per cell heterogeneity, per cell PD-L1 expression, proliferation, and/or other parameters to detect whether a neoplastic cell is present in a sample and/or a subject based on analyzing a sample obtained from a subject.

As summarized above, embodiments are directed to methods of detecting a cell that expresses programmed-death ligand 1 (PD-L) above a predetermined threshold. Cells in which PD-L1 expression may be detected in the subject methods include, in various instances, neoplastic cells and immune cells. Accordingly, in some instances a cell e.g., a neoplastic cell, detected in the subject methods will have a per cell expression level of PD-L1 protein that exceeds a predetermined threshold.

By "per cell expression level of PD-L1" or "per cell expression of PD-L1", as used herein, is meant the quantity of PD-L1 molecules present on the surface of a cell. Methods of the present disclosure include cytometrically assaying a cellular sample to quantify the per cell expression of PD-L1 and subsequently detecting one or more cells in the sample that have a per cell expression level of PD-L1 protein that exceeds the predetermined threshold. Various means of cytometrically assaying a cellular sample, described in more detail below, may be employed in the subject methods.

PD-L1 Expressing Cells

As summarized above, the present disclosure provides methods of detecting cells expressing PD-L1 above a predetermined threshold. PD-L1 expression may be quantified on a per cell basis based on the level of PD-L1 protein expression or the level of PD-L1 encoding transcript (i.e., mRNA) expression. In some instances, the subject method quantifies only per cell PD-L1 protein expression and does not quantify per cell PD-L1 transcript expression. In some instances, a combined method of quantifying both PD-L1 protein levels and PD-L1 transcription levels may be employed.

As described in more detail below, embodiments of the instant methods may include cytometrically assaying a cell suspension to detect a cell expressing PD-L1 above a predetermined threshold. As used herein, the term "cytometrically assaying" describes the measuring of cellular parameters on a cell-by-cell basis where such measuring allows for the detection of individual cells that have, or the counting of a cell population that shares, a certain cellular parameter or set of parameters. One such parameter that is cytologically assayed in the subject methods is per cell expression of PD-L1.

PD-L1 (also known as CD274) binds programmed cell death protein 1 (PD-1), a protein encoded by the PDCD1 gene that is a cell surface receptor expressed on T-cells. PD-1 functions as an immune checkpoint by preventing the activation of T-cells, which reduces autoimmunity and promotes self-tolerance. PD-L1 has been found to be expressed on a number of different cancer cell types. The presence of PD-L1 on a cancer cell inhibits T cell activation, contributing to cancer cell immune evasion. A number of cancer therapies are directed to preventing cancer cell immune evasion by inhibiting the PD-1/PD-L1 interaction.

The present disclosure includes detecting neoplastic cells expressing PD-L1 above a predetermined threshold. Neoplastic cells having a per cell PD-L1 expression level above a predetermined threshold may be more likely to effectively evade the host immune system. Neoplastic cells having a per cell PD-L1 expression level above a predetermined threshold may be more likely to be affected by therapies directed at disrupting the PD-1/PD-L1 interaction. In some instances, by effectively quantifying PD-L1 expression on the surface of a neoplastic cell and detecting neoplastic cells that express PD-L1 above a threshold level the effectiveness of therapies targeting the PD-1/PD-L1 interaction may be predicted.

The present disclosure includes methods of identifying whether a neoplasia in a subject is anti-PD-1/PD-L1 immunotherapy responsive. As used herein, anti-PD-1/PD-L1 immunotherapy responsive generally refers to the responsiveness of a neoplasia to a treatment targeting the interaction between PD-1 and PD-L1, including e.g., by using an antagonist to PD-1 and/or PD-L1. As such, a cell having a PD-L1 expression level above a predetermined threshold may, in some instances, be referred to as an anti-PD-1/PD-L1 immunotherapy responsive cell. A neoplasia having one or more anti-PD-1/PD-L1 immunotherapy responsive cells may, in some instances, be referred to as an anti-PD-1/PD-L1 immunotherapy responsive neoplasia. The responsiveness of a cell or a neoplasia to an anti-PD-1/PD-L1 immunotherapy may be predicted or determined. For example, in some instances, a method that detects the presence of a cell expressing PD-L1 above a predetermined threshold may be predictive that the neoplasia from which the cell is derived is anti-PD-1/PD-L1 immunotherapy responsive. In some instances, e.g., the presence of a cell expressing PD-L1 above a predetermined threshold positively identifies that the neoplasia from which the cell is derived is anti-PD-1/PD-L1 immunotherapy responsive. The subject methods find use in detecting cells having a level of PD-L1 expression above a predetermined threshold derived from various different neoplasms, described in more detail below.

Cells detected in the methods of the present disclosure will have a level of PD-L1 expression above a predetermined threshold. As such, the methods of the instant disclosure include cytometrically quantifying per cell expression levels of PD-L1 to identify cells expressing PD-L1 protein and/or PD-L1 transcript above a predetermined threshold. Predetermined thresholds for PD-L1 expression useful in the instant disclosure will vary depending on various factors include e.g., the cell type assayed (e.g., the type of neoplasm from which the cell is derived), other measured cellular parameters (e.g., cell cycle parameters, aneuploidy parameters, etc.), and whether PD-L1 protein or transcript are detected. As described in more detail below, PD-L1 expression is determined cytometrically where PD-L1 protein expression may be determined by a variety of protocols including, but not limited to, contacting the cell with a labeled specific binding member that binds PD-L1 protein on the surface of the cell. In some instances, PD-L1 expression is determined cytometrically where PD-L1 transcript expression may be determined by a variety of protocols including, but not limited to, contacting the cell with a labeled specific binding member that binds PD-L1 transcripts within the cell.

In some instances, quantifying per cell PD-L1 expression may include calibrating PD-L1 fluorescence of PD-L1 specific binding partner labeled cells to a reference standard. Depending on the context, a reference standard may be cytometrically assayed in parallel, in series or simultaneously with the assayed cells. For example, in some instances, a reference standard may be cytometrically assayed to calibrate the assay for quantification and then the label cell suspension sample may be assayed using the calibrated cytometric assay. In some instances, a reference standard may be added to (i.e., spiked into) the label cell suspension sample and the calibration based on the reference standard for quantifying the per cell expression of the labeled cells may be performed during cytometric analysis of cells. In some instances, calibration with a reference standard may be performed between or during each run of a labeled cell sample. In some instances, calibration with a reference standard may be performed between or during each batch of runs.

Any convenient reference standard for calibrating labeled cell fluorescence to per cell marker expression may be employed in the herein described assays including but not limited to e.g., standardized microspheres (i.e., beads), standardized control cells, standardized fluorescent particles, and the like. In some instances, spectrally equivalent microsphere standards, such as e.g., Molecules of Equivalent Soluble Fluorochrome (MESF) beads or Mean Equivalent Fluorochrome (MEFL) beads, may be used. Microsphere standards useful in quantitative cytometry will vary any will generally include microspheres labeled with a known amount of fluorophore bound per microsphere or microspheres will a known valency for binding fluorophore labeled molecules. Microsphere standards for quantitative cytometry simulate fluorescent dye attachment to the cell membrane of target cells and allow for calibration of cytometric assays, including e.g., flow cytometric assays or cell cytometric assays, for quantification.

For example, in some instances, microsphere standards for quantitative cytometry will include two or more populations, including e.g., 2 populations, 3 populations, 4 populations, 5 populations, 6 populations, etc., of microspheres labeled with different amounts of a fluorophore. The fluorophore chosen will generally be the same as or equivalent to or comparable with the fluorophore used in one or more of the labeled specific binding members of the described methods. Useful fluorophores in microsphere standards include but are not limited to e.g., Alexa Fluor 488, Alexa Fluor 647, FITC, PE, Cy5, APC, etc. In some instances, two or more microsphere standards having different fluorophores may be mixed, e.g., where quantification of two or more differently labeled specific binding members are used in a subject method. In some instances, microsphere standards having different fluorophores are not mixed and different populations of microspheres having different amounts of a single type of fluorophore bound may be employed.

Microsphere standards may be directly conjugated to the fluorescent label or, in some instances, fluorescently labeled antibody may be bound to the microsphere standard. In some instances, a microsphere standard may be non-fluorescent but "label-able". Label-able microsphere standards will generally have a known antibody binding capacity allowing for staining of the microsphere with a known amount of a user's antibody, including e.g., the same antibody used as a specific binding member in a herein described method. Label-able microsphere standards may, in some instances, be employed in conjunction with a pre-labeled microsphere standard allowing for determination of the fluorophore to protein (FTP) ratio of the particular labeled specific binding member employed in the method and/or further calibration. Various different microsphere standards, including e.g., fluorescently labeled microsphere standards and label-able microsphere standards, for quantitative cytometry that may find use in the herein described methods include but are not limited to e.g., those commercially available from Bangs Laboratories, Inc. (Fishers, IN), BD Biosciences (San Jose, CA), and the like.

In some embodiments, the fluorescence of a labeled specific binding member and/or cells labeled with such may be calibrated to microsphere standards (e.g., by assessing the fluorescence of two or more populations of microspheres labeled with different amounts of a fluorophore) to establish a standard curve. Following or during the establishment of a standard curve a labeled cell suspension sample may be assayed and per cell PD-L1 expression may be determined. Quantified per cell PD-L1 expression levels may be compared to a predetermined threshold, including e.g., a threshold established based on the number of molecules of PD-L1 protein expressed per cell, a threshold established based on background fluorescence, a threshold established based on background expression (including e.g., per cell expression) of PD-L1, and the like.

In some instances, a predetermined threshold for per cell PD-L1 expression may be expressed as a number of molecules of the PD-L1 protein per cell, including but not limited to e.g., a threshold of 10 molecules per cell, a threshold of 20 molecules per cell, a threshold of 30 molecules per cell, a threshold of 40 molecules per cell, a threshold of 50 molecules per cell, a threshold of 60 molecules per cell, a threshold of 70 molecules per cell, a threshold of 80 molecules per cell, a threshold of 90 molecules per cell, a threshold of 100 molecules per cell, a threshold of 200 molecules per cell, a threshold of 300 molecules per cell, a threshold of 400 molecules per cell, a threshold of 500 molecules per cell, a threshold of 600 molecules per cell, a threshold of 700 molecules per cell, a threshold of 800 molecules per cell, a threshold of 900 molecules per cell, a threshold of 1000 molecules per cell, a threshold of 1100 molecules per cell, a threshold of 1200 molecules per cell, a threshold of 1300 molecules per cell, a threshold of 1400 molecules per cell, a threshold of 1500 molecules per cell, a threshold of 1600 molecules per cell, a threshold of 1700 molecules per cell, a threshold of 1800 molecules per cell, a threshold of 1900 molecules per cell, a threshold of 2000 molecules per cell, etc.

Accordingly, in some instances, a cell is detected as expressing PD-L1 above a predetermined threshold if the cell is identified as having a per cell number of PD-L1 protein molecules expressed on the surface of the cell that is above one or more of the predetermined thresholds listed above.

In some instances, the methods described herein detect a single cell having a level of PD-L1 expression above a predetermined threshold. In some instances, the presence of a single detected cell having a level of PD-L1 expression above a predetermined threshold is considered significant. In some instances, the methods described herein may include a threshold of cells having a level of PD-L1 expression above a predetermined threshold for the detected cells to be considered significant (i.e., a minimum size for the population of cells having a level of PD-L1 expression above a predetermined threshold to be considered significant). Depending on the context, the size of the detected population of cells expressing PD-L1 above the threshold will vary and may range from one cell to millions of cells, including but not limited to e.g., one cell, one cell or more, 10 cells or more, 100 cells or more, 1,000 cells or more, 10,000 cells or more, 100,000 cells or more.

In some instances, the size of the detected population of cells expressing PD-L1 above the predetermined threshold may be expressed in relative terms. For example, the size of the population may be expressed as a percentage of all the cells in the sample, a percentage of all the cells analyzed, a percentage of all of the cells of a particular type within the sample, a percentage of all of the cells of a particular type that were analyzed, etc. In some instances, the size of the detected population may exceed 0.01% or more of the neoplastic cells in the cell suspension sample, including but not limited to e.g., 0.1% or more, 1% or more, 10% or more, etc.

In some instances, in order to classify a cell, e.g., a neoplasia cell, as PD-L1 expressing or likely to be anti-PD-1/PD-L1 immunotherapy responsive or detected as anti-PD-1/PD-L1 immunotherapy responsive the size of the population of cells detected as expressing PD-L1 above a predetermined threshold must exceed a predetermined threshold. As described above, the threshold for the size of the detected population, e.g., for a neoplasia to be considered PD-L1 expressing, will vary based on a number of factors and in some instances may be one cell. In some instances, the threshold for the size of the detected population, e.g., for a neoplasia to be considered PD-L1 expressing, the population must exceed more than one cell including two cells or more including but not limited to e.g., 0.01% or more of the neoplastic cells in the sample, 0.1% or more of the neoplastic cells in the sample, 1% or more of the neoplastic cells of the sample, and the like.

Cytometric Assays

As summarized above, methods of the present disclosure include cytometrically assaying a labeled cell suspension. Various methods of cytometrically assaying a labeled cell suspension may find use in the herein described methods including but not limited to e.g., flow cytometrically assaying using a flow cytometer, cell cytometrically assaying a labeled cell suspension, e.g., by using a cell cytometer, and the like. Labeled cell suspension samples may be assayed for per cell PD-L1 expression. In some cases, additional cellular parameters, assayed cytometrically, may also find use in detecting neoplastic cells of the instant disclosure. Accordingly, various methods of cytometrically assaying a labeled cell suspension to measure various cellular parameters may be employed.

In some embodiments, cytometrically assaying a cellular sample may be performed using flow cytometry. Flow cytometry is a methodology using multi-parameter data for identifying and distinguishing between different particle (e.g., cell) types i.e., particles that vary from one another in terms of label (wavelength, intensity), size, etc., in a fluid medium. In flow cytometrically analyzing a sample, an aliquot of the sample is first introduced into the flow path of the flow cytometer. When in the flow path, the cells in the sample are passed substantially one at a time through one or more sensing regions, where each of the cells is exposed separately and individually to a source of light at a single wavelength (or in some instances two or more distinct sources of light) and measurements of cellular parameters, e.g., light scatter parameters, and/or marker parameters, e.g., fluorescent emissions, as desired, are separately recorded for each cell. The data recorded for each cell is analyzed in real time or stored in a data storage and analysis means, such as a computer, for later analysis, as desired.

In flow cytometry-based methods, the cells are passed, in suspension, substantially one at a time in a flow path through one or more sensing regions where in each region each cell is illuminated by an energy source. The energy source may include an illuminator that emits light of a single wavelength, such as that provided by a laser (e.g., He/Ne or argon) or a mercury arc lamp or an LED with appropriate filters. For example, light at 488 nm may be used as a wavelength of emission in a flow cytometer having a single sensing region. For flow cytometers that emit light at two distinct wavelengths, additional wavelengths of emission light may be employed, where specific wavelengths of interest include, but are not limited to: 405 nm, 535 nm, 561 nm, 635 nm, 642 nm, and the like. Following excitation of a labeled specific binding member bound to a polypeptide by an energy source, the excited label emits fluorescence and the quantitative level of the polypeptide on each cell may be detected, by one or more fluorescence detectors, as it passes through the one or more sensing regions.

In flow cytometry, in addition to detecting fluorescent light emitted from cells labeled with fluorescent markers, detectors, e.g., light collectors, such as photomultiplier tubes (or "PMT"), an avalanche photodiode (APD), etc., are also used to record light that passes through each cell (generally referred to as forward light scatter), light that is reflected orthogonal to the direction of the flow of the cells through the sensing region (generally referred to as orthogonal or side light scatter) as the cells pass through the sensing region and is illuminated by the energy source. Each type of data that is obtained, e.g., forward light scatter (or FSC), orthogonal light scatter (SSC), and fluorescence emissions (FL1, FL2, etc.), comprise a separate parameter for each cell (or each "event").

Flow cytometers may further include one or more electrical detectors. In certain embodiments, an electrical detector may be employed for detecting a disturbance caused by a particle or cell passing through an electrical field propagated across an aperture in the path of the particles/cells. Such flow cytometers having electrical detectors will contain a corresponding electrical energy emitting source that propagates an electrical field across the flow path or an aperture through which cells are directed. Any convenient electrical field and/or combination of fields with appropriate detector(s) may be used for the detection and/or measurement of particles (or cells) passing through the field including but not limited to, e.g., a direct current electrical field, alternating current electrical field, a radio-frequency field, and the like.

Flow cytometers further include data acquisition, analysis and recording means, such as a computer, wherein multiple data channels record data from each detector for each cell as it passes through the sensing region. The purpose of the analysis system is to classify and count cells wherein each cell presents itself as a set of digitized parameter values and to accumulate data for the sample as a whole.

A particular cell subpopulation of interest may be analyzed by "gating" based on the data collected for the entire population. To select an appropriate gate, the data is plotted so as to obtain appropriate separation of subpopulations, e.g., by adjusting the configuration of the instrument, including e.g., excitation parameters, collection parameters, compensation parameters, etc. In some instances, this procedure is done by plotting forward light scatter (FSC) vs. side (i.e., orthogonal) light scatter (SSC) on a two dimensional dot plot. The flow cytometer operator then selects the desired subpopulation of cells (i.e., those cells within the gate) and excludes cells which are not within the gate. Where desired, the operator may select the gate by drawing a line around the desired subpopulation using a cursor on a computer screen. Only those cells within the gate are then further analyzed by plotting the other parameters for these cells, such as fluorescence.

Any flow cytometer that is capable of obtaining fluorescence data, e.g., as described above, may be employed. Useful flow cytometers include those utilizing various different means of flowing a cell through the sensing region substantially one at a time including, e.g., a flow cell, a microfluidics chip, etc. Non-limiting examples of flow cytometer systems of interest are those available from commercial suppliers including but not limited to, e.g., Becton-Dickenson (Franklin Lakes, NJ), Life Technologies (Grand Island, NY), Acea Biosciences (San Diego, CA), Beckman-Coulter, Inc. (Indianapolis, IN), Bio-Rad Laboratories, Inc. (Hercules, CA), Cytonome, Inc. (Boston, MA), Amnis Corporation (Seattle, WA), EMD Millipore (Billerica, MA), Sony Biotechnology, Inc. (San Jose, CA), Stratedigm Corporation (San Jose, CA), Union Biometrica, Inc. (Holliston, MA), Cytek Development (Fremont, CA), Propel Labs, Inc. (Fort Collins, CO), Orflow Technologies (Ketchum, ID), handyem inc. (Québec, Canada), Sysmex Corporation (Kobe, Japan), Partec Japan, Inc. (Tsuchiura, Japan), Bay bioscience (Kobe, Japan), Furukawa Electric Co. Ltd. (Tokyo, Japan), On-chip Biotechnologies Co., Ltd (Tokyo, Japan), Apogee Flow Systems Ltd. (Hertfordshire, United Kingdom), and the like.

In some embodiments, cytometrically assaying a cellular sample may be performed using a cell cytometer. As used herein, the term "cell cytometer" (also referred to as an "imaging cytometer" or "automated imaging cytometer") generally refers to an automated or semi-automated cell imaging device capable of imaging cells deposited on or in an imaging vessel to collect data on all or most of the cells of a sample. In cell cytometry, imaging may be performed according to a variety of different methods. In some instances, a cell cytometer may collect a widefield image at low magnification (e.g., 5×, 10×, etc.) of the cells present on or in an imaging vessel to identify the location of the cells and/or screen the cells for a particular parameter (e.g., size, shape, color, fluorescence, etc.). After identifying the location of the cells a cell cytometer may proceed to collect higher magnification (e.g., 20×, 40×, 60×, 100×, etc.) images of all or a portion of the identified cells, e.g., in a targeted manner.

In other instances, a cell cytometer may image cells present on or in an imaging vessel by scanning the imaging vessel. Scanning may be performed at low or high magnification. In some instances, scanning is performed at high magnification to capture images of all or most of the cells. In some instances, scanning is performed at low magnification to identify the location of the cells on or in the imaging vessel. After identifying the location of the cells a cell cytometer may proceed to collect higher magnification images of all or a portion of the identified cells, e.g., in a targeted manner, or may rescan the located cells at high magnification.

The imaging vessels used in cell cytometer systems will vary. In some instances, commonly used laboratory imaging devices such as e.g., microscope slides, may serve as an imaging vessel in a cell cytometer system. In some instances, a cell cytometer imaging vessel may be specifically designed for use with a particular cell cytometer. Useful imaging vessels include but are not limited to e.g., slides (e.g., microscope slides), dishes (e.g., glass bottom imaging dishes), plates (e.g., multi-well imaging plates), etc. Imaging vessels will generally have optical properties amendable to microscopy, e.g., optical clarity, in at least a portion of the vessel. Imaging vessels may or may not have individual compartments. For example, a microscope slide utilized as an imaging vessel does not generally have individual compartments and cells deposited on a slide may be spread about the surface of the slide. Alternatively, a multi-well imaging plate utilized as an imaging vessel does have individual compartments (i.e., wells) into which one or more cells may be deposited.

Cell cytometers include an imaging component such as, e.g., an automated microscope. The imaging component of a cell cytometer may include one or more objectives of various magnification power (e.g., 5×, 10×, 20×, 40×, 60×, 100×, etc.) for collecting light transmitted, reflected or emitted from the object (e.g., cell) being imaged. Light collected by the objective will generally be processed through one or more dichroic mirrors, filters or lenses before being directed to an image capture device.

Suitable image capturing devices may include one or more digital cameras (including color and monochrome cameras) capable of capturing a digital image and a means of storing the digital image and/or transferring the image to attached image processing circuitry or to an attached storage device for later transfer to image processing circuitry. Suitable digital color cameras will vary and will generally include any digital camera (e.g., with one or more CCD or CMOS sensors). Suitable digital cameras include but are not limited to e.g., custom built digital cameras, consumer grade digital color cameras (e.g., consumer grade digital color cameras converted for microscopic use) and those digital microscopy color cameras commercially available from various manufactures including but not limited to e.g., Dino-Eye, Dino-Lite, Jenoptik ProgRes, KoPa, Leica, Motic, Olympus, Omano, OptixCam, PixelLINK, Zeiss, etc.

Cell cytometers further include data acquisition, analysis and recording means, such as a computer, wherein one or more data channels record data from one or more image capture devices for each cell or most of the cells of the imaging vessel. The purpose of the analysis system is to classify and count cells wherein each cell presents itself as a set of digitized parameter values and to accumulate data for the sample as a whole. In some cases, cell cytometers record images of each cell and may be connected to a user interface where such images may be reviewed by a user of the device.

Cell cytometer based methods for detecting cells expressing a particular polypeptide may include contacting the cells of a sample with a fluorescent labeled specific binding member and detecting fluorescently labeled cells by imaging using the cell cytometer. As described in more detail elsewhere herein, the fluorescence of each labeled cell may be cytometrically quantified to identify the per cell expression of a particular polypeptide, e.g., to detect whether a cell expresses the polypeptide above a predetermined threshold.

Any cell cytometer that is capable of obtaining fluorescence data, e.g., as described above, may be employed. Useful cell cytometers include those utilizing various different means of automated cell cytometric imaging to analyze all or most of the cells of a sample. Non-limiting examples of cell cytometer systems of interest are those available from commercial suppliers including but not limited to, e.g., Nexcelom Bioscience LLC (Lawrence, MA), Molecular Devices, LLC (Sunnyvale, CA), Thorlabs Inc. (Newton, New Jersey), TTP Labtech Ltd. (United Kingdom), and the like.

Methods of the instant disclosure include cytometrically quantifying per cell expression levels of particular polypeptides to identify cells expressing the polypeptide above a predetermined threshold. Methods of the instant disclosure may include cytometrically quantifying per cell PD-L1 expression to identify one or more cells expressing PD-L1 above a predetermined threshold. However, the levels of other markers besides PD-L1 may also be assessed in the herein described methods including e.g., cell cycle associated expression products (e.g., cell cycle associated RNAs, cell cycle associated polypeptides, etc.), immune-related expression products (e.g., immune-related RNAs, immune-related polypeptides, etc.), DNA content, etc. Detection of cells having a level of a biomarker, e.g., above or below a predetermined threshold, or not having such other markers may serve to identify further cell parameters useful in the herein described methods.

Predetermined thresholds may find use in identifying cells based on their expression of a particular polypeptide, as described above, or other cellular parameters including but not limited to e.g., cell cycle markers, aneuploidy markers, and the like.

Predetermined thresholds for polypeptide expression useful in the instant disclosure will vary depending on the polypeptide detected and the particular context. In some instances, a predetermined threshold for per cell polypeptide expression may be expressed as a number of molecules of the polypeptide per cell, including but not limited to e.g., a threshold of 10 molecules per cell, a threshold of 20 molecules per cell, a threshold of 30 molecules per cell, a threshold of 40 molecules per cell, a threshold of 50 molecules per cell, a threshold of 60 molecules per cell, a threshold of 70 molecules per cell, a threshold of 80 molecules per cell, a threshold of 90 molecules per cell, a threshold of 100 molecules per cell, a threshold of 200 molecules per cell, a threshold of 300 molecules per cell, a threshold of 400 molecules per cell, a threshold of 500 molecules per cell, a threshold of 600 molecules per cell, a threshold of 700 molecules per cell, a threshold of 800 molecules per cell, a threshold of 900 molecules per cell, a threshold of 1000 molecules per cell, a threshold of 1100 molecules per cell, a threshold of 1200 molecules per cell, a threshold of 1300 molecules per cell, a threshold of 1400 molecules per cell, a threshold of 1500 molecules per cell, a threshold of 1600 molecules per cell, a threshold of 1700 molecules per cell, a threshold of 1800 molecules per cell, a threshold of 1900 molecules per cell, a threshold of 2000 molecules per cell, etc.

In other instances, a predetermined threshold may be a relative level of a marker. Relative levels of a marker may be determined by a variety of means including e.g., determined by making a comparison of the levels of expression of a marker in two separate populations of cells known to differ in their level of the subject marker. For example, a first cell population known to have a high level of Marker X is measured, e.g., on a cytometer, and compared to a second cell population, known to have a low level of Marker X and the comparison is used to determine a threshold level that may be used to categorize cells as either having a low or a high level of Marker X.

Relative levels of a marker may be determined by making a comparison of the levels of marker within a population of cells, e.g., a population of cells of unknown levels of Marker X or a population of cells suspected of containing subpopulations of cells having different levels of Marker X. For example, the level of Marker X is measured on a cytometer of at least a sufficient number of cells such that the measurements may be plotted, e.g., on a histogram, and separation between two or more subpopulations of cells is revealed based on individual cell levels of Marker X. Accordingly, the cytometer operator may then determine a threshold level between the subpopulations that may be used to categorize cells as belonging to a particular subpopulation, e.g., a subpopulation having a low level of Marker X or a subpopulation having high level of Marker X.

In some instances, a threshold may be based on the limit of detection of the cytometer. For example, cells of a population of cells may be identified as having a particular marker (i.e., being positive for a particular marker) if the cells have any detectable level of a particular marker. Likewise, cells of a population of cells may be identified as not having a particular marker (i.e., being negative for a particular marker) if the cells do not have a detectable level of a particular marker. Accordingly, the detection level of the cytometer may be used to determine the marker threshold, as desired.

In some instances, a threshold may be based on previously determined marker levels, e.g., from previously performed control experiments or previously acquired reference expression levels. For example, marker levels determined in previously analyzed samples may be used to determine marker threshold levels. In some instances, marker levels expected of cells obtained from healthy subjects may be used to determine normal marker levels such that a marker threshold that is representative of the normal marker range may be determined. In such instances, marker expression outside, i.e., above or below, the normal marker range is considered to be either above or below the particular marker threshold. In some instances, use of such previously determined marker levels or previously determined threshold levels allows analysis of cells and the identification of cellular subpopulations in the absence of a control or reference cellular sample.

As noted above, methods of the instant disclosure may include assaying cell cycle parameters. Useful cell cycle parameters include but are not limited to e.g., proliferation, cell cycle phase ($G_1$, $G_2$, M,$G_2$-M, S, $G_0$, post $G_1$, and the like), etc. Cell cycle parameters may be assessed on a per cell basis, including e.g., identifying whether a cell is proliferative, identifying the cell cycle phase of a cell, etc. Any convenient means of determining a cell cycle parameter of a cell may be employed in the subject methods. In some instances, a method may not only quantify a particular cell type but also determine whether the quantified cell type is proliferative including e.g., the number or percent of proliferative cells within the quantified cell type. In some instances, a method may not only quantify an immune cell type but also determine whether the quantified immune cell type is proliferative including e.g., the number or percent of proliferative immune cells within the quantified immune cell type. In some instances, a method may determine whether proliferative tumor infiltrating lymphocytes are present and/or the quantity thereof. In some instances, a method may determine whether proliferative CD4+ cells are present and/or the quantity thereof. In some instances, a method may determine whether proliferative CD8+ cells are present and/or the quantity thereof. In some instances, a method may determine the ratio of CD4/CD8 cells and whether the proliferative CD4 and/or CD8 cells are proliferative and/or the quantity thereof.

In some instances, assaying the cell cycle of a cell may include determining the DNA content of the cell (i.e., the per cell DNA content). Various methods may be employed for assaying the cell cycle of a cell by determining the per cell DNA content. In some instances, a DNA labeling reagent (e.g., a nucleic acid dye or stain that contains intrinsic fluorescence) may be employed to label the DNA of the cell and the amount of DNA may be quantified based on the measuring the intensity of the label. Depending on the method of cytometry employed in the method, DNA content may be used to assess cell cycle in various ways. In one embodiment, e.g., regardless of the type of cytometry employed (e.g., flow cytometry, cell cytometry, etc.), the fluorescent intensity of cells labeled with a DNA labeling reagent may analyzed on the cytometer and plotted on a histogram. From the histogram the relative amount of DNA content may be determined for each cell allowing for the identification of the cell cycle phase of each cell. In some instances, such a histogram may represent a cytometric cell cycle profile, also referred to as a cytometric DNA profile.

In some instances, assaying the cell cycle of a cell may include assaying an expressed cell cycle marker (also referred to as a cell cycle biomarker). Expressed cell cycle markers, as used herein, refer to those cellular markers (e.g., cell surface markers and intracellular markers) that are specifically expressed or absent during one or more particular phases of the cell cycle. Accordingly a labeled binding member specific for an expressed cell cycle marker include to those specific binding members that bind components of the cell cycle machinery of the cell. Cell cycle biomarkers may be useful, in some instances, in determining the cell cycle phase of or determining whether or not a cell is proliferative. Cell cycle biomarkers useful in the methods described herein will vary depending on the particular assay and/or the particular cell type and/or cell population to be detected. In some instances, cell cycle biomarkers that may find use in the methods described herein include but are not limited to, e.g., Ki67, cyclin D1, cyclin E, phosphorylated histone H3, and the like.

Expressed cell cycle markers may be detected in various ways. For example, an expressed cell cycle biomarker may be detected at the protein level, e.g., through the use of a labeled specific binding member specific for the cell cycle biomarker protein. In some instances, an expressed cell cycle biomarker may be detected at the RNA level, e.g., through the use of a labeled specific binding member specific for the cell cycle biomarker RNA.

As noted above, methods of the instant disclosure may include assaying aneuploidy. Any convenient method of measuring aneuploidy cytometrically may be employed in the subject methods. In some instances, a cell may be identified as aneuploid based on the measured DNA content of the cell where an aneuploid cell will generally have an abnormally high level of DNA content representing duplication of all or a portion of the cell's genome. Similar methods to those described above for assessing DNA content in regards to cell cycle assessments may be employed for detecting aneuploidy. In some instances, relative DNA content greater than or equal to a threshold DNA content value for a normal cell may indicate that the cell is aneuploid where the threshold may be greater than or equal to ($\geq$) 1.05 times the DNA content of a normal cell including but not limited to, e.g., $\geq$1.06 times, $\geq$1.07 times, $\geq$1.08 times, $\geq$1.09 times, $\geq$1.10 times, $\geq$1.11 times, $\geq$1.12 times and $\geq$1.13 times the DNA content of a normal cell.

In some instances, chromosome specific probes or gene specific probes may be employed to assess aneuploidy. For example, fluorescent in situ hybridization (FISH) using gene specific or chromosome specific probes may be employed to determine the overall ploidy of a cell or to detect the duplication of a particular gene or chromosome. For example, in a diploid organism, the presence of more than two probes for a specific gene or a specific chromosome may indicate that the subject cell is aneuploid.

Ploidy assessments (e.g., assessing the ploidy of a cell, including e.g., whether a cell is aneuploid, diploid, etc.) may be employed in the subject methods for various purposes. For example, in some instances, a ploidy assessment may be employed to determine whether cells of a population are aneuploid or diploid, including e.g., to determine whether a neoplastic cell is aneuploid or diploid, whether an immune cell is aneuploid or diploid, or the like. In some instances, a ploidy assessment may inform other characteristics of the sample and/or the subject, e.g., by a relationship between the ploidy status of a detected cell and other cell types that may be present in the subject. For example, in some instances, the identification of certain aneuploid cells may be indicative and/or predictive of the presence of a neoplastic cell type in a subject other than the detected aneuploid cell type, e.g., the presence of aneuploid immune cells in a tumor tissue of the subject may be indicative of the presence of circulating tumor cells in the subject. In some instances, the presence of aneuploid immune cells in a lung tumor tissue may be indicative of the presence of circulating tumor cells in the subject.

Assessments of cellular parameters may be used in the subject methods to detect cells that have one or more characteristics detected by measuring the described parameters. For example, in some instances, a detected cell may be determined to be an aneuploid cell, e.g., based on one or more assessed aneuploidy parameters of the cell. In some instances, a detected cell may be determined to be a proliferative cell, e.g., based on one or more assessed cell cycle parameters of the cell. Cells may be detected as having a combination of characteristics detected by measuring the described parameters. For example, a cell may be determined to be both proliferative and aneuploid. In addition, the absence of a characteristic may also be used when detecting a particular cell including e.g., where the cell is not proliferative, where the cell is not aneuploid, etc. In some instances, a detected cell may have one characteristic and lack another, e.g., where the cell is proliferative but not aneuploid, where the cell is aneuploid but no proliferative, etc. Any combination of the herein described parameters may find use in the methods of the present disclosure.

As an example, useful combinations of determined parameters may include per cell PD-L1 expression combined with ploidy status, including e.g., where cells or a population of cells are detected that include per cell PD-L1 expression above a predetermined threshold and an aneuploid ploidy status. Useful combinations may also include per cell PD-L1 expression combined with a DNA content or cell cycle determination. In some instances, a heterogeneity index may be employed where such an index is a combination of parameters indicative of the heterogeneity of tumor cells. Useful heterogeneity indexes may include but are not limited to e.g., combinations of cell cycle and/or DNA content parameters combined with, e.g., measurements of cell complexity (e.g., side scatter, SSC) and/or PD-L1 expression measurements. In some instances, a heterogeneity index will include or consist of a combination of cell cycle or DNA content determination, side scatter measurement and PD-L1 quantification, including predetermined thresholds thereof.

In some instances, the methods of the instant disclosure may further include determining whether a subject cell is or is not an immune cell. Various methods may be employed for determining whether a subject cell is or is not an immune cell including e.g., through detecting the presence or absence of one or more immune cell markers, e.g., through contacting the cell with a labeled specific binding member specific for an immune cell marker.

For example, in some instances, a non-immune neoplasia cell may be detected based on expressing PD-L1 above a predetermined threshold and not labeling with an immune cell specific binding member added to the cell suspension. Accordingly, in some instances, the method may further include determining that the identified cell is not an immune cell, e.g., by contacting the cell suspension with one or more labeled specific binding members for immune cells.

Accordingly, in some instances, a cell and/or a population of cells may be identified as being negative for a particular immune cell marker or having a level of expression of an immune cell marker that is below a predetermined threshold indicative that the cell is, in fact, not an immune cell or a particular type of immune cell. Useful immune cell markers, e.g., for identifying a PD-L1 expressing cell as not an immune cell include but are not limited to e.g., CD114, CD117, CD11a, CD11b, CD14, CD15, CD16, CD182, CD19, CD20, CD22, CD24, CD25, CD3, CD30, CD31, CD34, CD38, CD4, CD45, CD56, CD61, CD8, CD91, Foxp3, and the like. Accordingly, in some instances, a detected neoplasia cell may be further characterized as lacking expression of or having expression of below a predetermined threshold of one or more immune cell markers, e.g., as detected using an antibody to an immune cell marker including e.g., those listed above.

In some instances, a cell may be assayed in the herein described methods for expression of a combination of immune cell markers including but not limited to e.g., any combination of the here described markers. For example, in some instances, a PD-L1 expressing cell may be assayed for expression of CD8 and CD45 and may be identified as not being an immune cell when the detected cell is negative for CD8 and CD45 or expresses CD8 and CD45 below a predetermined threshold indicative of the cell not being an immune cell.

In some instances, a cell may be detected based on expressing PD-L1 above a predetermined threshold and labeling with an immune cell specific binding member added to the cell suspension. Accordingly, in some instances, the method may further include determining that the identified cell is an immune cell, e.g., by contacting the cell suspension with one or more labeled specific binding members for immune cells.

Accordingly, in some instances, a cell and/or a population of cells may be identified as being positive for a particular immune cell marker or having a level of expression of an immune cell marker that is above a predetermined threshold indicative that the cell is, in fact, an immune cell or a particular type of immune cell. Useful immune cell markers, e.g., for identifying a PD-L1 expressing cell as an immune cell include but are not limited to e.g., CD114, CD117, CD11a, CD11b, CD14, CD15, CD16, CD182, CD19, CD20, CD22, CD24, CD25, CD3, CD30, CD31, CD34, CD38, CD4, CD45, CD56, CD61, CD8, CD91, Foxp3, and the like. Accordingly, in some instances, a detected cell may be further characterized as having expression of or having expression of above a predetermined threshold of one or more immune cell markers, e.g., as detected using an antibody to an immune cell marker including e.g., those listed above.

In some instances, a cell may be assayed in the herein described methods for expression of a combination of immune cell markers including but not limited to e.g., any combination of the here described markers. For example, in some instances, a PD-L1 expressing cell may be assayed for expression of CD8 and CD45 and may be identified as being an immune cell when the detected cell is positive for CD8 and CD45 or expresses CD8 and CD45 above one or more predetermined thresholds indicative of the cell being an immune cell.

In some instances, the herein described methods may further include assaying one or more markers for circulating tumor cells (CTC), e.g., in order to determine if a detected PD-L1 expressing cell is a CTC. As used herein, the term "CTC" generally refers to those neoplastic cells that have sloughed off of a tumor (e.g., the edge of a tumor) and have been swept away by the bloodstream or lymphatic system thus causing the CTC to circulate in the body. CTC makers include e.g., those markers used in identifying CTCs in the blood stream including but not limited to e.g., Epithelial cell adhesion molecule (EpCAM), cytokeratin 8, cytokeratin 18 and cytokeratin 19. In some instances, CTCs may be further characterized as being negative for one or more immune cell markers, including but not limited to e.g., one or more of those immune cell markers described herein. For example, in some instances, a detected CTC will be negative for CD45.

In some instances, CTCs may be further identified and/or characterized based on the expression of one or more cancer antigens and/or one or more cancer associated antigens. Non-limiting examples of cancer antigens include but are not limited to e.g., CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, and the like. Cancer-associated antigens also include, e.g., 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CN10888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin.

In some instances, methods of the instant disclosure include detecting a cell expressing PD-L1 above a predetermined threshold and further analyzing the cell, e.g., based on detection of one or more of the CTC markers described above, to determine if the cell is a CTC. In some instances, a CTC or a population of CTCs are collected from a sample (e.g., a blood sample of a subject) and the CTC or population of CTCs are assayed according to the methods described herein, e.g., to determine if the CTC or CTCs of the population express PD-L1 above a predetermined threshold.

In some instances, methods of the instant disclosure may indirectly detect and/or predict the presence of CTCs based on one or more cytometrically assayed parameters. For example, in some instances, the presence or absence of CTCs may be indirectly detected or predicted based on the measured ploidy status of cells of the sample, including e.g., the measured ploidy status of neoplastic cells of the sample. In some instances, the presence or absence of CTCs may be indirectly detected or predicted based on the measured proliferative state of cells of the sample, including e.g., the measured proliferative state of neoplastic cells of the sample. The methods may include a step of assigning an assayed sample as containing one or more CTCs, such that it is labeled or identified as a CTC containing sample. Depending on the sample employed, in some instances, a method of the present disclosure may identify a sample as a CTC containing sample or a subject from which the subject was contained as a CTC containing subject. For example, in some instances, the methods may include a step of assigning a subject, from which an assayed sample was obtained, as having one or more CTCs, such that the subject is labeled or identified as a CTC containing subject.

In such methods, the actual presence and/or amount of CTCs may or may not be determined. Correspondingly, a sample assayed for indirect detection of CTCs may or may not include CTCs. For example, where an assayed sample is obtained directly from a tissue that does not contain CTCs or would not be expected to contain CTCs, the assay may identify a subject as having CTCs, e.g., based on the one or more cytometrically assayed parameters of the cells of the sample, without CTCs actually being present in the sample. As an example of this, a sample may be obtained from a non-hematological tissue (e.g., a non-hematological tumor) and the subject may be identified as containing CTCs, e.g., in their blood system, based on cytometrically assayed parameters of the cells of the non-hematological tissue. In some embodiments, where an assayed sample is obtained directly from a tissue that may contain CTCs, the assay may identify a subject and/or the sample as having CTCs, e.g., based on the one or more cytometrically assayed parameters of the cells of the sample, without directly detecting the CTCs in the sample. As an example of this, a sample may be obtained from a hematological tissue (e.g., blood) and the subject and/or the hematological sample may be identified as containing CTCs or the subject may be identified as containing CTCs, e.g., in their blood system, based on cytometrically assayed parameters of cells of the hematological tissue other than CTCs.

Methods of the present disclosure may thus include one or more steps of assigning, labeling or identifying an assayed sample as containing one or more cell populations, such assigning, labeling or identifying the sample as a CTC containing sample. Methods of the present disclosure may also include one or more steps of assigning, labeling or identifying a subject from which an assayed sample was obtained as containing one or more cell populations, such assigning, labeling or identifying the subject as a CTC containing subject. Such steps may be useful for a variety of purposes, including e.g., providing useful information as to: the type of treatment(s) that may be applied to a subject, the duration of treatment(s) that may be applied to a subject, the need for follow-up assays to be performed and/or when such follow-up may be performed, the need to further test the sample (e.g., to directly assay for CTCs), and the like. For example, in some instances, a method may indirectly detect or predict the presence and/or prevalence of CTCs in a subject (e.g., by assigning a sample obtained from the subject as being a CTC containing sample), as determined by assaying a sample from the subject, without directly detecting and/or otherwise measuring CTCs in the sample or the subject or a separate sample collected from the subject. Following such a method, in some instances, the subject and/or the sample may be labeled as containing CTCs and further appropriate procedures, such as further testing and/or treatment may be identified and/or performed.

Methods of the instant disclosure include the detection of a cell expressing PD-L1 above a predetermined threshold. In some instances, the instant methods may encompass the detection of a plurality of cells expressing PD-L1 above the predetermined threshold. For example, in some instances, the size of a population of cells expressing PD-L1 above the predetermined threshold may be determined. Quantification of the size of a population of cells expressing PD-L1 above the predetermined threshold may be measured cytometrically. For example, in some instances, a flow cytometer may be used to count the number of cells that express PD-L1 above a predetermined threshold. In some instances, a cell cytometer may be used to count the number of cells that express PD-L1 above a predetermined threshold. By counting the number of cells the size of the PD-L1 expressing population may be determined.

Samples

As summarized above, methods of the instant disclosure include detecting whether a neoplastic cell that expresses PD-L1 above a predetermined threshold is present in a neoplasia sample. The herein described methods are applicable to various neoplasia samples where a neoplasia sample may include a sample of any neoplastic (i.e., abnormally growing) tissue or cell population or cell. Abnormal tissue growth may be determined by a variety of means including e.g., by comparing the growth of the subject tissue to the growth of an appropriate normal or healthy tissue. Neoplasms include benign neoplasms, in situ neoplasms, malignant neoplasms, and neoplasms of uncertain or unknown behavior. Malignant neoplasms include cancer and accordingly the subject methods may include detecting whether a cancer cell that expresses PD-L1 above a predetermined threshold is present in a cancer sample.

The methods described herein find use in detecting whether a neoplastic cell that expresses PD-L1 above a predetermined threshold is present in a variety of different neoplasia samples including e.g., samples obtained from various cancers, including but not limited to e.g., Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, ect.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sézary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenström Macroglobulinemia, Wilms Tumor, and the like.

Samples useful in the herein described methods may be samples obtained from a primary tumor, e.g., from a biopsy or surgical resection, or a non-tumor tissue. Non-tumor tissues may be assessed to for various reasons including but not limited to for cancer surveillance. For example, in some instances a non-tumor tissue may be assayed to detect a cell of a neoplasia expressing PD-L1 above a predetermined threshold therefore identifying the presence of the neoplasia. Both solid and fluid non-tumor samples may be assessed. Useful solid tissues that may be assessed include but are not limited to e.g., tissue adjacent to an existing cancer (e.g., skin tissue, lung tissue, breast tissue, etc.), lymph node tissue, etc. Useful fluid samples that may be assessed include essentially any bodily fluid sample including but are not limited to e.g., blood samples, lymph fluid samples, etc.

Cancer and tumor tissues that may be assessed likewise include solid and liquid samples. For example, in the case of a hematopoietic cancer a blood sample or a bone marrow sample may be assessed. In some instances, the sample assessed according to the herein described methods is a solid tumor sample. Solid tumor samples may be obtained from a variety of different cancers, including e.g., any of those cancers listed above. In some instances, a solid tumor sample may be a cancer of an epithelial tissue or an epithelial cancer.

Epithelial cancers include carcinomas. Non-limiting examples of carcinomas include acinar carcinoma, acinic cell carcinoma, acinous carcinoma, adenocystic carcinoma, adenoid cystic carcinoma, adenosquamous carcinoma, adnexal carcinoma, adrenocortical carcinoma, alveolar carcinoma, ameloblastic carcinoma, apocrine carcinoma, basal cell carcinoma, bronchioloalveolar carcinoma, bronchogenic carcinoma, cholangiocellular carcinoma, chorionic carcinoma, clear cell carcinoma, colloid carcinoma, cribriform carcinoma, ductal carcinoma in situ, embryonal carcinoma, carcinoma en cuirasse, endometrioid carcinoma, epidermoid carcinoma, carcinoma ex mixed tumor, carcinoma ex pleomorphic adenoma, follicular carcinoma of thyroid gland, hepatocellular carcinoma, carcinoma in si'tu, intraductal carcinoma, Hürthle cell carcinoma, inflammatory carcinoma of the breast, large cell carcinoma, invasive lobular carcinoma, lobular carcinoma, lobular carcinoma in situ (LCIS), medullary carcinoma, meningeal carcinoma, Merkel cell carcinoma, mucinous carcinoma, mucoepidermoid carcinoma, nasopharyngeal carcinoma, non-small cell carcinoma, non-small cell lung carcinoma (NSCLC), oat cell carcinoma, papillary carcinoma, renal cell carcinoma, scirrhous carcinoma, sebaceous carcinoma, carcinoma simplex, signet-ring cell carcinoma, small cell carcinoma, small cell lung carcinoma, spindle cell carcinoma, squamous cell carcinoma, terminal duct carcinoma, transitional cell carcinoma, tubular carcinoma, verrucous carcinoma, and the like.

In some instances, the methods described herein find use in detecting whether a neoplastic cell that expresses PD-L1 above a predetermined threshold is present in an epithelial tumor sample, including e.g., an epithelial lung cancer tumor, an epithelial breast cancer tumor, etc. In some instances, the methods described herein find use in detecting whether a neoplastic cell that expresses PD-L1 above a predetermined threshold is present in a non-small cell lung cancer (NSCLC) tumor. In some instances, the epithelial tumor is a squamous cell carcinoma, an adenocarcinoma or an adenosquamous and the detected cell(s) include squamous cell carcinoma cells, adenocarcinoma cells or adenosquamous carcinoma cells.

In some instances, the herein described methods may be performed on a neoplasia sample that has been previously identified as PD-L1 positive. In some instances, the herein described methods may be performed on a neoplasia sample that are generally considered to or expected to express PD-L1. Tumors that have been previously shown to express PD-L1 include but are not limited to e.g., renal cell carcinoma (RCC), melanoma, ovarian cancer, NSCLC, etc. In some instances, a neoplasia sample may have been previously identified as PD-L1 positive by immunohistochemistry (IHC). PD-L1 IHC as a companion diagnostic to therapy has been problematic in determining which patients will be responsive to therapy. Issues with PD-L1 IHC include subjectivity of the reviewer, processing variability, differences in semi-quantitative cut offs, variability in staining of tumor cells, staining of immune cells, staining of stromal cells, etc. In some instances, the methods described herein may be utilized to validate the results of a previous PD-L1 IHC assay. In some instances, the herein described methods may be used in place of a PD-L1 IHC assay as the method of the instant disclosure do not suffer from the issues associated with PD-L1 IHC.

Neoplasia samples containing neoplasia cells may be obtained using any convenient sample collection method, including but not limited to those biopsy methods for obtaining solid tissue biopsies and biopsy aspirates. In some instances, a sample containing neoplastic cells may be obtained as part of a separate medical procedure performed for a purpose other than obtaining the sample, including but not limited to a surgical procedure. In other instances, a sample containing neoplastic cells may be obtained independently, e.g., not as part of a separate medical procedure. Sample collection methods will vary and will depend upon, e.g., whether the collection is or is not performed as part of an additional medical procedure, the particular type of sample to be obtained, the primary purpose for obtaining the sample and/or the method by which the sample is to be processed and/or analyzed.

Samples used in the methods of the present disclosure may be collected by any convenient means. In some instances, a neoplasia sample is prepared from a biopsy. Depending on the type of cancer and/or the type of biopsy performed the sample may be prepared from a solid tissue biopsy or a liquid biopsy.

In some instances, a sample may be prepared from a surgical biopsy. Any convenient and appropriate technique for surgical biopsy may be utilized for collection of a sample to be assessed according to the methods described herein including but not limited to, e.g., excisional biopsy, incisional biopsy, wire localization biopsy, and the like. In some instances, a surgical biopsy may be obtained as a part of a surgical procedure which has a primary purpose other than obtaining the sample, e.g., including but not limited to tumor resection, mastectomy, lymph node surgery, axillary lymph node dissection, sentinel lymph node surgery, and the like.

In some instances, a sample may be obtained by a needle biopsy. Any convenient and appropriate technique for needle biopsy may be utilized for collection of a sample to be analyzed according to the methods described herein including but not limited to, e.g., fine needle aspiration (FNA), core needle biopsy, stereotactic core biopsy, vacuum assisted biopsy, and the like.

FNA biopsy may be performed on both palpable and non-palpable lesions and involves the introduction of a small-gauge needle, e.g., ranging from 18 to 25 gauge, into the mass or suspected area and the extraction of cellular material. Whether FNA is performed with or without co-imaging may vary and will depend on various factors including whether the lesion is palpable. In instances where FNA is performed with co-imaging the technique may be referred to as image-guided FNA and may include but is not limited to radiological imaging techniques such as ultrasound, computed tomography (CT), fluoroscopy, mammography, MRI, and the like. FNA techniques, and variations thereof, useful in collecting samples as described herein will vary and selection of specific techniques will depend on various factors including but not limited to, e.g., the characteristics of the subject, the characteristics of the particular detected lesion, the analysis procedure, etc. Variations of such FNA techniques include but are not limited to, e.g., the open-ended needle (i.e., the "French technique"), the negative pressure technique, imaging-guided FNA, and the like. As such, particular FNA techniques may or may not include negative suction. For example, in the French technique FNA short, rapid strokes within the lesion cause dislodgement of cells and allow effective collection within the needle via capillary action without the need for negative suction. In some instances, e.g., when excess fluid (e.g., of a cystic lesion), a syringe with plunger removed may be employed in collecting a sample by FNA. In some instances, negative pressure may be utilized to draw the sample into a syringe. In some instances, a syringe holder or aspiration gun or aspiration handle may be used.

Core needle biopsy may be performed on both palpable and non-palpable lesions and involves the introduction of a hollow core needle into the mass or suspected area and the extraction of cellular material. Whether core needle biopsy is performed with or without co-imaging may vary and will depend on various factors including whether the lesion is palpable. In instances where core needle biopsy is performed with co-imaging the technique may be referred to as image-guided core needle biopsy or stereotactic core needle biopsy and may include but is not limited to radiological imaging techniques such as ultrasound, computed tomography (CT), fluoroscopy, mammography, MRI, and the like. Variations of such core needle biopsy techniques include but are not limited to, e.g., vacuum-assisted core biopsy, imaging-guided core biopsy, and the like. As such, particular core needle biopsy techniques may or may not include an incision made in the skin prior to insertion of the core biopsy needle. For example, in the vacuum-assisted core biopsy a small cut is made and a hollow probe is put through the cut and guided to the lesion site and then a cylinder of tissue is then pulled into the probe by vacuum pressure. In general, a core needle biopsy obtains more tissue than the described FNA technique.

In some instances, the term "needle biopsy" may generally refer any biopsy which can be performed without anesthesia or may require only local anesthesia and which are not considered surgical procedures. In some instances, such biopsies may utilize devices other than "needles" such as, but not limited to, those devices that may be utilized to obtain a punch biopsy, e.g., a skin punch biopsy. Such devices include but are not limited to, e.g., those devices used in the collection of skin punch biopsies.

According to the particular biopsy method employed and depending on the specifics of a particular subject and/or a subject's particular lesion one biopsy or multiple biopsies may be performed. For example, in some instances, a single biopsy, e.g., a single FNA biopsy or a single core needle biopsy, may be performed to sufficiently sample a particular subject or a particular subject's lesion. In other instances, multiple biopsies, e.g., multiple FNA biopsies or multiple core needle biopsies, may be performed for the collection of a single sample or multiple samples from a subject or a subject's lesion. In instances where multiple biopsies are collected the actual number of biopsies will vary depending on the particular subject and/or the particular lesion or lesions of the subject and, as such, may range from 2 to 10 or more biopsies, including but not limited to, e.g., 2 biopsies, 3 biopsies, 4 biopsies, 5 biopsies, 6 biopsies, 7 biopsies, 8 biopsies, 9 biopsies, 10 biopsies, etc. Multiple biopsies may be collected in a co-timely manner or may be collected over a pre-determined period of time, e.g., as part of a surveillance protocol.

Neoplasia samples collected according to the methods described herein may be solid, semi-solid, or liquid samples. For example, in some instances, by nature of the collection technique utilized, e.g., techniques that cause the dissociation or aspiration of cells, the collected sample may be a liquid sample upon collection. In other instances, by nature of the collection technique utilized, e.g., surgical collection or core sample collection, the collected sample may be a solid or semi-solid sample upon collection. In embodiments where the collected sample is a solid or semi-solid sample the cells of the sample may be dissociated to form a liquid sample following collection. Methods of dissociating solid and semi-solid tissue samples include but are not limited to mechanical dissociation, chemical dissociation, enzymatic dissociation, and combinations thereof.

In some instances, solid tumor samples may be subjected to mechanical homogenization. Any convenient method of mechanical homogenization may find use preparing a solid tissue sample for downstream steps including but not limited homogenization performed using a commercially available homogenization device including e.g., those available from IncellDx (Menlo Park, CA), such as e.g., those provided with the incellPREP (IncellDx, Inc) kit, Claremont BioSolutions (Upland, CA) including e.g., the microHomogenizer (Claremont BioSolutions), the microDisruptor (Claremont BioSolutions), and the like. Mechanical homogenization may be performed in any suitable solution, including e.g., a buffer. In some instances, mechanical homogenization may be combined with chemical or enzymatic homogenization. In some instances, a fixation reagent is added during homogenization. In some instances, a fixation reagent is added following, including immediately following, homogenization. Fixation reagents, described in more detail below, that may be added following homogenization include but are not limited to e.g., the incellPREP (IncellDx, Inc). In some instances, a fixation solution may be a combination fixation/permeabilization reagent.

In some instances, the fixative used in preparing the labeled cell suspension sample provides for the ability to cytometrically separate PD-L1 expressing cell from PD-L1 non-expressing cells, including but not limited to e.g., to effectively cytometrically separate cells having a per cell PD-L1 expression level above a predetermined threshold from those having a per cell PD-L1 expression level below the predetermined threshold.

Upon collection or preparation of the sample, e.g., dissociation or homogenization, the cells of the resultant liquid cell suspension of may be fixed and/or permeabilized as desired. As such, aspects of the methods may include fixing the cells of the suspension by contacting the sample with a suitable fixation reagent. Fixation reagents of interest are those that fix the cells at a desired time-point. Any convenient fixation reagent may be employed, where suitable fixation reagents include, but are not limited to mildly cross-linking agents. In some instances, a mildly cross-linking agent may be a formaldehyde-based fixative including but not limited to e.g., formaldehyde, paraformaldehyde, formaldehyde/acetone, IncellFP (IncellDx, Inc), etc. In some instances, an alcohol-based fixative may be employed including but not limited to e.g., methanol/acetone, ethanol, etc. In some instances, formaldehyde-based fixatives may be used at a final concentration of about 1 to 2%.

In some instances, the cells in the sample are permeabilized by contacting the cells with a permeabilizing reagent. Permeabilizing reagents of interest are reagents that allow the labeled biomarker probes, e.g., as described in greater detail below, to access to the intracellular environment. Any convenient permeabilizing reagent may be employed, where suitable reagents include, but are not limited to: mild detergents, such as Triton X-100, NP-40, saponin, etc.; methanol, and the like.

Samples used in the methods of the present disclosure are assayed cytometrically. Accordingly, in some instances, a neoplasia sample may be processed to generate a cell suspension suitable for cytometric assays. Processing to generate sample suitable for cytometric assays may include e.g., any individual step or combination of the steps described above including e.g., homogenization, dissociation, fixation, permeabilization, etc. The amount of processing required will depend on various factors including the source of the sample where solid tissue samples will generally require more processing that a liquid sample. For example, processing of a liquid sample, e.g., hematopoietic sample, may not require homogenization or dissociation and thus may only require fixation and/or permeabilization as desired.

The cells of a cell suspension sample will generally be labeled with one or more labeled specific binding members. For example, methods of the present disclosure will generally include contacting a cell suspension sample with a labeled specific binding member specific for PD-L1. Other specific binding members and other labeling reagents may find use in the subject methods for labeling various aspects of a cell or cells of a population as described herein including but not limited to e.g., a maker (e.g., an immune cell marker), the nucleus of the cell, etc. Such regents are described in more detail below.

Contacting, e.g., contacting a cell of a cell suspension with a specific binding member may be carried out by any convenient and appropriate means. In some instances, a cell of a cell suspension may be contacted with a specific binding member by adding an aliquot of the specific binding member to the cell suspension. A contacted cell suspension may be incubated and/or post-fixed as desired.

Reagents

A summarized above, the instant methods include the detection of a cell expressing a per cell level of PD-L1 above a predetermined threshold and thus include various reagents useful in practicing the methods. For example, the instant methods generally include detecting a cell expressing PD-L1 above a predetermined threshold by contacting the cell with a labeled specific binding member reagent in order to allow cytometric assays to be performed.

In order to effectively cytometrically quantify the per cell level of a particular polypeptide a direct correlation between the amount of fluorescence measured from the labeled specific binding member and the number of polypeptides bound by the specific binding member may be desired. In some instances, the amount of fluorescence emitted by the labeled specific binding member is linearly correlated to the number of polypeptides bound by the labeled specific binding member. Generally, but not exclusively, a labeled specific binding member will bind one molecule of the target polypeptide. As such, in some instances, there may be a one-to-one correlation between the amount of fluorescence detected from a plurality of labeled specific binding members bound to polypeptides on the surface of a cell and the number of the polypeptides expressed by the cell. Accordingly, in instances where per cell expression of a polypeptide is quantified cytometrically, the labeled specific binding members used may all uniformly have the same amount of attached label such that each specific binding member emits essentially the same amount of fluorescence. For example, a labeled specific binding member may have a single attached label or a single fluorescent moiety. Alternatively, a labeled specific binding member may have a plurality of attached label (e.g., 2 attached labels, 3 attached labels, 4 attached labels, etc.) or a plurality of fluorescent moieties (e.g., 2 moieties, 3 moieties, 4 moieties, etc.) provided the plurality is the same for each molecule of labeled specific binding member.

Specific binding agents of interest include antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'$_2$ fragments. Also within the scope of the term "antibody binding agent"

are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. Nucleic acid binding agents of interest are nucleic acids that specifically bind or specifically hybridize to biomarker nucleic acids in a cell. The length of these nucleic acids may vary, so long as it is sufficient for the oligonucleotide to serve as a specific binding agent, and in some instances ranges from 13 to 100 nt, such as 14 to 50 nt, e.g., 15 to 25 nt, including but not limited to, e.g., 15 nt, 16 nt, 17 nt, 18 nt, 19 nt, 20 nt, 21 nt, 22 nt, 23 nt, 24 nt, and 25 nt. The oligonucleotides that make up these nucleic acid binding agents may be DNA or RNA, or a synthetic analogue thereof, as desired.

As described above, the specific binding members described herein will generally be detectably labeled (i.e., have an attached detectable label, be bound by a detectable label, etc.). Therefore, in addition to a specific binding domain that specifically binds or specifically hybridizes to the biomarker of interest, the specific binding agent may further include or may be bound by or attached to a detectable label. Of interest as detectable labels are fluorescent dyes. Fluorescent dyes (fluorophores) can be selected from any of the many dyes suitable for use in imaging applications (e.g., fluorescent microscopy) and cytometry applications. A large number of dyes are commercially available from a variety of sources, such as, for example, Molecular Probes (Eugene, OR) and Exciton (Dayton, OH). Examples of fluorophores of interest include, but are not limited to, 4-acetamido-4'-isothiocyanatostilbene-2,2'disulfonic acid; acridine and derivatives such as acridine, acridine orange, acridine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumarin 151); cyanine and derivatives such as cyanosine, Cy3, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo) benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, OR) and Exciton (Dayton, OH).

The methods of the present disclosure generally include the use of a labeled binding member specific of PD-L1 (i.e., a labeled PD-L1 specific binding member) to label cells of the cell suspension thus generating a labeled cell suspension that may be cytometrically assayed. As described above, depending on the context, a labeled binding member specific for PD-L1 may specifically bind PD-L1 protein or may specifically bind PD-L1 transcript.

In some instances, a labeled binding member specific for PD-L1 protein may specifically bind PD-L1 protein expressed on the surface of a cell. Human PD-L1 protein is a 290 amino acid polypeptide having a signal peptide domain from residue 1 to about residue 18, an extracellular topological domain from about residue 19 to about residue 238, a transmembrane domain from about residue 239 to about residue 259, and a cytoplasmic topological domain from about residue 260 to 290. The primary isoform of human PD-L1 (programmed cell death 1 ligand 1 isoform a precursor NP_054862.1) has the following amino acid sequence:

(SEQ ID NO: 1)
MRIFAVFIFMTYWHLLNAFTVTVPKDLYVVEYGSNMTIECKFPVEKQL

DLAALIVYWEMEDKNIIQFVHGEEDLKVQHSSYRQRARLLKDQLSLGN

AALQITDVKLQDAGVYRCMISYGGADYKRITVKVNAPYNKINQRILVV

DPVTSEHELTCQAEGYPKAEVIWTSSDHQVLSGKTTTTNSKREEKLFN

VTSTLRINTTTNEIFYCTFRRLDPEENHTAELVIPELPLAHPPNERTH

LVILGAILLCLGVALTFIFRLRKGRMMDVKKCGIQDTNSKKQSDTHLE

ET.

Human PD-L1 also has a minor alternatively spliced isoform (programmed cell death 1 ligand 1 isoform b precursor NP_001254635.1) having the following amino acid sequence:

(SEQ ID NO: 2)
MRIFAVFIFMTYWHLLNAPYNKINQRILVVDPVTSEHELTCQAEGYPK

AEVIWTSSDHQVLSGKTTTTNSKREEKLFNVTSTLRINTTTNEIFYCT

FRRLDPEENHTAELVIPELPLAHPPNERTHLVILGAILLCLGVALTFI

FRLRKGRMMDVKKCGIQDTNSKKQSDTHLEET.

Useful specific binding members specific for PD-L1 protein include but are not limited to antibodies, including but not limited to antibodies that bind one or both of the above human PD-L1 isoforms, the sequences of which are provided. In some instances, anti-PD-L1 (i.e., anti-CD274)

antibodies that are directly conjugated to a fluorophore may find use in the described methods. Useful commercially available directly conjugated anti-PD-L1 antibodies include but are not limited to e.g., those listed in Table 1 below.

TABLE 1

| Commercial Supplier | Antibody | Fluor. Conjugation |
|---|---|---|
| Acris Antibodies GmbH | Anti-human CD274/PDL1 | FITC, PE |
| Acris Antibodies GmbH | Anti-mouse CD274/PDL1 | FITC |
| Novus Biologicals | Goat Polyclonal Anti-Mouse B7-H1/PD-L1/CD274 Antibody | Allophycocyanin, Fluorescein |
| Novus Biologicals | Mouse Monoclonal Anti-Human B7-H1/PD-L1/CD274 Antibody | Phycoerythrin, Alexa Fluor 700, Alexa Fluor 647, Alexa Fluor 594, Alexa Fluor 405, Allophycocyanin, PerCP, Phycoerythrin, Alexa Fluor 488, Alexa Fluor 350, Alexa Fluor 750 |
| Novus Biologicals | Rat Monoclonal Anti-Human/Mouse B7-H1/PD-L1/CD274 Antibody | PerCP, Alexa Fluor 647, Alexa Fluor 594, DyLight 488, Alexa Fluor 405, Alexa Fluor 488, Alexa Fluor 647, Alexa Fluor 700, DyLight 755, DyLight 350, PE, DyLight 680, Allophycocyanin, DyLight 405, DyLight 405LS |
| R & D Systems | Anti-Mouse B7-H1/PD-L1 Antibody | Allophycocyanin, Fluorescein, Alexa Fluor 594, Alexa Fluor 647 |
| R & D Systems | Anti-Human B7-H1/PD-L1 Antibody | Allophycocyanin, Alexa Fluor 405, Alexa Fluor 488, Alexa Fluor 594, Alexa Fluor 647, Alexa Fluor 700, Phycoerythrin, PerCP |
| Bio-Rad (Formerly AbD Serotec) | Rat anti-mouse CD274 Antibody | FITC, Alexa Fluor 488, Alexa Fluor 647 |
| Bio-Rad (Formerly AbD Serotec) | Mouse anti-human CD274 Antibody | Alexa Fluor 488, Alexa Fluor 647, FITC, RPE |
| GeneTex | Anti-human PD-L1 antibody | FITC, Phycoerythrin (PE) |
| Gene Tex | Anti-mouse PD-L1 antibody | FITC |
| Tonbo Biotechnologies | Anti-Mouse CD274 (PD-L1, B7-H1) (10F.9G2) | PE |
| LifeSpan BioSciences | Anti-human CD274/B7-H1/PD-L1 Antibody | FITC, PE |
| LifeSpan BioSciences | Anti-human CD274/B7-H1/PD-L1 Antibody (clone MIH2) | FITC, RPE |
| LifeSpan BioSciences | Anti-human CD274/B7-H1/PD-L1 Antibody (clone MIH6) | FITC |
| LifeSpan BioSciences | Anti-human CD274/B7-H1/PD-L1 Antibody (aa19-238, clone 12K56) | APC |
| LifeSpan BioSciences | Anti-human CD274/B7-H1/PD-L1 Antibody (clone 27A2) | PE |
| LifeSpan BioSciences | Anti-human CD274/B7-H1/PD-L1 Antibody (clone ANC6H1) | FITC, RPE |
| LifeSpan BioSciences | Anti-mouse CD274/B7-H1/PD-L1 Antibody (clone MIH5) | PE |
| LifeSpan BioSciences | Anti-mouse CD274/B7-H1/PD-L1 Antibody (clone 10F.9G2) | APC, FITC |
| LifeSpan BioSciences | Anti-mouse CD274/B7-H1/PD-L1 Antibody (clone 29E.2A3) | APC, PE |
| BioLegend | Anti-mouse CD274 (B7-H1, PD-L1) Antibody | APC, Brilliant Violet 421, PE/DZL594, Brilliant Violet 711, PE, PE/Cy7, Brilliant Violet 605 |
| BioLegend | Anti-human CD274 (B7-H1, PD-L1) Antibody | APC, Brilliant Violet 421, Brilliant Violet 711, Brilliant Violet 605, APC, PE, PE/Cy7, PE/DZL594, PerCP/Cy5.5 |
| GenWay Biotech, Inc. | Anti-human CD274 Antibody | FITC |
| GenWay Biotech, Inc. | Anti-mouse CD274 Antibody | FITC |
| Abcam | Anti-human PD-L1 antibody (MIH2) | Phycoerythrin |
| Abcam | Anti-human PD-L1 antibody (28-8) | Alexa Fluor 647 |
| Abcam | Anti-mouse PD-L1 antibody (10F.9G2) | Phycoerythrin |

TABLE 1-continued

| Commercial Supplier | Antibody | Fluor. Conjugation |
| --- | --- | --- |
| BD Biosciences | Rat anti-mouse CD274 Antibody | PE, APC, BV711 |
| BD Biosciences | Mouse anti-human CD274 Antibody | APC, BB515, BV421, BV650, BV786, FITC, PE, PE-CF594, PE-Cy7 |
| Cell Signaling Technology | Anti-human PD-L1 (E1L3N) XP Rabbit mAb | Alexa Fluor 488, Alexa Fluor 647, PE |

In some instances, an unconjugated anti-PD-L1 antibody may find use in the herein described methods, including but not limited to e.g., those unconjugated anti-PD-L1 antibodies available from commercial suppliers including e.g., those commercial suppliers listed above in Table 1. In some instances, an unconjugated anti-PD-L1 antibody may be conjugated prior to use including but not limited to e.g., where the unconjugated antibody is conjugated to a fluorophore.

Anti-PD-L1 protein specific binding members are not limited to antibodies and may also, in some instances, include e.g., anti-PD-L1 aptamers, anti-PD-L1 haptens, etc. Additionally, synthetic specific binding members specific for PD-L1 protein may also be derived from the PD-L1 binding portion of PD-1. For example, in some instances, a PD-L1 specific binding member may be rationally designed to include a PD-1-derived PD-L1 binding domain e.g., based on the binding interaction of PD-1 and PD-L1, e.g., as shown in RCSB Protein Data Bank (PDB) structure 4ZQK and described in Zak et al., (2015) Structure 23:2341-2348; the disclosure of which is incorporated herein by reference in its entirety.

In some instances, the methods described herein may make use of a labeled binding member specific for PD-L1 transcript. A labeled binding member specific for PD-L1 transcript may specifically bind PD-L1 mRNA expressed in a cell. Useful specific binding members specific for PD-L1 transcript include but are not limited to oligonucleotides having complementary sequence to all or a portion of the PD-L1 mRNA sequence. In some instances, a useful oligonucleotide probe may include a sequence complementary to a human PD-L1 mRNA transcript including but not limited to e.g.:

```
Homo sapiens CD274 molecule (CD274), transcript
variant 1, mRNA (NM_014143.3):
                                  (SEQ ID NO: 3)
GGCGCAACGCTGAGCAGCTGGCGCGTCCCGCGCGGCCCCAGTTCTGCG

CAGCTTCCCGAGGCTCCGCACCAGCCGCGCTTCTGTCCGCCTGCAGGG

CATTCCAGAAAGATGAGGATATTTGCTGTCTTTATATTCATGACCTAC

TGGCATTTGCTGAACGCATTTACTGTCACGGTTCCCAAGGACCTATAT

GTGGTAGAGTATGGTAGCAATATGACAATTGAATGCAAATTCCCAGTA

GAAAAACAATTAGACCTGGCTGCACTAATTGTCTATTGGGAAATGGAG

GATAAGAACATTATTCAATTTGTGCATGGAGAGGAAGACCTGAAGGTT

CAGCATAGTAGCTACAGACAGAGGGCCCGGCTGTTGAAGGACCAGCTC

TCCCTGGGAAATGCTGCACTTCAGATCACAGATGTGAAATTGCAGGAT

GCAGGGGTGTACCGCTGCATGATCAGCTATGGTGGTGCCGACTACAAG

CGAATTACTGTGAAAGTCAATGCCCCATACAACAAAATCAACCAAAGA

ATTTTGGTTGTGGATCCAGTCACCTCTGAACATGAACTGACATGTCAG

GCTGAGGGCTACCCCAAGGCCGAAGTCATCTGGACAAGCAGTGACCAT

CAAGTCCTGAGTGGTAAGACCACCACCACCAATTCCAAGAGAGAGGAG

AAGCTTTTCAATGTGACCAGCACACTGAGAATCAACACAACAACTAAT

GAGATTTTCTACTGCACTTTTAGGAGATTAGATCCTGAGGAAAACCAT

ACAGCTGAATTGGTCATCCCAGAACTACCTCTGGCACATCCTCCAAAT

GAAAGGACTCACTTGGTAATTCTGGGAGCCATCTTATTATGCCTTGGT

GTAGCACTGACATTCATCTTCCGTTTAAGAAAAGGGAGAATGATGGAT

GTGAAAAATGTGGCATCCAAGATACAAACTCAAAGAAGCAAAGTGAT

ACACATTTGGAGGAGACGTAATCCAGCATTGGAACTTCTGATCTTCAA

GCAGGGATTCTCAACCTGTGGTTTAGGGGTTCATCGGGGCTGAGCGTG

ACAAGAGGAAGGAATGGGCCCGTGGGATGCAGGCAATGTGGGACTTAA

AAGGCCCAAGCACTGAAAATGGAACCTGGCGAAAGCAGAGGAGGAGAA

TGAAGAAAGATGGAGTCAAACAGGGAGCCTGGAGGGAGACCTTGATAC

TTTCAAATGCCTGAGGGGCTCATCGACGCCTGTGACAGGGAGAAAGGA

TACTTCTGAACAAGGAGCCTCCAAGCAAATCATCCATTGCTCATCCTA

GGAAGACGGGTTGAGAATCCCTAATTTGAGGGTCAGTTCCTGCAGAAG

TGCCCTTTGCCTCCACTCAATGCCTCAATTTGTTTTCTGCATGACTGA

GAGTCTCAGTGTTGGAACGGGACAGTATTTATGTATGAGTTTTTCCTA

TTTATTTTGAGTCTGTGAGGTCTTCTTGTCATGTGAGTGTGGTTGTGA

ATGATTTCTTTTGAAGATATATTGTAGTAGATGTTACAATTTTGTCGC

CAAACTAAACTTGCTGCTTAATGATTTGCTCACATCTAGTAAAACATG

GAGTATTTGTAAGGTGCTTGGTCTCCTCTATAACTACAAGTATACATT

GGAAGCATAAAGATCAAACCGTTGGTTGCATAGGATGTCACCTTTATT

TAACCCATTAATACTCTGGTTGACCTAATCTTATTCTCAGACCTCAAG

TGTCTGTGCAGTATCTGTTCCATTTAAATATCAGCTTTACAATTATGT

GGTAGCCTACACACATAATCTCATTTCATCGCTGTAACCACCCTGTTG

TGATAACCACTATTATTTTACCCATCGTACAGCTGAGGAAGCAAACAG

ATTAAGTAACTTGCCCAAACCAGTAAATAGCAGACCTCAGACTGCCAC

CCACTGTCCTTTTATAATACAATTTACAGCTATATTTTACTTTAAGCA

ATTCTTTTATTCAAAAACCATTTATTAAGTGCCCTTGCAATATCAATC

GCTGTGCCAGGCATTGAATCTACAGATGTGAGCAAGACAAAGTACCTG

TCCTCAAGGAGCTCATAGTATAATGAGGAGATTAACAAGAAAATGTAT
```

-continued

TATTACAATTTAGTCCAGTGTCATAGCATAAGGATGATGCGAGGGGAA

AACCCGAGCAGTGTTGCCAAGAGGAGGAAATAGGCCAATGTGGTCTGG

GACGGTTGGATATACTTAAACATCTTAATAATCAGAGTAATTTTCATT

TACAAAGAGAGGTCGGTACTTAAAATAACCCTGAAAAATAACACTGGA

ATTCCTTTTCTAGCATTATATTTATTCCTGATTTGCCTTTGCCATATA

ATCTAATGCTTGTTTATATAGTGTCTGGTATTGTTTAACAGTTCTGTC

TTTTCTATTTAAATGCCACTAAATTTTAAATTCATACCTTTCCATGAT

TCAAAATTCAAAAGATCCCATGGGAGATGGTTGGAAAATCTCCACTTC

ATCCTCCAAGCCATTCAAGTTTCCTTTCCAGAAGCAACTGCTACTGCC

TTTCATTCATATGTTCTTCTAAAGATAGTCTACATTTGGAAATGTATG

TTAAAAGCACGTATTTTTAAAATTTTTTTCCTAAATAGTAACACATTG

TATGTCTGCTGTGTACTTTGCTATTTTTATTTATTTTAGTGTTTCTTA

TATAGCAGATGGAATGAATTTGAAGTTCCCAGGGCTGAGGATCCATGC

CTTCTTTGTTTCTAAGTTATCTTTCCCATAGCTTTTCATTATCTTTCA

TATGATCCAGTATATGTTAAATATGTCCTACATATACATTTAGACAAC

CACCATTTGTTAAGTATTTGCTCTAGGACAGAGTTTGGATTTGTTTAT

GTTTGCTCAAAAGGAGACCCATGGGCTCTCCAGGGTGCACTGAGTCAA

TCTAGTCCTAAAAAGCAATCTTATTATTAACTCTGTATGACAGAATCA

TGTCTGGAACTTTTGTTTTCTGCTTTCTGTCAAGTATAAACTTCACTT

TGATGCTGTACTTGCAAAATCACATTTTCTTTCTGGAAATTCCGGCAG

TGTACCTTGACTGCTAGCTACCCTGTGCCAGAAAAGCCTCATTCGTTG

TGCTTGAACCCTTGAATGCCACCAGCTGTCATCACTACACAGCCCTCC

TAAGAGGCTTCCTGGAGGTTTCGAGATTCAGATGCCCTGGGAGATCCC

AGAGTTTCCTTTCCCTCTTGGCCATATTCTGGTGTCAATGACAAGGAG

TACCTTGGCTTTGCCACATGTCAAGGCTGAAGAAACAGTGTCTCCAAC

AGAGCTCCTTGTGTTATCTGTTTGTACATGTGCATTTGTACAGTAATT

GGTGTGACAGTGTTCTTTGTGTGAATTACAGGCAAGAATTGTGGCTGA

GCAAGGCACATAGTCTACTCAGTCTATTCCTAAGTCCTAACTCCTCCT

TGTGGTGTTGGATTTGTAAGGCACTTTATCCCTTTTGTCTCATGTTTC

ATCGTAAATGGCATAGGCAGAGATGATACCTAATTCTGCATTTGATTG

TCACTTTTTGTACCTGCATTAATTTAATAAAATATTCTTATTTATTTT

GTTACTTGGTACACCAGCATGTCCATTTTCTTGTTTATTTTGTGTTTA

ATAAAATGTTCAGTTTAACATCCCAGTGGAGAAAGTTAAAAAA or

Homo sapiens CD274 molecule (CD274), transcript variant 2, mRNA (NM_001267706.1):
(SEQ ID NO: 4)
GGCGCAACGCTGAGCAGCTGGCGCGTCCCGGGGGGCCCCAGTTCTGCG

CAGCTTCCCGAGGCTCCGCACCAGCCGCGCTTCTGTCCGCCTGCAGGG

CATTCCAGAAAGATGAGGATATTTGCTGTCTTTATATTCATGACCTAC

TGGCATTTGCTGAACGCCCCATACAACAAAATCAACCAAAGAATTTTG

GTTGTGGATCCAGTCACCTCTGAACATGAACTGACATGTCAGGCTGAG

GGCTACCCCAAGGCCGAAGTCATCTGGACAAGCAGTGACCATCAAGTC

CTGAGTGGTAAGACCACCACCACCAATTCCAAGAGAGAGGAGAAGCTT

TTCAATGTGACCAGCACACTGAGAATCAACACAACAACTAATGAGATT

TTCTACTGCACTTTTAGGAGATTAGATCCTGAGGAAAACCATACAGCT

GAATTGGTCATCCCAGAACTACCTCTGGCACATCCTCCAAATGAAAGG

ACTCACTTGGTAATTCTGGGAGCCATCTTATTATGCCTTGGTGTAGCA

CTGACATTCATCTTCCGTTTAAGAAAAGGGAGAATGATGGATGTGAAA

AAATGTGGCATCCAAGATACAAACTCAAAGAAGCAAAGTGATACACAT

TTGGAGGAGACGTAATCCAGCATTGGAACTTCTGATCTTCAAGCAGGG

ATTCTCAACCTGTGGTTTAGGGGTTCATCGGGGCTGAGCGTGACAAGA

GGAAGGAATGGGCCCGTGGGATGCAGGCAATGTGGGACTTAAAAGGCC

CAAGCACTGAAAATGGAACCTGGCGAAAGCAGAGGAGGAGAATGAAGA

AAGATGGAGTCAAACAGGGAGCCTGGAGGGAGACCTTGATACTTTCAA

ATGCCTGAGGGGCTCATCGACGCCTGTGACAGGGAGAAAGGATACTTC

TGAACAAGGAGCCTCCAAGCAAATCATCCATTGCTCATCCTAGGAAGA

CGGGTTGAGAATCCCTAATTTGAGGGTCAGTTCCTGCAGAAGTGCCCT

TTGCCTCCACTCAATGCCTCAATTTGTTTTCTGCATGACTGAGAGTCT

CAGTGTTGGAACGGGACAGTATTTATGTATGAGTTTTTCCTATTTATT

TTGAGTCTGTGAGGTCTTCTTGTCATGTGAGTGTGGTTGTGAATGATT

TCTTTTGAAGATATATTGTAGTAGATGTTACAATTTTGTCGCCAAACT

AAACTTGCTGCTTAATGATTTGCTCACATCTAGTAAAACATGGAGTAT

TTGTAAGGTGCTTGGTCTCCTCTATAACTACAAGTATACATTGGAAGC

ATAAAGATCAAACCGTTGGTTGCATAGGATGTCACCTTTATTTAACCC

ATTAATACTCTGGTTGACCTAATCTTATTCTCAGACCTCAAGTGTCTG

TGCAGTATCTGTTCCATTTAAATATCAGCTTTACAATTATGTGGTAGC

CTACACACATAATCTCATTTCATCGCTGTAACCACCCTGTTGTGATAA

CCACTATTATTTTACCCATCGTACAGCTGAGGAAGCAAACAGATTAAG

TAACTTGCCCAAACCAGTAAATAGCAGACCTCAGACTGCCACCCACTG

TCCTTTTATAATACAATTTACAGCTATATTTTACTTTAAGCAATTCTT

TTATTCAAAAACCATTTATTAAGTGCCCTTGCAATATCAATCGCTGTG

CCAGGCATTGAATCTACAGATGTGAGCAAGACAAAGTACCTGTCCTCA

AGGAGCTCATAGTATAATGAGGAGATTAACAAGAAAATGTATTATTAC

AATTTAGTCCAGTGTCATAGCATAAGGATGATGCGAGGGGAAAACCCG

AGCAGTGTTGCCAAGAGGAGGAAATAGGCCAATGTGGTCTGGGACGGT

TGGATATACTTAAACATCTTAATAATCAGAGTAATTTTCATTTACAAA

GAGAGGTCGGTACTTAAAATAACCCTGAAAAATAACACTGGAATTCCT

TTTCTAGCATTATATTTATTCCTGATTTGCCTTTGCCATATAATCTAA

TGCTTGTTTATATAGTGTCTGGTATTGTTTAACAGTTCTGTCTTTTCT

ATTTAAATGCCACTAAATTTTAAATTCATACCTTTCCATGATTCAAAA

TTCAAAAGATCCCATGGGAGATGGTTGGAAAATCTCCACTTCATCCTC

CAAGCCATTCAAGTTTCCTTTCCAGAAGCAACTGCTACTGCCTTTCAT

-continued

```
TCATATGTTCTTCTAAAGATAGTCTACATTTGGAAATGTATGTTAAAA

GCACGTATTTTTAAAATTTTTTTCCTAAATAGTAACACATTGTATGTC

TGCTGTGTACTTTGCTATTTTTATTTATTTTAGTGTTTCTTATATAGC

AGATGGAATGAATTTGAAGTTCCCAGGGCTGAGGATCCATGCCTTCTT

TGTTTCTAAGTTATCTTTCCCATAGCTTTTCATTATCTTTCATATGAT

CCAGTATATGTTAAATATGTCCTACATATACATTTAGACAACCACCAT

TTGTTAAGTATTTGCTCTAGGACAGAGTTTGGATTTGTTTATGTTTGC

TCAAAAGGAGACCCATGGGCTCTCCAGGGTGCACTGAGTCAATCTAGT

CCTAAAAAGCAATCTTATTATTAACTCTGTATGACAGAATCATGTCTG

GAACTTTTGTTTTCTGCTTTCTGTCAAGTATAAACTTCACTTTGATGC

TGTACTTGCAAAATCACATTTTCTTTCTGGAAATTCCGGCAGTGTACC

TTGACTGCTAGCTACCCTGTGCCAGAAAAGCCTCATTCGTTGTGCTTG

AACCCTTGAATGCCACCAGCTGTCATCACTACACAGCCCTCCTAAGAG

GCTTCCTGGAGGTTTCGAGATTCAGATGCCCTGGGAGATCCCAGAGTT

TCCTTTCCCTCTTGGCCATATTCTGGTGTCAATGACAAGGAGTACCTT

GGCTTTGCCACATGTCAAGGCTGAAGAAACAGTGTCTCCAACAGAGCT

CCTTGTGTTATCTGTTTGTACATGTGCATTTGTACAGTAATTGGTGTG

ACAGTGTTCTTTGTGTGAATTACAGGCAAGAATTGTGGCTGAGCAAGG

CACATAGTCTACTCAGTCTATTCCTAAGTCCTAACTCCTCCTTGTGGT

GTTGGATTTGTAAGGCACTTTATCCCTTTTGTCTCATGTTTCATCGTA

AATGGCATAGGCAGAGATGATACCTAATTCTGCATTTGATTGTCACTT

TTTGTACCTGCATTAATTTAATAAAATATTCTTATTTATTTTGTTACT

TGGTACACCAGCATGTCCATTTTCTTGTTTATTTTGTGTTTAATAAAA

TGTTCAGTTTAACATCCCAGTGGAGAAAGTTAAAAAA.
```

Useful oligonucleotide probes may be DNA or RNA based and may include but are not limited to those probes used in in situ hybridization, including e.g., DNA in situ hybridization probes, RNA in situ hybridization probes (e.g., riboprobes), as well as anti-sense probes having one or more synthetic components including e.g., one or more synthetic nucleoside bases (such as e.g., a locked nucleic acid (LNA) and the like). Such probes may vary in length, ranging in some instances from 13 to 100 nt, such as 14 to 50 nt, e.g., 15 to 25 nt, etc. Oligonucleotide probes may be directly conjugated with a fluorophore, including e.g., those fluorophores described herein. In some instances, oligonucleotide probes may be conjugated with a moiety that allows for binding of a label once the oligonucleotide is hybridized. For example, an oligonucleotide may be conjugated to one or more biotin molecules allowing the oligonucleotide to be labeled after hybridization e.g., by introducing fluorescently labeled streptavidin.

Reagents useful in the herein described methods may also include labeled specific binding members specific for immune cells. Such specific binding members may allow for the identification of immune cells within a cell population of the instant disclosure and/or identification of a cell as not being an immune cell as described above.

Any convenient labeled specific binding member for an immune cell may find use in the herein described methods including but not limited to e.g., antibodies specific for individual immune cell markers including but not limited to e.g., an anti-CD114 antibody, an anti-CD117 antibody, an anti-CD11a antibody, an anti-CD11b antibody, an anti-CD14 antibody, an anti-CD15 antibody, an anti-CD16 antibody, an anti-CD182 antibody, an anti-CD19 antibody, an anti-CD20 antibody, an anti-CD22 antibody, an anti-CD24 antibody, an anti-CD25 antibody, an anti-CD3 antibody, an anti-CD30 antibody, an anti-CD31 antibody, an anti-CD34 antibody, an anti-CD38 antibody, an anti-CD4 antibody, an anti-CD45 antibody, an anti-CD56 antibody, an anti-CD61 antibody, an anti-CD8 antibody, an anti-CD91 antibody, an anti-Foxp3 antibody, and the like. Accordingly, in some instances, a detected neoplasia cell may be further characterized as lacking expression of or having expression of below a predetermined threshold of one or more immune cell markers, e.g., as detected using an antibody to an immune cell marker including e.g., those listed above.

As described above, e.g., regarding the detection of DNA content, the herein described methods may include detection of DNA using one or more DNA labeling reagents. Various DNA labeling reagents may find use in the herein described methods including but not limited to: Hoechst 33342 (2'-(4-Ethoxyphenyl)-5-(4-methyl-1-piperazinyl)-1H,1'H-2,5'-bibenzimidazole trihydrochloride) and Hoechst 33258 (4-[6-(4-Methyl-1-piperazinyl)-1',3'-dihydro-1H,2'H-2,5'-bibenzimidazol-2'-ylidene]-2,5-cyclohexadien-1-one trihydrochloride) and others of the Hoechst series; SYTO 40, SYTO 11, 12, 13, 14, 15, 16, 20, 21, 22, 23, 24, 25 (green); SYTO 17, 59 (red), DAPI, DRAQ5™ (an anthraquinone dye with high affinity for double stranded DNA), YOYO-1, propidium iodide, YO-PRO-3, TO-PRO-3, YOYO-3 and TOTO-3, SYTOX Green, SYTOX, methyl green, acridine homodimer, 7-aminoactinomycin D, 9-amino-6-chloro-2-methoxyactridine.

The above-described markers include intracellular markers. As used herein, the term "intracellular markers" refers to components of the cell that are within the cell beyond the outer surface of the plasma membrane. Such components may be or may be within any interior component of the cell including but not limited to the inner surface of the plasma membrane, the cytoplasm, the nucleus, mitochondria, endoplasmic reticulum, etc. As such, labeling or detection of intracellular markers requires transport of a specific label or specific binding agent of the intracellular marker across at least the outer surface of the plasma membrane. In some instances, a label or specific binding agent for an intracellular marker may be membrane permeable thus not requiring modulation of membrane permeability for labeling of the intracellular marker. In some embodiments, a label or specific binding agent for an intracellular marker may be membrane impermeable thus requiring modulation of membrane permeability for labeling of the intracellular marker, including, e.g., preparation and or treatment of the cells with one or more permeabilizing reagents as described herein.

The above-described markers include cell surface markers. As used herein, the term "cell surface markers" refers to components of the cell that are at least exposed, partially or completely, on the outer surface of the plasma membrane of cell and thus may be accessed without modulating cell permeability, e.g., without the use of one or more permeabilizing reagents as described herein. In some instances, cell surface markers include components of the cell that have a portion exposed on the outer surface of the cell membrane but also contain an intracellular portion and/or a transmembrane portion.

As described herein and as will be readily apparent to one or ordinary skill in the art, any combination of the agents and labels described herein may be employed in the methods described provided the combination is appropriate and the components do not physically or optically interfere. For example, where alterations or substitutions of particular labels can and/or should be employed in order to allow for the combination of two or more desired components is within the skill of the ordinary artisan. As a non-limiting example, where a particular fluorescent label of a biomarker interferes optically (e.g., has an overlapping emission spectra) with a desired DNA labeling agent of a particular emission wavelength, the fluorescent label of the biomarker may be substituted with a different fluorescent label having no or less emission spectra overlap with the desired DNA labeling agent.

Methods of Treating

As summarized above, the present disclosure includes methods of treating a subject for a neoplasia. The terms "subject," "individual," "host," and "patient," are used interchangeably herein and refer to any mammalian subject for whom diagnosis, treatment, or therapy is desired, particularly humans.

Aspects of the subject methods generally include identifying an anti-PD-1/PD-L1 immunotherapy responsive neoplasia in a subject and treating the subject by administering to the subject an anti-PD-1/PD-L1 immunotherapy. Identifying a neoplasia in a subject as an anti-PD-1/PD-L1 immunotherapy responsive may be performed according to any of the methods described herein and will generally include cytometrically detecting a cell of the neoplasia that expresses PD-L1 above a predetermined threshold.

Subjects treated according to the herein described methods include subjects having a neoplasia suspected of expressing PD-L1. In some instances, subjects treated according to the herein described methods may be subjects having a neoplasia suspected of or showing symptoms of immune evasion. Various indicators may suggest immune evasion by a neoplasia including but not limited to e.g., tumor growth or progression, immunosuppression, unresponsiveness to immunotherapy, and the like. Various factors and events present in the tumor microenvironment may be directly indicative of immune evasion or tumor progression, which indirectly indicates immune evasion, including but not limited to e.g., presence of activated T cells in the absence of appropriate costimulation, tumor cell expression of T cell—inhibitory molecules (e.g., HLA-G, HLA-E, etc.), tumor antigen loss, downregulation of MHC molecules, regulatory T cells (Tregs) (e.g., CD4+CD25+ Tregs, CD4+ CD25+ FoxP3+, etc.), presence of CD1d-restricted T cells, immunosuppressive factors and tumor-derived cytokines (e.g., transforming growth factor (TGF)-8, tumor necrosis factor (TNF)-α, VEGF, IL-1, IL-1β, IL-6, IL-8, IL-10, GM-CSF, type I IFNs, gangliosides, receptor-binding cancer-associated surface antigen (RCAS1), etc.), presence of immunosuppressive myeloid cell populations (immature myeloid cell populations e.g., those expressing iNOS (also known as NOS2) or arginase 1 (ARG1), myeloid-derived suppressor cells (MDSCs), modulated dendritic cells (DCs), alternatively-activated M1 and M2 macrophages, CD11b+ Gr1+ MDSCs, etc.), TCR downregulation, upregulation of immunosuppressive enzymes (e.g., indoleamine 2,3-dioxygenase (IDO), arginase, inhibitor of nuclear factor kappa-B kinase (IKK)2, etc.), and the like. In some instances, particular tumor characteristics may also be indicative of immune evasion, including but not limited to e.g., tumor resistance to cytotoxic pathways (e.g., as seen in tumors with FAS mutations), mutations in the gene encoding the TRAIL receptor death receptor 5 (DR5), overexpression of the anti-apoptotic molecules (e.g., FLIP, BCL-XL, etc.), and the like.

In some instances, the herein described methods of detecting anti-PD-1/PD-L1 immunotherapy responsive cells in a subject may serve to limit the administration of an anti-PD-1/PD-L1 immunotherapy to a subject having an immune-related disorder or a subject that is at increased risk of developing an immune-related disorder. By virtue of being naturally expressed on immune cells, PD-L1 targeted therapies can negatively impact immune cells of a subject. In some instances, the methods of the present disclosure may be used to screen subjects prior to anti-PD-1/PD-L1 immunotherapy, including e.g., those subjects most likely to be negatively impacted by anti-PD-1/PD-L1 immunotherapy or have adverse events due to anti-PD-1/PD-L1 immunotherapy, including e.g., those subjects with immune-related disorders.

Non-limiting examples of immune-related disorders include but are not limited to e.g., autoimmune disorders such as e.g., Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (now termed Granulomatosis with Polyangiitis (GPA), and the like.

In some instances, immune-related disorders may also include an activated immune system, e.g., as present in a subject fighting an infection or other immune stimulating condition.

In some instances, a subject with a neoplasia may be tested to determine whether one or more cells of the subject's neoplasia expresses PD-L1 above a predetermined threshold and, if the one or more cells is detected, the subject may be subsequently treated with an anti-PD-1/PD-L1 immunotherapy. Any neoplasia may be assayed to assess the likelihood that the subject's neoplasia is anti-PD-1/PD-L1 immunotherapy responsiveness, including whether or not the subject's neoplasia has previously shown indicators of immune evasion.

In some instances, a subject diagnosed with a neoplasia is assessed to determine the likelihood of responsiveness to anti-PD-1/PD-L1 immunotherapy, as described herein, prior to receiving any other treatment for the neoplasia. In some instances, a subject diagnosed with a neoplasia is assessed to determine the likelihood of responsiveness to anti-PD-1/PD-L1 immunotherapy, as described herein, while receiving a course of therapy for the neoplasia. In some instances, a subject diagnosed with a neoplasia is assessed to determine the likelihood of responsiveness to anti-PD-1/PD-L1 immunotherapy, as described herein, after receiving a course of therapy for the neoplasia.

Neoplasia therapies that may be administered to a subject before, during or after a subject is assessed for anti-PD-1/PD-L1 immunotherapy responsiveness will vary depending on numerous factors including e.g., the type of neoplasia, the subject's medical history, general state of health and/or any co-morbidities, and the like. Useful neoplasia therapies include but are not limited to e.g., radiation therapy, chemotherapy, immunotherapy, and the like. Neoplasia therapies, such as but not limited to radiation therapy, chemotherapy, immunotherapy, and the like, may be administered locally or systemically.

In some instances, a subject may be assessed for anti-PD-1/PD-L1 immunotherapy responsiveness before a course of therapy is begun including but not limited to e.g., immunotherapy. For example, in some instances, a medical professional may assay a subject to determine the anti-PD-1/PD-L1 immunotherapy responsiveness of the subject's cancer prior to administering an anti-PD-1/PD-L1 immunotherapy and the medical professional may administer the therapy only if the subject's neoplasia is identified as likely to be anti-PD-1/PD-L1 immunotherapy responsive, e.g., through the detection of one or more cells expressing PD-L1 above a predetermined threshold.

The amount of time before starting a course of treatment that a subject may be assessed to determine whether the neoplasia of the subject is anti-PD-1/PD-L1 immunotherapy responsive may vary and may range from 1 day or less to a month or more including but not limited to e.g., 1 day, 2 days, 3 days, 4 days, 5 days, 6 days, 1 week, 2 weeks, 3 weeks, 1 month, etc. In some instances, a course of treatment may be begun the same day that an assessment for anti-PD-1/PD-L1 immunotherapy responsiveness of a subject's neoplasia is performed.

In some instances, a subject may be assessed for anti-PD-1/PD-L1 immunotherapy responsiveness after a course of treatment has already been administered. For example, in some instances, a subject's neoplasia may be assayed for anti-PD-1/PD-L1 immunotherapy responsiveness after a failed course of immunotherapy, including but not limited to e.g., anti-PD-1/PD-L1 immunotherapy. In some instances, if the assessment identifies the neoplasia as anti-PD-1/PD-L1 immunotherapy responsive then the anti-PD-1/PD-L1 immunotherapy may be attempted a second time. In some instances, if the assessment identifies the neoplasia as not anti-PD-1/PD-L1 immunotherapy responsive, then the medical professional may not attempt anti-PD-1/PD-L1 immunotherapy a second time. In some instances, an assessment indicating that a neoplasia is not anti-PD-1/PD-L1 immunotherapy responsive may indicate that another course of therapy (e.g., non-PD-L1 immunotherapy, chemotherapy, radiation therapy, etc.) is warranted.

The amount of time after a course of treatment has ended that a subject may be assessed to determine whether the neoplasia of the subject is anti-PD-1/PD-L1 immunotherapy responsive may vary and may range from 1 day or less to a month or more including but not limited to e.g., 1 day, 2 days, 3 days, 4 days, 5 days, 6 days, 1 week, 2 weeks, 3 weeks, 1 month, etc. In some instances, an assessment for anti-PD-1/PD-L1 immunotherapy responsiveness of a subject's neoplasia is performed the same day on which the course of therapy is ended. In some instances, an assessment for anti-PD-1/PD-L1 immunotherapy responsiveness may be performed during a long-term follow-up assessment of a subject. The length of time after a course of treatment at which point long-term follow-up is performed will vary and may range from 3 months or less to 10 years or more including but not limited to e.g., 3 months, 4 months, 5 months, 6 months, 7 months, 8 months, 9 months, 10 months, 11 months, one year, 1.5 years, 2 years, 3 years, 4 years, 5 years, 6 years, 7 years, 8 years, 9 years, 10 years, etc.

In some instances, an assessment of whether a subject has an anti-PD-1/PD-L1 immunotherapy responsive neoplasia may be performed during a course of therapy to treat the subject for the neoplasia. For example, a course of therapy to treat a subject for a neoplasia may be begun and during the course of therapy one or more assessments of anti-PD-1/PD-L1 immunotherapy responsiveness may be performed, e.g., to monitor the therapy. In some instances, a subject may be receiving a course of immunotherapy, including e.g., a course of anti-PD-1/PD-L1 immunotherapy, and one or more assessments of the anti-PD-1/PD-L1 immunotherapy responsiveness of the subject's neoplasia may be performed during the immunotherapy. Such assessments may be performed for a variety of reasons including but not limited to e.g., the assess whether to continue the immunotherapy, to assess whether to alter the course of immunotherapy (e.g., change the immunotherapy drug being administered, change the dose of immunotherapy drug being administered, change the frequency of administration, etc.). For example, if an assessment during a course of therapy indicates that the subject's neoplasia is anti-PD-1/PD-L1 immunotherapy responsive then the subject may be switched to an anti-PD-1/PD-L1 immunotherapy or the subject's dose of an anti-PD-1/PD-L1 immunotherapy may be increased or the frequency of administering the subject an anti-PD-1/PD-L1 immunotherapy may be increased. Conversely, if an assessment during a course of therapy indicates that the subject's neoplasia is not anti-PD-1/PD-L1 immunotherapy responsive then the subject may be switched to a non-anti-PD-1/PD-L1 immunotherapy or the subject's dose of an anti-PD-1/PD-L1 immunotherapy may be decreased or terminated or the frequency of administering the subject an anti-PD-1/PD-L1 immunotherapy may be decreased or terminated.

Assessments made during a course of treatment may also be referred to herein as monitoring, including monitoring anti-PD-1/PD-L1 immunotherapy responsiveness. Besides monitoring subjects receiving anti-PD-1/PD-L1 immunotherapy for anti-PD-1/PD-L1 immunotherapy responsiveness, the subject methods also include monitoring a neoplasia of a subject for anti-PD-1/PD-L1 immunotherapy responsiveness during the course of a treatment that is not an anti-PD-1/PD-L1 immunotherapy treatment. For example, in some instances, a subject undergoing radiation therapy may be monitored for anti-PD-1/PD-L1 immunotherapy responsiveness and, if the subject's neoplasia is identified as anti-PD-1/PD-L1 immunotherapy responsive then a course of anti-PD-1/PD-L1 immunotherapy may be initiated, in conjunction with or instead of the radiation therapy. In some instances, a subject undergoing chemotherapy may be monitored for anti-PD-1/PD-L1 immunotherapy responsiveness and, if the subject's neoplasia is identified as anti-PD-1/PD-L1 immunotherapy responsive then a course of anti-PD-1/PD-L1 immunotherapy may be initiated, in conjunction with or instead of the chemotherapy. In some instances, a subject undergoing non-anti-PD-1/PD-L1 immunotherapy (i.e., immunotherapy having a target other than PD-L1 or PD-1) may be monitored for anti-PD-1/PD-L1 immunotherapy responsiveness and, if the subject's neoplasia is identified as anti-PD-1/PD-L1 immunotherapy responsive then a course of anti-PD-1/PD-L1 immunotherapy may be initiated, in conjunction with or instead of the non-anti-PD-1/PD-L1 immunotherapy.

Methods of treating a subject having a neoplasia that is or is predicted to be anti-PD-1/PD-L1 immunotherapy responsive will generally include administering the subject an anti-PD-1/PD-L1 immunotherapy. Any anti-PD-1/PD-L1 immunotherapy may find use in the subject methods including but not limited to e.g., those therapies that include administering to a subject an effective amount of one or more anti-PD-1/PD-L1 therapeutic antagonists where such antagonists include but are not limited to e.g., OPDIVO® (nivolumab), KEYTRUDA® (pembrolizumab), Tecentriq™ (atezolizumab), durvalumab (MEDI4736), avelumab (MSB0010718C), BMS-936559 (MDX-1105), CA-170, BMS-202, BMS-8, BMS-37, BMS-242 and the like.

Nivolumab (OPDIVO®) is a humanized IgG4 anti-PD-1 monoclonal antibody used to treat cancer. Pembrolizumab (KEYTRUDA®), formerly known as MK-3475, lambrolizumab, etc., is a humanized antibody used in cancer immunotherapy targeting the PD-1 receptor. Atezolizumab (Tecentriq™) is a fully humanized, engineered monoclonal antibody of IgG1 isotype against the PD-L1 protein. Durvalumab (MedImmune) is a therapeutic monoclonal antibody that targets PD-L1. Avelumab (also known as MSB0010718C; Merck KGaA, Darmstadt, Germany & Pfizer) is a fully human monoclonal PD-L1 antibody of isotype IgG1. BMS-936559 (also known as MDX-1105; Bristol-Myers Squibb) is a blocking antibody that has been shown to bind to PD-L1 and prevent its binding to PD-1 (see e.g., U.S. NIH Clinical Trial No. NCT00729664). CA-170 (Curis, Inc.) is a small molecule PD-L1 antagonist. BMS-202, BMS-8, BMS-37, BMS-242 are small molecule PD-1/PD-L1 complex antagonists that bind PD-1 (see e.g., Kaz et al., (2016) Oncotarget 7(21); the disclosure of which is incorporated herein by reference in its entirety).

Anti-PD-L1 antagonists, including e.g., antibodies, useful in the methods described herein include but are not limited to e.g., those described in U.S. Pat. Nos. 7,722,868; 7,794,710; 7,892,540; 7,943,743; 8,168,179; 8,217,149; 8,354,509; 8,383,796; 8,460,927; 8,552,154; 8,741,295; 8,747,833; 8,779,108; 8,952,136; 8,981,063; 9,045,545; 9,102,725; 9,109,034; 9,175,082; 9,212,224; 9,273,135 and 9,402,888; the disclosures of which are incorporated herein by reference in their entirety.

Anti-PD-1 antagonists, including e.g., antibodies, useful in the methods described herein include but are not limited to e.g., those described in U.S. Pat. Nos. 6,808,710; 7,029,674; 7,101,550; 7,488,802; 7,521,051; 8,008,449; 8,088,905; 8,168,757; 8,460,886; 8,709,416; 8,951,518; 8,952,136; 8,993,731; 9,067,998; 9,084,776; 9,102,725; 9,102,727; 9,102,728; 9,109,034; 9,181,342; 9,205,148; 9,217,034; 9,220,776; 9,308,253; 9,358,289; 9,387,247 and 9,402,899; the disclosures of which are incorporated herein by reference in their entirety.

Compositions that include one or more of the subject anti-PD-1/PD-L1 antagonists may be administered once per day, a few or several times per day, or even multiple times per day, depending upon, among other things, the indication being treated and the judgment of the prescribing physician.

Methods of administration may be chosen depending on the condition being treated and the pharmaceutical composition being administered, such as e.g., the anti-PD-1/PD-L1 pharmaceutical composition being administered. Administration of the subject agent(s) can be done in a variety of ways, including, but not limited to, local administration of the agent, including e.g., subcutaneously, intravenously, intraperitoneally, intramuscularly, and possibly direct injection to specified organs or tumors, although systemic administration may also be used. Administration of the pharmaceutical compositions may be through a single route or concurrently by several routes.

By "effective amount" is meant an amount sufficient to have a therapeutic effect. A effective amount that will treat a neoplasia will modulate the symptoms and/or the size of the neoplasia typically by at least about 1%, including but not limited to e.g., at least about 10%; at least about 20%; at least about 30%; at least about 50%. Such will result in, e.g., statistically significant and quantifiable changes in the numbers of cells being affected. This may be a decrease in the size of the primary tumor, a decrease in the numbers of micrometastases in distant organs, a decrease in recurrent metastatic disease, etc.

The methods of the present disclosure may, in some embodiments, provide for certain advantages such as but not limited to e.g., improved detection of a particular cell type, improved treatment decisions and/or improved treatment outcomes, and the like. Improved detection may include detection with improved specificity, detection with improved sensitivity, and detection with improved sensitivity and specificity. Advantages of improved detection may also include, in some embodiments, detection that is more efficient, more convenient, and/or more cost-effective. Improved treatment decisions include not only those decisions resulting in improved treatment outcomes, but also, in some instances, improved decisions as to whether or not to treat a subject, decisions preventing needless administration of an agent, treatments that are more cost-effective, efficient, and/or convenient, and the like. Other advantages, in some embodiments, may include but are not limited to reducing the number and/or different types of samples that need to be collected from a subject and/or analyzed, improved adherence with a specified treatment regimen, improved patient confidence in a prescribed treatment regimen, and the like.

Kits

Also provided are kits for practicing one or more of the above-described methods. The subject kits may vary greatly. Reagents and devices included in the subject kits include those mentioned above with respect to the methods of detecting a neoplastic cell that expresses PD-L1 above a predetermined threshold.

These would include, for example, specific binding members for PD-L1, including, for example, an antibody specific for PD-L1. Subject kits may further include one or more sample preparation reagents including but not limited to, e.g., cell fixatives, cell permeabilizing reagents, cell labeling reagents, buffers, diluents, etc. The above components may be present in separate containers or one or more components may be combined into a single container, e.g., a glass or plastic vial. In some instances, kits of the instant disclosure may further include a sample preparation device such as e.g., a homogenizer.

Kits may further include sample obtainment devices, e.g., blood collection devices or biopsy collection devices. Non-limiting examples of biopsy collection devices include but are not limited to e.g., needle biopsy devices, core biopsy devices, punch biopsy devices, surgical biopsy devices, vacuum assisted biopsy devices, etc. In some instances, kits may further include one or more reagents and/or devices for cell dissociation including but not limited to e.g., enzymes, enzyme inhibitors, detergents, cell dissociation media or buffer, vortex devices, nutating devices, rocking devices, etc. Subject kits may further include control reagents and samples including but not limited to, e.g., control cell samples (e.g., positive control cellular samples, negative control cellular samples, etc.) calibration reagents (e.g., fluorescent beads, pre-labeled cells, etc.).

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Notwithstanding the appended claims, the disclosure is also defined by the following clauses:

1. A method of detecting whether a neoplastic cell that expresses programmed-death ligand 1 (PD-L1) above a predetermined threshold is present in a neoplasia sample, the method comprising:
   contacting the neoplasia sample with a labeled binding member specific for PD-L1 to generate a labeled cell suspension;
   cytometrically assaying the labeled cell suspension to quantify per cell PD-L1 expression to detect whether a neoplastic cell that expresses PD-L1 above a predetermined threshold is present in the neoplasia sample.
2. The method according to Clause 1, wherein the cytometrically assaying further comprises assaying cell cycle.
3. The method according to Clause 2, wherein assaying cell cycle comprises quantifying per cell DNA content.
4. The method according to Clause 2 or 3, wherein assaying cell cycle comprises detecting an expressed cell cycle marker.
5. The method according to any of the preceding clauses, wherein the method further comprises contacting the cell suspension sample with a DNA labeling reagent.
6. The method according to any of the preceding clauses, wherein the method further comprises contacting the neoplasia sample with a labeled binding member specific for an expressed cell cycle marker.
7. The method according to any of the preceding clauses, wherein the cytometrically assaying further comprises assaying aneuploidy.
8. The method according to any of the preceding clauses, wherein the detected cell is proliferative.
9. The method according to any of the preceding clauses, wherein the detected cell is aneuploid.
10. The method according to any of the preceding clauses, wherein the labeling further comprises contacting the neoplasia sample with at least one labeled binding member specific for immune cells.
11. The method according to Clause 10, wherein the at least one labeled binding member specific for immune cells comprises a labeled binding member specific for lymphocyte marker CD45.
12. The method according to Clause 10 or 11, wherein the at least one labeled binding member specific for immune cells comprises a labeled binding member specific for lymphocyte marker CD8.
13. The method according to any of Clauses 10-12, wherein the method comprises detecting cells that are negative for at least one marker of immune cells.
14. The method according to any of the preceding clauses, wherein the neoplasia sample is a body fluid sample.
15. The method according to Clause 14, wherein the body fluid sample is a blood sample.
16. The method according to Clause 14 or 15, wherein the detected cell is circulating tumor cell.
17. The method according to any of Clauses 14-16, wherein the detected cell is a hematopoietic cancer cell.
18. The method according to any of Clauses 1 to 13, wherein the neoplasia sample is a solid tumor sample.
19. The method according to Clause 18, wherein the solid tumor is an epithelial tumor.

20. The method according to Clause 18 or 19, wherein the solid tumor is a lung cancer tumor.
21. The method according to Clause 20, wherein the lung cancer tumor is a non-small cell lung cancer (NSCLC) tumor.
22. The method according to Clause 18 or 19, wherein the solid tumor is a breast cancer tumor.
23. The method according to any of Clauses 18 to 22, wherein the detected cells comprise squamous cell carcinoma cells.
24. The method according to any of Clauses 18 to 22, wherein the detected cells comprise adenocarcinoma cells.
25. The method according to any of Clauses 18 to 22, wherein the detected cells comprise adenosquamous carcinoma cells.
26. The method according to any of the preceding clauses, wherein the neoplasia sample is prepared from a biopsy.
27. The method according to Clause 26, wherein the biopsy is a solid tissue biopsy.
28. The method according to Clause 27, wherein the method further comprises preparing the neoplasia sample from the solid tissue biopsy.
29. The method of Clause 28, wherein preparing the neoplasia sample from the solid tissue biopsy comprises homogenizing tissue of the solid tissue biopsy.
30. The method according to Clause 26, wherein the biopsy is a liquid biopsy.
31. The method according to Clause 30, wherein the method further comprises preparing the neoplasia sample from the liquid biopsy.
32. The method according to Clause 26, wherein the biopsy is a fine needle aspiration (FNA) biopsy.
33. The method according to Clause 32, wherein the method further comprises preparing the neoplasia sample from the FNA biopsy.
34. The method according to any of the preceding clauses, wherein the cells of the labeled cell suspension sample are fixed.
35. The method according to any of the preceding clauses, wherein the method further comprises fixing the cells of the neoplasia sample.
36. The method according to Clause 35, wherein fixing the cells of the neoplasia sample is performed prior to the contacting.
37. The method according to Clause 35, wherein fixing the cells of the neoplasia sample is performed during the contacting.
38. The method according to Clause 35, wherein fixing the cells of the neoplasia sample is performed after the contacting.
39. The method according to any of Clauses 35 to 38, wherein fixing the cells comprises contacting the cells of the neoplasia sample with a mildly crosslinking agent.
40. The method according to Clause 39, wherein the mildly crosslinking agent comprises a formaldehyde-based fixative.
41. The method according to any of the preceding clauses, wherein the predetermined threshold is 100 or more PD-L1 molecules per cell.
42. The method according to clause 41, wherein the predetermined threshold is 500 or more PD-L1 molecules per cell.
43. The method according to clause 42, wherein the predetermined threshold is 1000 or more PD-L1 molecules.
44. A method of identifying whether a neoplasia in a subject is anti-programmed-death ligand 1 (PD-L1) immunotherapy responsive, the method comprising:
contacting a cell suspension sample prepared from the neoplasia with a labeled binding member specific for PD-L1 to generate a labeled cell suspension;
cytometrically assaying the labeled cell suspension to detect whether a population of cells that each express a level of PD-L1 that exceeds a predetermined threshold is present to identify whether the neoplasia is anti-PD-1/PD-L1 immunotherapy responsive.
45. The method according to Clause 44, wherein the cytometrically assaying further comprises assaying cell cycle.
46. The method according to Clause 45, wherein assaying cell cycle comprises quantifying per cell DNA content.
47. The method according to Clause 45 or 46, wherein assaying cell cycle comprises detecting an expressed cell cycle marker.
48. The method according to any of Clauses 44 to 47, wherein the method further comprises contacting the cell suspension sample with a DNA labeling reagent.
49. The method according to any of Clauses 44 to 48, wherein the method further comprises contacting the cell suspension sample with a labeled binding member specific for an expressed cell cycle marker.
50. The method according to any of Clauses 44 to 49, wherein the cytometrically assaying further comprises assaying aneuploidy.
51. The method according to any of Clauses 44 to 50, wherein the population of cells is proliferative.
52. The method according to any of Clauses 44 to 51, wherein the population of cells is aneuploid.
53. The method according to Clause 52, wherein the aneuploid cells indicate the presence of circulating tumor cells in the subject.
54. The method according to any of Clauses 44 to 53, wherein the labeling further comprises contacting the cell suspension sample with at least one labeled binding member specific for immune cells.
55. The method according to Clause 54, wherein the at least one labeled binding member specific for immune cells comprises a labeled binding member specific for lymphocyte marker CD45.
56. The method according to Clause 54 or 55, wherein the at least one labeled binding member specific for immune cells comprises a labeled binding member specific for lymphocyte marker CD8.
57. The method according to any of Clauses 54 to 56, wherein the method further comprises cytometrically assaying the labeled cell suspension to detect whether proliferative immune cells are present.
58. The method according to Clause 57, wherein the method further comprises quantifying the amount of proliferative immune cells.
59. The method according to any of Clauses 54 to 58, wherein method comprises identifying whether the population of cells is negative for a marker of immune cells.
60. The method according to any of Clauses 44 to 59, wherein the population of cells comprises circulating tumor cells.
61. The method according to any of Clauses 44 to 60, wherein the neoplasia is a hematopoietic cancer.

62. The method according to any of Clauses 44 to 60, wherein the neoplasia is a solid tumor.
63. The method according to Clause 62, wherein the solid tumor is an epithelial tumor.
64. The method according to Clause 62 or 61, wherein the solid tumor is a lung cancer tumor.
65. The method according to Clause 64, wherein the lung cancer tumor is a non-small cell lung cancer (NSCLC) tumor.
66. The method according to Clause 62 or 63, wherein the solid tumor is a breast cancer tumor.
67. The method according to any of Clauses 63 to 66, wherein the population of cells comprises squamous cell carcinoma cells.
68. The method according to any of Clauses 63 to 66, wherein the population of cells comprises adenocarcinoma cells.
69. The method according to any of Clauses 63 to 66, wherein the population of cells comprises adenosquamous carcinoma cells.
70. The method according to any of Clauses 44 to 69, wherein the cell suspension sample is prepared from a biopsy.
71. The method according to Clause 70, wherein the biopsy is a solid tissue biopsy.
72. The method according to Clause 71, wherein the method further comprises preparing the cell suspension sample from the solid tissue biopsy.
73. The method according to Clause 72, wherein preparing the cell suspension sample from the solid tissue biopsy comprises homogenizing tissue of the solid tissue biopsy.
74. The method according to Clause 70, wherein the biopsy is a liquid biopsy.
75. The method according to Clause 74, wherein the method further comprises preparing the cell suspension sample from the liquid biopsy.
76. The method according to Clause 70, wherein the biopsy is a fine needle aspiration (FNA) biopsy.
77. The method according to Clause 76, wherein the method further comprises preparing the cell suspension sample from the FNA biopsy.
78. The method according to any of Clauses 44 to 77, wherein the cells of the labeled cell suspension sample are fixed.
79. The method according to any of Clauses 44 to 78, wherein the method further comprises fixing the cells of the cell suspension sample.
80. The method according to Clause 79, wherein fixing the cells of the cell suspension is performed prior to the contacting.
81. The method according to Clause 79, wherein fixing the cells of the cell suspension is performed during the contacting.
82. The method according to Clause 79, wherein fixing the cells of the cell suspension is performed after the contacting.
83. The method according to any of Clauses 79 to 82, wherein fixing the cells comprises contacting the cells of the cell suspension sample with a mildly crosslinking agent.
84. The method according to Clause 83, wherein the mildly crosslinking agent comprises a formaldehyde-based fixative.
85. The method according to any of Clauses 44 to 84, wherein the predetermined threshold is 100 or more PD-L1 molecules per cell.
86. The method according to clause 85, wherein the predetermined threshold is 500 or more PD-L1 molecules per cell.
87. The method according to clause 86, wherein the predetermined threshold is 1000 or more PD-L1 molecules.
88. The method according to any of Clauses 44 to 87, wherein the cytometrically assaying further comprises quantifying the size of the population of cells.
89. The method according to Clause 88, wherein if the size of the population of cells exceeds 1% of the neoplastic cells in the cell suspension sample the neoplasia is identified as anti-PD-1/PD-L1 immunotherapy responsive.
90. The method according to any of Clauses 44 to 89, wherein the neoplasia has been previously identified as PD-L1 positive by immunohistochemistry.
91. A method of treating a subject for a neoplasia, the method comprising:
administering an anti-PD-1/PD-L1 immunotherapy to a subject comprising an anti-PD-1/PD-L1 immunotherapy responsive neoplasia, wherein the neoplasia is identified as anti-PD-1/PD-L1 immunotherapy responsive according to the method of any of Clauses 44 to 90.
92. The method according to Clause 91, wherein the subject has been previously treated with chemotherapy.
93. The method according to Clause 91 or 92, wherein the subject has been previously treated with radiation therapy.
94. The method according to any of Clauses 91 to 93, wherein the subject has been previously treated with immunotherapy.
95. The method according to any of Clauses 91 to 94, wherein the subject has an immune-related disorder or is at increased risk of developing an immune-related disorder.
96. The method according to any of Clauses 91 to 95, wherein the anti-PD-1/PD-L1 immunotherapy comprises administering to the subject one or more anti-PD-1/PD-L1 therapeutic antagonists selected from the group consisting of: OPDIVO® (nivolumab), KEYTRUDA® (pembrolizumab), Tecentriq™ (atezolizumab), durvalumab (MED14736), avelumab (MSB0010718C), BMS-936559 (MDX-1105), CA-170, BMS-202, BMS-8, BMS-37 and BMS-242.
97. The method according to any of Clauses 91 to 96, wherein the method further comprises monitoring the anti-PD-1/PD-L1 immunotherapy responsiveness of the neoplasia during the therapy and continuing the therapy only when the neoplasia is identified as anti-PD-1/PD-L1 immunotherapy responsive.
98. The method according to Clause 97, wherein the monitoring comprises:
contacting a cell suspension sample from the neoplasia with a labeled binding member specific for PD-L1 to generate a labeled cell suspension;
cytometrically assaying the labeled cell suspension to detect whether a population of cells that each express a level of PD-L1 that exceeds a predetermined threshold is present to identify whether the tumor is anti-PD-1/PD-L1 immunotherapy responsive.
99. A kit comprising:
a labeled binding member specific for PD-L1; and
a cell suspension fixation solution comprising a fixation reagent.

100. The kit according to Clause 99, wherein the fixation reagent is a mildly crosslinking agent.
101. The kit according to Clause 100, wherein the mildly crosslinking agent comprises a formaldehyde-based fixative.
102. The kit according to any of Clauses 99 to 101, further comprising a permeabilization reagent.
103. The kit according to Clause 102, wherein the cell suspension fixation solution comprises the permeabilization reagent.
104. The kit according to any of Clauses 99 to 103, further comprising a homogenization device.
105. The kit according to any of Clauses 99 to 104, further comprising a DNA labeling reagent.
106. The kit according to any of Clauses 99 to 105, further comprising a labeled binding member specific for an expressed cell cycle marker.
107. The kit according to any of Clauses 99 to 106, further comprising at least one labeled binding member specific for immune cells.
108. The kit according to Clause 107, wherein the at least one labeled binding member specific for immune cells comprises a labeled binding member specific for lymphocyte marker CD45.
109. The kit according to Clause 107 or 108, wherein the at least one labeled binding member specific for immune cells comprises a labeled binding member specific for lymphocyte marker CD8.
110. The kit according to any of Clauses 99 to 109, wherein the kit further comprises a biopsy collection device.
111. A method of detecting whether a neoplastic cell having a heterogeneity index above a predetermined threshold is present in a neoplasia sample, the method comprising:
    contacting the neoplasia sample with a labeled binding member specific for programmed death ligand (PD-L1) to generate a labeled cell suspension;
    cytometrically assaying the labeled cell suspension to obtain a per cell heterogeneity index comprising quantification of per cell PD-L1 expression to detect whether a neoplastic cell that has a heterogeneity index above a predetermined threshold is present in the neoplasia sample.
112. The method according to Clause 111, wherein the heterogeneity index comprises a cytometric measurement of cell complexity.
113. The method according to Clauses 111 or 112, wherein the heterogeneity index comprises a DNA content determination.
114. The method according to any of Clauses 111 to 113, wherein the detected cell is proliferative.
115. The method according to any of Clauses 111 to 114, wherein the labeling further comprises contacting the neoplasia sample with at least one labeled binding member specific for immune cells.
116. The method according to any of Clauses 111 to 115, wherein the detected cell is a circulating tumor cell, a hematopoietic cancer cell, or a cell of a solid tumor.
117. The method according to any of Clauses 111 to 116, wherein the predetermined threshold comprises a cell complexity threshold, a DNA content threshold, and a PD-L1 threshold of 100 or more PD-L1 molecules per cell.
118. A method of indirectly detecting whether circulating tumor cells (CTCs) are present in a subject having a neoplasia, the method comprising:
    contacting a cell suspension sample prepared from the neoplasia with a DNA labeling reagent or a cell cycle marker to generate a labeled cell suspension;
    cytometrically assaying the labeled cell suspension to quantify whether proliferation in a population of cells of the neoplasia is above a predetermined threshold to indirectly detect whether CTCs are present in the subject.
119. The method according to Clause 118, wherein the method further comprises assessing aneuploidy of the cells of the population.
120. The method according to Clauses 118 or 119, further comprising contacting the cell suspension sample with a labeled binding member specific for PD-L1 and cytometrically assaying the labeled cell suspension to quantify whether cells of the population express a level of PD-L1 that exceeds a predetermined threshold.
121. The method according to any of Clauses 118 to 120, wherein the neoplasia is a lung cancer.
122. The method according to any of Clauses 118 to 121, wherein the method further comprises confirming whether CTCs are present by performing an assay that directly detects CTCs.
123. A method of treating a subject for a neoplasia, the method comprising:
    indirectly detecting whether CTCs are present in the subject according to the method of any of Clauses 118 to 122; and
    administering to the subject a systemic treatment when CTCs are indirectly detected to be present and administering to the subject a local treatment for the neoplasia when CTCs are absent.
124. The method according to Clause 123, wherein the systemic treatment comprises radiation therapy, chemotherapy, immunotherapy, or a combination thereof.
125. A kit comprising:
    a DNA labeling reagent, a cell cycle marker, a labeled binding member specific for PD-L1, or a combination thereof;
    a cell suspension fixation solution comprising a fixation reagent; and
    instructions for performing a method according to any of Clauses 1 to 14.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and Clon-Tech.

Example 1

Cell suspensions were prepared from freshly collected lung tissue or samples collected by Fine Needle Aspiration (FNA) according to the Fine Needle non-aspiration cytology (FNNAC) method (a.k.a. "Cytopuncture" method) as described in Brifford et al. (Acta Cytol. 1982 Mar-Apr; 26 (2):195-200). Samples were collected from subjects with healthy lungs as well as from patients with non-small cell lung cancer (NSCLC).

The freshly collected samples were prepared using the IncellDx, Inc. incellPREP Sample Preparation protocol (IncellDx, Inc. Menlo Park, CA). Briefly, the incellPrep protocol is designed to prepare single cell suspensions from fresh human sourced tissue samples. A homogenizer gently disrupts the tissue and the incellPrep reagent fixes and permeabilizes the individual cells in suspension. The incellPrep protocol is non-enzymatic. A small sample of the obtained tissue was placed in the provided 2 mL microcentrifuge tube with integrated cap. Dulbecco's Phosphate-Buffered Saline, pH 7.4 (D-PBS) (about 800 µL) and the homogenizer were added to the tube. The homogenizer was connected to the Power Supply and set to spin the blades at low speed (voltage adjusted to about 1V). Gentle tissue disruption occurred, dislodging the intact cells without shearing the cell membranes. After tissue disruption was complete, the homogenizer was discarded. The produced cell suspension was centrifuged (at about 600 g for 5 min.) to facilitate removal of the D-PBS by aspiration. The centrifuged cells were resuspended in the incellPrep reagent (about 2 mL) for fixation and permeabilization at ambient temperature for at least 1 hour.

The cell suspensions, either FNNAC or incellPrep prepared, were centrifuged (600 g for 5 min.), aspirated and a PBS/2% bovine serum albumin (BSA) solution was added. The PBS/2% BSA solution was removed by centrifugation and aspiration. The cell suspensions were labeled with an antibody panel containing antibodies for the detection of immune cells (CD3/CD8/CD45) and anti-PD-L1 antibody (Clone 28-8 or E1L3N; fluorescent conjugated) for 30 min. at ambient temperature. The labeling mix was removed by centrifugation and aspiration and the cells were washed with 1 mL PBS/2% BSA solution with gentle vortexing. Following removal of the wash solution, 200 µL of DAPI labeling solution at working concentration was added and the labeled cell suspensions were incubated in the dark, at ambient temperature, for 30 min.

A Beckman Coulter CytoFLEX platform having a 488 nm and 405 nm laser configuration was used for cytometric analysis. Control samples (SUPM2, PD-L1 positive control cells; PC3 PD-L1 negative control cells) were analyzed for PD-L1 expression. The results of control sample cytometric analysis, provided in FIG. 1 (left panel—positive control; right panel—negative control), showed clear separation between PD-L1 expressing and PD-L1 non-expressing cells.

Figure 2:
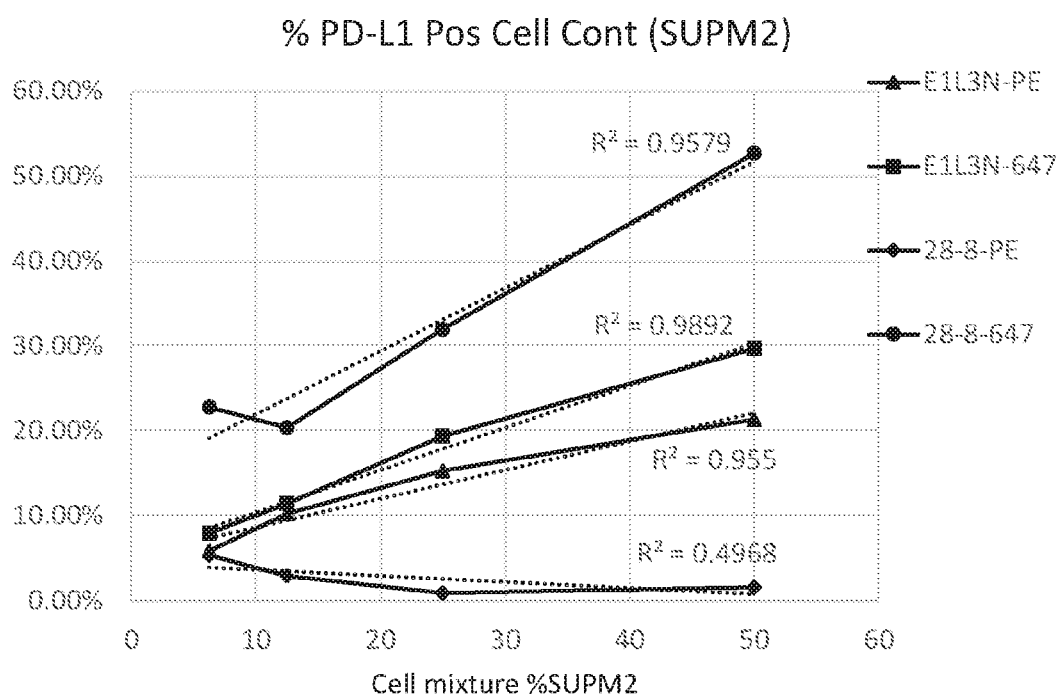
FIG. 2 depicts the linearity of PD-L1 positive cell detection in mixed samples prepared with various percentages of PD-L1 positive cells spiked into negative control samples.

Linearity of flow cytometric quantification of percent PD-L1 positive cells was evaluated. Briefly, cell mixing experiments were performed using samples of negative cells spiked with a known amount of positive control cells and the samples were assayed for flow cytometric detection of the positive cells using various anti-PD-L1 antibodies. Data from linearity testing is provided in FIG. 2, showing strong linearity for the calculated PD-L1 positive percentage (y-axis) across mixed cell samples having various percentages of PD-L1 positive control cells (x-axis).

Figure 3:
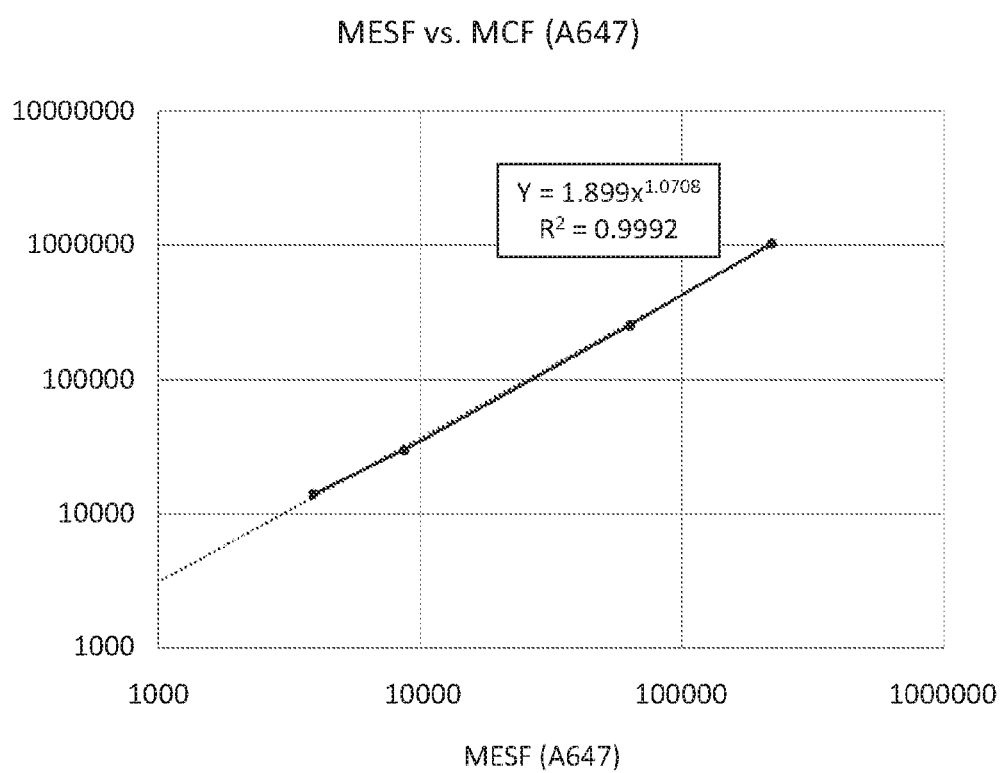
FIG. 3 depicts MESF bead based standardization of PD-L1 fluorescence for per cell PD-L1 quantification as used in an embodiment as described herein.

Linearity of flow cytometric quantification of per cell PD-L1 expression was also assayed. Calculated per cell PD-L1 receptor expression was based on mean fluorescence intensity of the cell staining using an anti-PD-L1 antibody clone with a known fluorescence to protein (FTP) ratio. Corresponding standard Molecules of Equivalent Soluble Fluorochrome (MESF) beads were run with each sample to facilitate quantification. The use of MESF beads, which have known copies of a fluorochrome, allows for the derivation of a quantitative standard curve based on total fluorescence of a bead or cell versus the number of fluorescence copies in the known standard. Receptor copy numbers were determined on a per cell basis by running the MESF bead standards with every run and calculating, based on the known number of fluorescence molecules bound to the antibody (FTP), the receptor copies per cell/cell type. An example of MESF-based standardized quantification is presented in FIG. 3.

Figure 4:
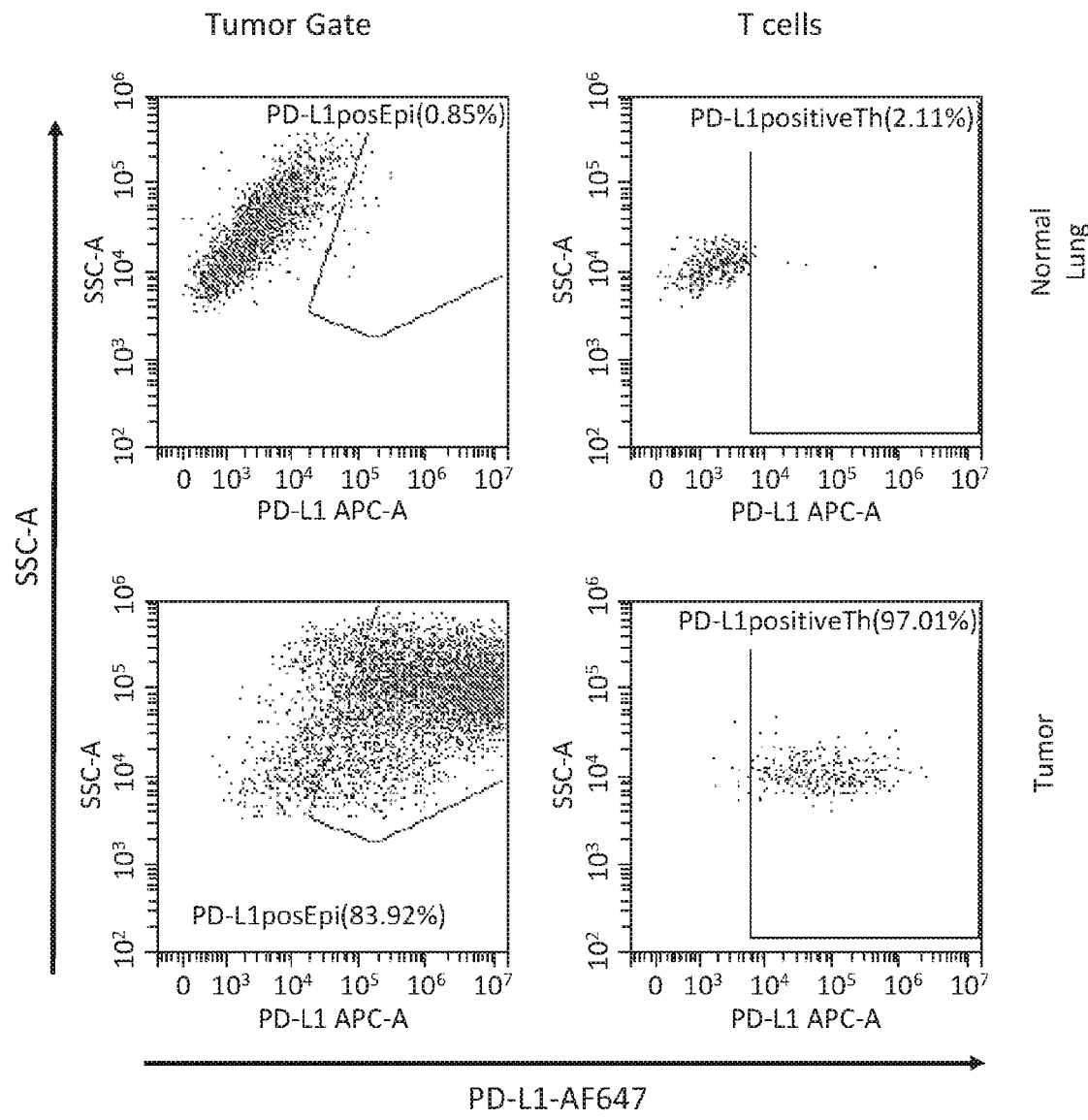
FIG. 4 depicts quantitative PD-L1 expression analysis of tumor and immune cell subsets and validation of the specific detection of PD-L1 expressing cells in patient derived samples.

Using a semi-automated, 96-well panel containing the 28-8 anti-PD-L1 clone labeled as a 1:1 FTP with Alexa Fluor 647, PD-L1 flow cytometric quantitative assays were validated using patient derived NSCLC samples. Assays included the quantification of the percentage of cell expressing PD-L1 over background as well as the number of PD-L1 receptors on a per cell basis. Such quantification was performed for both tumor cells and immune cell subsets from healthy ("normal lung") and NSCLC ("Tumor") patient samples. As shown in FIG. 4, detection of PD-L1 tumor cells was limited to tumor samples, validating use of this approach to detect PD-L1 positive cells cytometrically.

Testing has shown that PD-L1 expression can be similarly quantified in diploid cells as well as aneuploid cells. Using this approach various quantitative measures may be assessed including e.g., the percentage of tumor cells expressing PD-L1, the average number PD-L1 receptors expressed per tumor cell, the percentage of immune cells expressing PD-L1, the average number PD-L1 receptors expressed per immune cell, the percent aneuploid tumor cell population expressing PD-L1, the percent diploid tumor cell population expressing PD-L1, the percent tumor infiltrating lymphocytes (TIL), etc.

Example 2

Further clinical lung samples were prepared and flow cytometrically analyzed to obtain PD-L1 and cell cycle dye data for tumor and immune cells. Examples of the data obtained are shown in Table 2, provided in FIG. 5. Also provided for comparison in Table 2 is the percent PD-L1+ tumor data as assessed by immunohistochemistry (IHC).

To determine the correlation between single cell PD-L1 quantification done non-subjectively using flow cytometry vs. highly subjective conventional immunohistochemistry, matched/split samples were analyzed with one tissue sample submitted for formalin fixed paraffin embedded slides and another contiguous sample processed through an IVD, enzyme free, single cell preparation device as previously described (Chargin et al., (2016) Cancer Immunol Immunother. 65:1317-23; the disclosure of which is incorporated herein by reference in its entirety). Multi-parameter flow cytometry was performed and single nucleated cells were gated using PB450-Area vs PB450-Height dot plot analysis. Single nucleated cells were electronically separated into immune (CD45+, CD3+, CD4+, CD8+) populations and CD45−, diploid and aneuploid tumor cell populations. PD-L1 was quantified in the tumor cell and aneuploid tumor cell populations. PD-L1 quantification on the tumor cell population was compared to IHC quantification. Comparison of the OncoTect iO Lung Assay with the Dako PD-L1 IHC 28-8 PharmDx Kit revealed an overall concordance of 95% (diagnostic cutoff: ≥5%; negative percent agreement: 97%; positive percent agreement: 89%; overall agreement: 95%), with detection of one positive result by the OncoTect iO Lung Assay that was missed by IHC.

Figure 6:
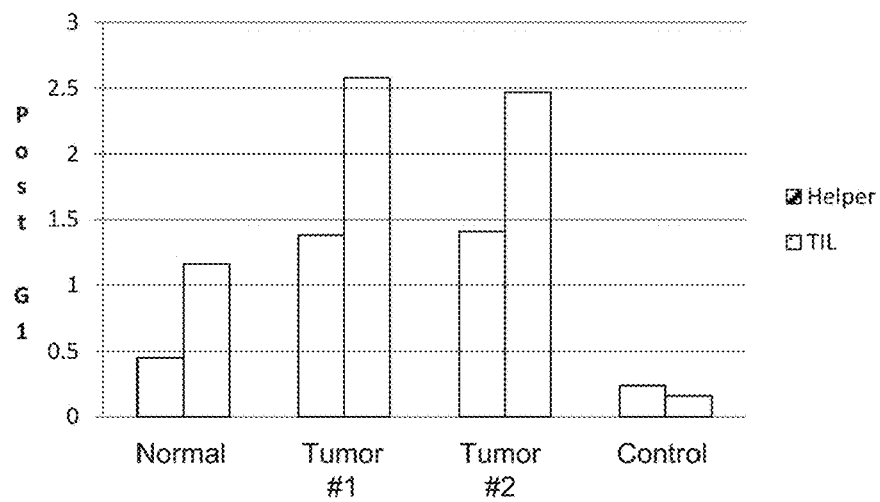
FIG. 6 depicts the proliferation of lung tumor tissue immune cell infiltrates assayed according to an embodiment described herein.

Data obtained from 22 clinical lung samples, along with control data used as baseline, was further analyzed. As the herein described approach quantifies tumor infiltrating lymphocytes (TIL) and cell cycle dye data, the proliferation state of the TILs can be assessed. FIG. 6 shows the post-G1 amounts of TILs and helper T cells as determined from normal tissue samples, tumor tissue samples (from two independent assays), and control cell samples. This data shows increased proliferation of the TILs present in tumor tissue as compared to those present in normal tissue. In addition, when control PBMCs are used as a marker of PBMCs, the tumor tissues were seen to have an influx of CD8+ TILs (35.9% vs. 22.3%). Taken together, this data demonstrates an increase in TILs within the tumor tissue space and that those TILs have increased proliferation as compared to normal tissue.

Figure 7:
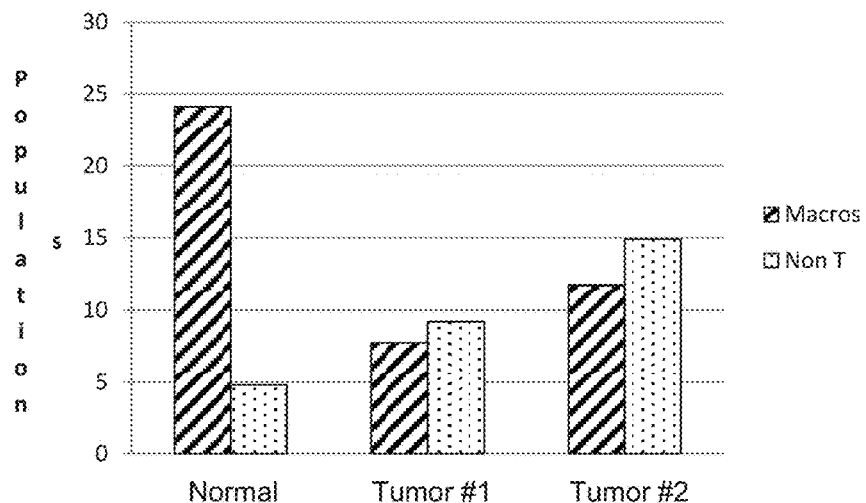
FIG. 7 depicts a loss of macrophages and an increase of non-T cells in tumor tissue as assayed according to an embodiment described herein.
Figure 8:
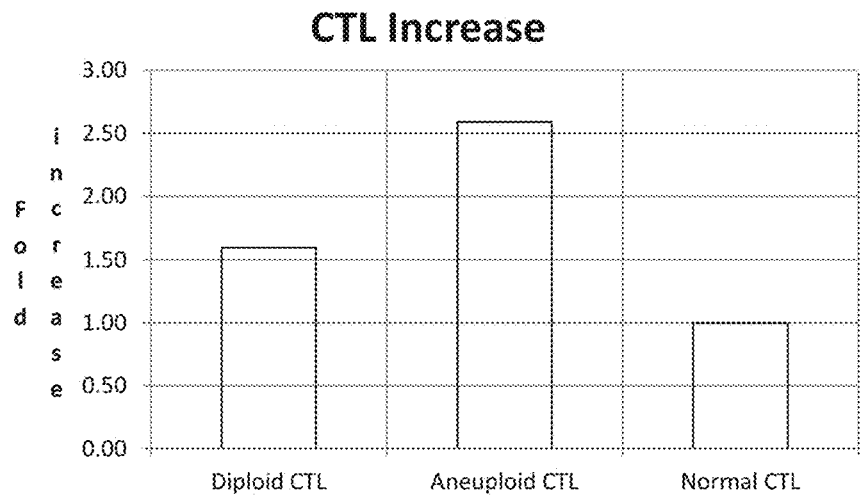
FIG. 8 depicts an increase in aneuploidy, as compared to diploidy, of lymphocytes present in tumor tissue as assayed according to an embodiment described herein.

The relative presence of macrophages as compared to non-T cells was also compared in the obtained data. As shown in FIG. 7, reduced numbers of macrophages were observed in lung tumor tissue samples (two independent assays) as compared to normal lung tissue samples. Thus, the analysis method described herein also demonstrates that tumor tissues lose antigen presenting cells, as compared to normal tissue. Accordingly, altogether the data presented in this example shows that the described method can detect a loss of macrophages, a gain of non-T cells and an increase in proliferation of CD8+ TILs and both CD3+ subsets in tumor tissue. In addition, as shown in FIG. 8, the described method can also detect an increase in aneuploidy among cytotoxic T lymphocytes (CTL), as compared to the amount of diploid CTLs, in the lung tissue samples (normalized for CTLs in normal tissue).

These data further demonstrate the ability of the herein described methods to detect and quantify clinically useful characteristics of tumor tissue samples, including characteristics of immune cells present in tumor tissues, such as e.g., the size of certain immune cell populations within the tumor tissue, the amount of aneuploidy within the populations, and the like. Not only can the assay quantify these cell populations in the tumor tissue, and ratios thereof, but the use of cell cycle dye analysis further allows one to determine the functional state of the cells detected, including e.g., the proliferation of immune infiltrates.

Example 3

As summarized above, the methods described herein can be further employed to, directly or indirectly, analyze tissue samples for circulating tumor cells (CTC). As an example, lung tissue samples were flow cytometrically analyzed for immune cell markers, PD-L1 and cell cycle parameters using a cell cycle dye as well as CTC detection. Table 3, as follows, provides the data from such assessment.

TABLE 3

| Sample | CD3 | CD8 | PD-L1(T)% | PD-L1(A)% | Aneuploid | CTC # | CTC PD-L1 |
|---|---|---|---|---|---|---|---|
| 1 | 84.7 | 35.2 | 22.5 | 28.0 | Yes | 243 | Yes |
| 2 | 85.7 | 58.4 | 0.6 | 0.6 | Yes | 9 | Yes |
| 3 | 80.6 | 28.85 | 14.5 | | No | 0 | |
| 4 | 79.5 | 43.5 | 40.1 | 50.1 | Yes | 12 | Yes |

As can be seen in the above data, the detection of aneuploidy in the primary lung tumor is indicative of the presence of CTCs. Accordingly, the results presented in this example further support the use of aneuploidy data, obtained according to the herein described methods from a tumor tissue sample, for predicting whether CTCs are likely to be present Example 4

The relationship between differences in PD-L1 expression relative to DNA content were further evaluated by comparing quantified PD-L1 expression as a function of DNA content (FIG. 9). As demonstrated in FIG. 9, DNA content as measured by fluorescence intensity typically appears as 1 chromosome equivalent (1O) with a small population of cells just prior to cell division appearing as twice (2C) the fluorescence intensity of diploid cells (1O). Tumor cells that are aneuploid have a DNA content that does not fall into the 1O or the 2C fluorescence equivalents. PD-L1 expression was found to vary in cells in different phases of the cell cycle, depending on the patient. In particular, the expression of PD-L1 was increased in the aneuploid populations relative to the diploid populations (FIG. 9).

Figure 10:
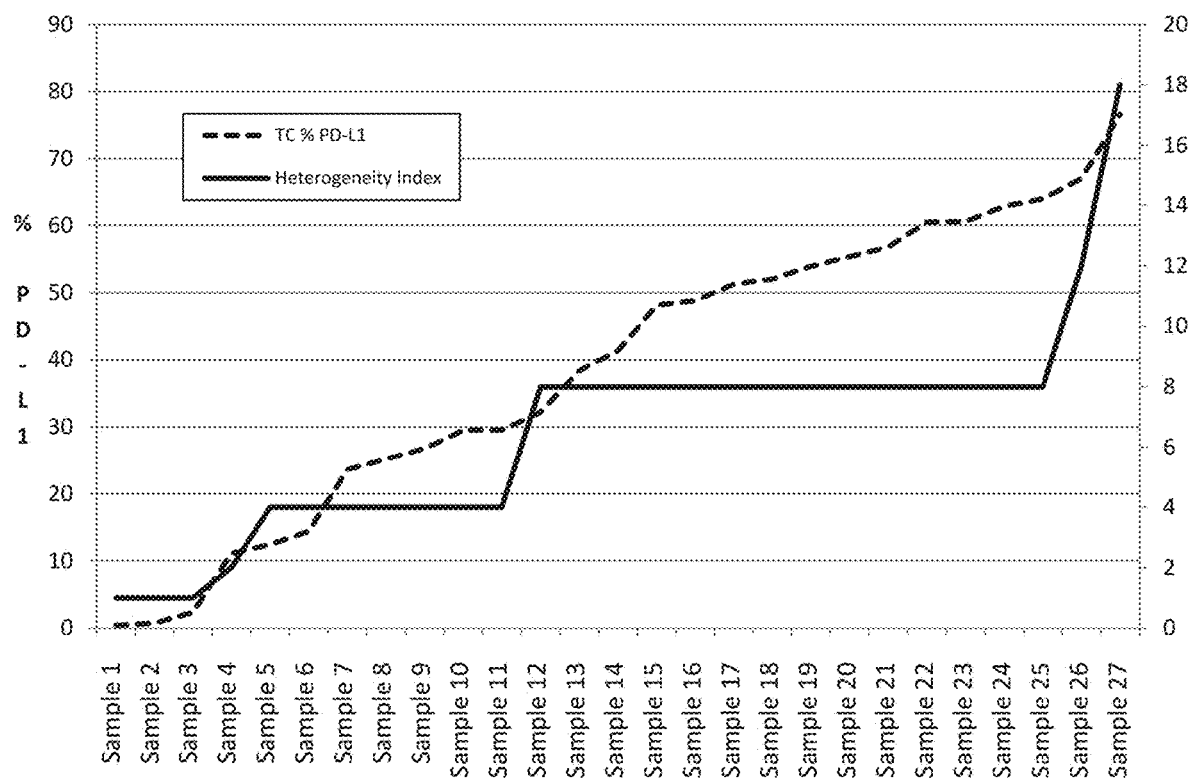
FIG. 10 depicts PD-L1 expression as a function of lung tumor heterogeneity.

Tumor heterogeneity was also further addressed. In particular, the influence of tumor heterogeneity on factors that influence treatment such as PD-L1 expression, tumor heterogeneity was determined based on three parameters: PD-L1 expression, side scatter (complexity), and DNA content. Based on these three parameters, it was demonstrated that multiple different clones of tumor exist in patient samples. When we plotted PD-L1 expression as a function of the determined heterogeneity index, it was found that the increase in PD-L1 expression is correlated with increasing tumor heterogeneity (FIG. 10).

Heterogeneity in NSCLC, both within tumor cells and in the tumor microenvironment, leads to challenges in tailoring effective patient treatment strategies. Most conventional molecular-based precision medicine diagnostics extract nucleic acids from these heterogeneous tumors and lose the context from which markers are expressed. Diagnostic approaches such those presented herein can address issues with tumor heterogeneity and the microenvironment by characterizing both the tumor and the tumor microenvironment using a cell-based, multi-parameter assay platforms. As a clinical assay, such analysis can contribute actionable information by quantifying TILs, determining tumor cell aneuploidy, and quantifying PD-L1 on both tumor cells and non-tumor cells in different phases of the cell cycle.

Anti-tumor immune responses are mediated by CD8+ cytotoxic T-lymphocytes (CTL) and the widespread success of immune checkpoint blockade through PD-1 and CTLA-4 provides clinical evidence that CTLs are capable of effective anti-tumor activity. Tumor infiltrating lymphocytes (TILs) have been shown to be key prognostic determinants in a number of solid tumors. TIL quantification has been included in the panel presented here, allowing for predictions of subject survival to be inferred from intratumor TIL measurements. Using this approach, increases in CD8+ CTL in NSCLC compared to normal lung tissue controls was found. In particular, CTLs were significantly increased in aneuploid NSCLC tumors compared to diploid tumors. Although markers of T-cell exhaustion such as TIM-3 and CTLA-4 were not included in the current panel, proliferation as determined by post $G_0$-$G_1$% in the current study serves as a powerful marker of T-cell activation and activity. Further probing of these CTL infiltrates revealed that the proliferation of these lymphocytes as measured by the post $G_0$-$G_1$% demonstrated a decrease in proliferation in the aneuploidy tumors relative to the diploid tumors. Another finding in the current study that may diminish immune control was the statistically significant decrease in antigen presenting cells in NSCLC tissue compared to normal lung tissue.

Aneuploidy, which is found in 65% of NSCLC tumors, is a prognostic factor in NSCLC. Meta-analyses have concluded that patients with diploid tumors experienced a significant reduction of risk of death from 1 to 5 years. Similarly, in other studies, the 3-year survival rate in patients with aneuploid type tumors was significantly lower than in those with the diploid type tumors. These studies concluded that the mortality rate in patients with aneuploid tumors was the result of distant metastases while, in patients with diploid tumors, local recurrence was the main reason for death. In the first three years after surgical resection, patients with aneuploid tumors were found to be at a higher risk of distant metastases than patients with the diploid type. Here, we have shown that 80% of NSCLC was aneuploid with DNA indices greater than 1.10. Furthermore, PD-L1 expression was variable from patient to patient depending on where the tumor cells were in the cell cycle. PD-L1 expression in aneuploidy tumor cells is particularly important because of the propensity of aneuploidy cells to appear as CTCs and to eventually metastasize.

Figure 11:
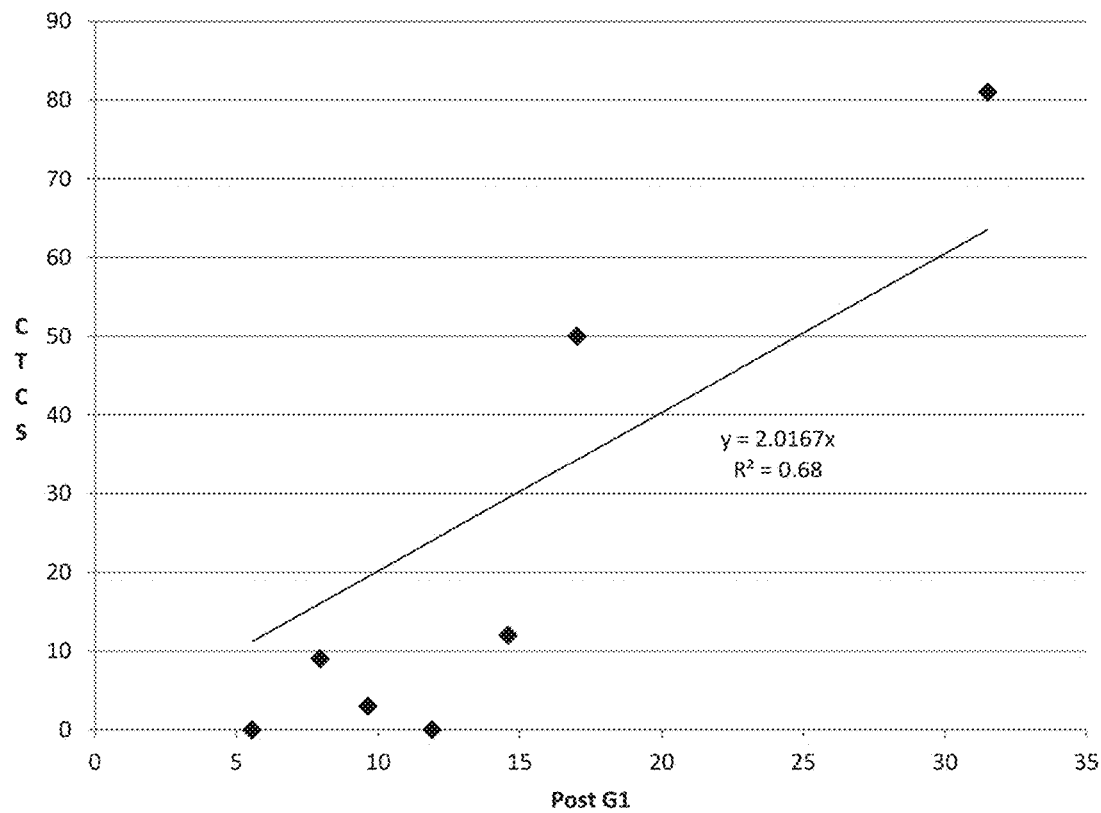
FIG. 11 depicts the correlation between the presence of circulating tumor cells (CTCs) and tumor proliferation.

The relationship between the presence of CTCs, as a surrogate for tumor metastasis, and tumor proliferation was further evaluated. CTCs were detected using an independent assay and CTC counts were plotted as a function of tumor proliferation (i.e., post $G_0$-$G_1$ in the primary tumor) (FIG. 11). Linear regression of these data revealed a correlation between tumor proliferation and the prevalence of CTCs. Accordingly, in the absence of independent CTC analysis, assaying primary tumor proliferation, as presented in the above described assays, allows for the presence of CTCs in the blood and, correspondingly, metastases to be predicted cytometrically.

Figure 12:
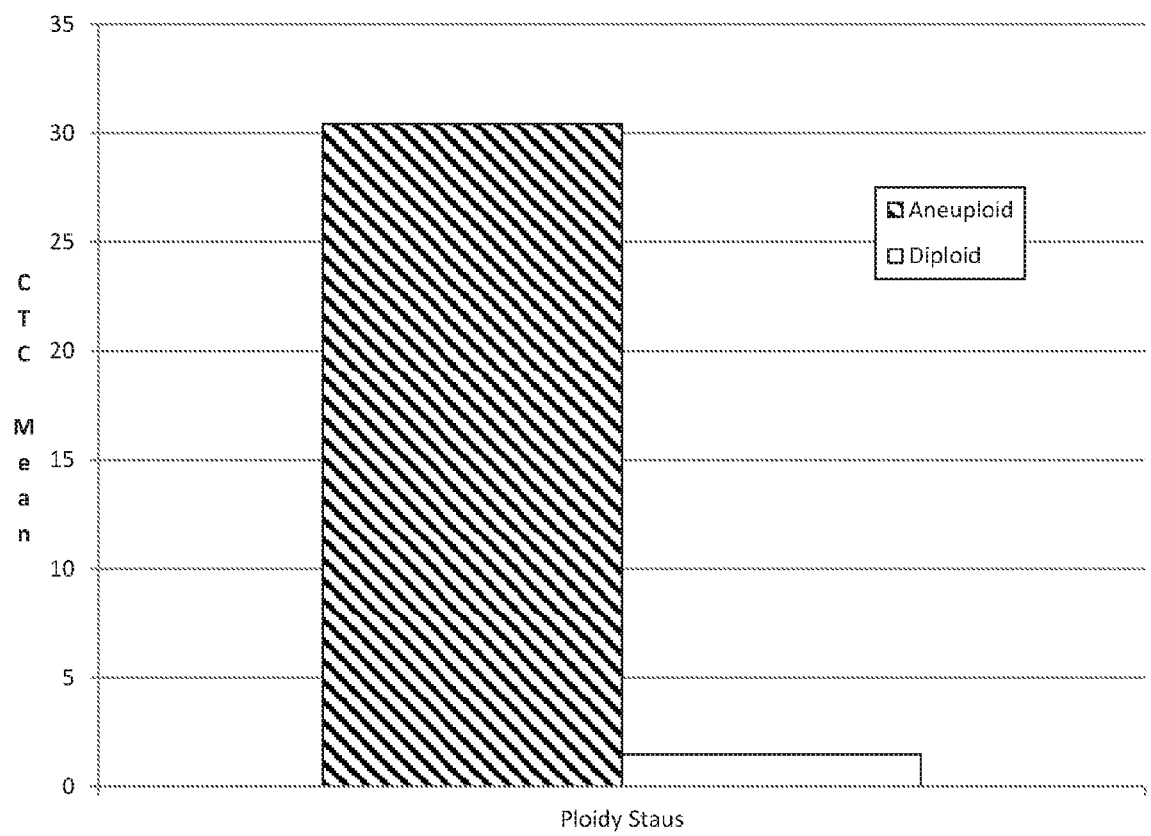
FIG. 12 depicts the correlation between the presence of circulating tumor cells (CTCs) and tumor aneuploidy.

In addition, the relationship between the presence of CTCs and tumor aneuploidy was also further investigated. Similar to the above, CTCs were detected using an independent assay and CTC counts were measured as a function of tumor cell aneuploidy determined from DNA content quantification. The result of this analysis is provided in FIG. 12, which shows the mean number of CTCs measured in diploid and aneuploid cell populations. As FIG. 12 depicts, on average, more CTCs are present in samples with aneuploid cell populations as compared to samples with diploid cell populations. Accordingly, ploidy status measured cytometrically in the assays described above also provides a predictive indicator as to the presence and prevalence of CTCs in a subject.

Overall, the tumor tissue workflow used in the present study resulted in more actionable information than conventionally used IHC methods. For example, it was found that the overall agreement between Oncotect iO and IHC was 95% (supra). In addition, Oncotect iO detected a distinct population of PD-L1 positive cells that was missed by IHC. No cases that were positive by IHC were missed by the OncoTect iO Assay. Furthermore, the prognostic information that the OncoTect iO Lung assay provided on TILs and aneuploidy, in addition to PD-L1 expression, positioned this assay to better inform clinicians about the patient tumor environment allowing for improved treatment decisions.

Materials and Methods

Samples

Fresh tissues were obtained from 19 NSCLC cases. Date of collection, age, sex, ethnicity, diagnosis, primary tumor size, and American Joint Committee on Cancer (AJCC) classification were recorded. Tissues were excised and then stored in Roswell Park Memorial Institute (RPMI) 1640 medium at 2-8° C. prior to overnight shipment to IncellDx on cold packs.

Tissue Dissociation Using IncellPREP

Tumor biopsies of at least 100 mg were placed in RPMI for transport after which 4 mm punches were taken from each tissue, of the entire tissue, and placed into Eppendorf tubes containing 800 μL Dulbecco's phosphate-buffered saline (DPBS). The entire tissue was utilized to generate the most representative single cell pool of cells to account for tumor heterogeneity across the tissue. IncellPREP (IncellDx, Inc) tissue homogenizers were inserted into each tube and set to run until supernatant appeared cloudy (<7.5 minutes). Cells were pelleted by centrifugation at 600×g and fixed and permeabilized in 1 mL IncellMax per 1 million live cells by trypan blue staining.

OncoTect iO Assay

Aliquots of 250,000 viable cells were tested with the OncoTect iO Lung Assay which contains antibodies directed against PD-L1 (28-8), CD45, CD3, and CD8, and a cell cycle dye. Following fixation for 1 hour in IncellMax, 250 μL of sample equivalent to 250,000 cells were aliquoted to 12×75 mm tubes and subsequently washed with 1 mL of DPBS+2% Bovine Serum Albumin (BSA). Samples were then stained with PD-L1-Alexa Fluor 647 (Clone 28-8, Abcam), CD45-FITC, CD3-PE, and CD8-PC5 (B3821F4A/SFCI21Thy2D3/UCHT1, Beckman Coulter) conjugated anti-human antibodies in DPBS+2% BSA and then incubated for 30 minutes at room temperature in the dark. Next, 1 mL of DPBS+2% BSA was added to each tube and incubated at room temperature for 5 minutes, prior to centrifugation at 600×g for 5 minutes. Supernatant was aspirated, and a wash with DPBS+2% BSA was repeated once. Following this wash, 100 μL of cell cycle dye at 1 μg/mL was added to each sample and incubated at room temperature for 30 minutes in the dark.

Flow Cytometry

Cells were first analyzed on a CytoFlex Cytometer (Beckman Coulter) using a PB450-Area by PB450-Height density plot to set a gate on nucleated single cells by the cell cycle dye staining. That gate was then applied to a CD45-FITC by side scatter plot to separate CD45+ immune cells from CD45− cells (epithelial/tumor cells). Immune cells were further separated into CD3+ and CD3+/CD8+ populations by a CD8-PC5 by CD3− PE scatter plot. A gate was established around the CD8+/CD3+ cells (cytotoxic T-cells).

Additionally, a PB450-Lin by count plot was used to gate on the CD45− diploid population. Once those populations were determined, each was analyzed for PD-L1 expression by forward scatter. A putative gate was established based on low/normal PD-L1 expression and was validated by this 19-sample dataset. PD-L1 expression above the normal cut off was recorded for CD45− population. Similarly, the presence of aneuploid cells was determined by calculating the ratio of Cell Cycle signal in the diploid gate for the CD45− and lymphocyte populations. A ratio of >1.05 (DNA index) is indicative of aneuploidy. When a ratio of >1.05 was determined, PD-L1 expression on the aneuploid CD45− cells was recorded. Tumor cell clones were calculated using SSC populations within the CD45 negative gate, DNA Index and +/−PD-L1 expression. The resultant product of these parameters is the heterogeneity index.

Immunohistochemistry

Concordance to IHC was tested by obtaining matched/split FFPE sections from the tissue biopsies. FFPE blocks were sectioned at 5 μm thickness. Slides were deparaffinized in a series of Xylenes and progressively diluted alcohols to water. After rinsing with DI water, the slides were treated with citrate-based antigen retrieval solution that was pre-heated to 65° C. Slides were incubated in the preheated citrate buffer and heated for 20 minutes at 99° C. and cooled down for 20 minutes before commencing immunohistochemical (IHC) staining on the Dako autostainer. Endogenous peroxidase was quenched with KPL solution, followed by protein blocking and rabbit anti-PD-L1 antibody (28-8 clone) incubation for 1 hour at room temperature. Relevant non-specific isotype control was used as negative control. After rinsing the primary antibodies, the slides were incubated with biotin conjugated secondary antibody and HRP-enzyme conjugated streptavidin, followed by incubation with diaminobenzidine (DAB) to visualize the signal. Upon completion of the IHC staining, the slides were de-hydrated in a series of alcohols and xylenes followed by cover-slipping for microscopic evaluation.

Example 5

Figure 13:
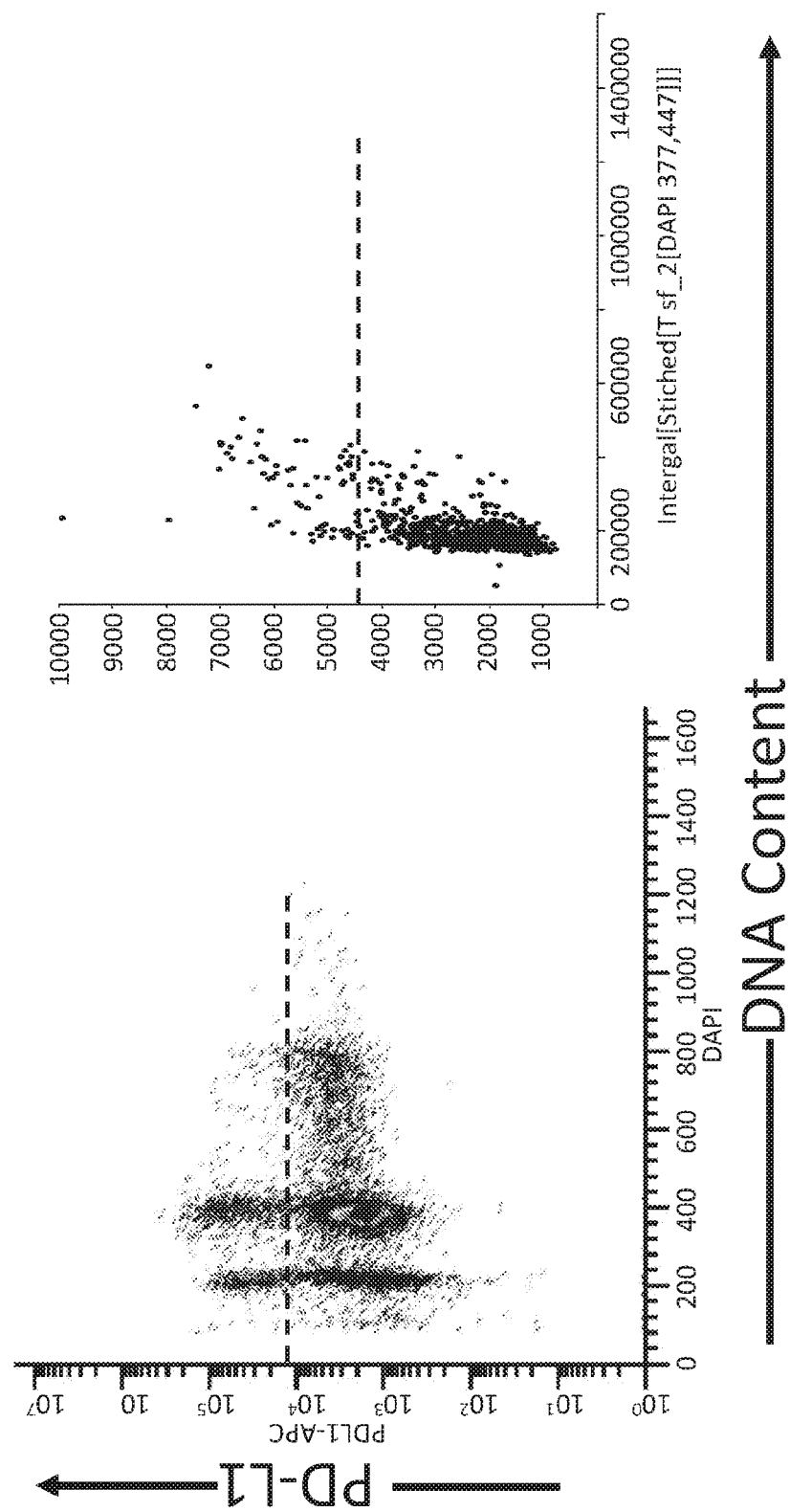
FIG. 13 depicts PD-L1 versus DNA content data obtained by flow cytometry (left) and circulating tumor cell (CTC) cell cytometry (right).

The comparability of data obtained flow cytometrically and data obtained using cell cytometry was compared. Samples were prepared essentially as described above and analyzed in parallel using a flow cytometer and a cell cytometer. Analysis showed that various flow cytometric parameters utilized in the methods described herein can be obtained cell cytometrically, e.g., using a CTC cell cytometer/sorter. For example, DNA content data and heterogeneity index data obtained flow cytometrically was comparable to DNA content data and heterogeneity index data obtained cell cytometrically. An example of the comparability of this data is provided in FIG. 13, which depicts PD-L1 expression versus DNA content obtained using a flow cytometer (left) and a CTC cell cytometer (right). Where cell cytometer analysis is substituted for flow cytometric analysis to obtain parameter used in method of the present disclosure, in some instances, corresponding cell cytometric measures may be substituted for flow cytometric measures. For example, where flow cytometric side scatter is employed as part of a heterogenetic index, a corresponding cell cytometric measure of cell complexity that is measurable by a cell cytometer may be substituted. At least in part, this example shows that certain data, such as DNA content data and heterogeneity index data, useful in the described methods obtained flow cytometrically may also be obtained cell cytometrically from automated imaging cytometer.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of indirectly detecting whether circulating tumor cells (CTCs) are present in a subject having a neoplasia, the method comprising:
   contacting a cell suspension sample prepared from the neoplasia with
      a labeled binding member specific for PD-L1; and
      a DNA labeling reagent or a cell cycle marker to generate a labeled cell suspension;
   cytometrically assaying the labeled cell suspension to quantify whether proliferation in a population of cells of the neoplasia is above a predetermined threshold to indirectly detect whether CTCs are present in the subject,
   wherein cytometrically assaying the labeled cell suspension comprises quantifying whether the cells of the population express a number of PD-L1 molecules per cell that exceeds the predetermined threshold.

2. The method according to claim 1, wherein the method further comprises assessing aneuploidy of the cells of the population.

3. The method according to claim 1, wherein the neoplasia is a lung cancer.

4. The method according to claim 1, wherein the method further comprises confirming whether CTCs are present by performing an assay that directly detects CTCs.

5. A method of treating a subject for a neoplasia, the method comprising:
   indirectly detecting whether CTCs are present in the subject according to the method of claim 1; and
   administering to the subject a systemic treatment when CTCs are indirectly detected to be present and administering to the subject a local treatment for the neoplasia when CTCs are absent.

6. The method according to claim 5, wherein the systemic treatment comprises radiation therapy, chemotherapy, immunotherapy, or a combination thereof.

7. The method according to claim 1, wherein the predetermined threshold comprises a cell complexity threshold, a DNA content threshold and a PD-L1 threshold of 100 or more PD-L1 molecules per cell.

8. The method according to claim 7, wherein the PD-L1 threshold is 500 or more PD-L1 molecules per cell.

9. The method according to claim 7, wherein the DNA content threshold is 1.05 times or more than the DNA content of a normal cell.

10. The method according to claim 1, wherein the sample is collected from a blood sample of the subject.

11. The method according to claim 1, wherein the sample is collected from a non-hematological tissue of the subject.

12. The method according to claim 6, wherein the immunotherapy comprises an anti-PD-1/PD-L1 immunotherapy.

* * * * *

UNITED STATES PATENT AND TRADEMARK OFFICE
CERTIFICATE OF CORRECTION

PATENT NO. : 12,298,309 B2
APPLICATION NO. : 18/211038
DATED : May 13, 2025
INVENTOR(S) : Bruce K. Patterson et al.

It is certified that error appears in the above-identified patent and that said Letters Patent is hereby corrected as shown below:

In the Specification

Replace "10,782,298:" with -- 10,782,298; -- (Column 1, Line 15).

Replace "CN10888," with -- CNTO888, -- (Column 18, Line 22).

Replace "Gene Tex" with -- GeneTex -- (Columns 29-30, Line 38).

Replace "(TGF)-8," with -- (TGF)-β, -- (Column 37, Line 52).

Replace "TCR" with -- TCR ζ-chain -- (Column 37, Line 61).

Replace "10" with -- 1C -- (Column 54, Line 36).

Signed and Sealed this
Eighth Day of July, 2025

Coke Morgan Stewart
*Acting Director of the United States Patent and Trademark Office*